(12) United States Patent
Khalili et al.

(10) Patent No.: US 10,279,014 B2
(45) Date of Patent: *May 7, 2019

(54) GENE EDITING METHODS AND COMPOSITIONS FOR ELIMINATING RISK OF JC VIRUS ACTIVATION AND PML (PROGRESSIVE MULTIFOCAL LEUKOENCEPHALOPATHY) DURING IMMUNOSUPPRESSIVE THERAPY

(71) Applicants: Excision BioTherapeutics, Inc., Bemindster, NJ (US); Temple University of the Commonwealth System of Higher Education, Philadelphia, PA (US)

(72) Inventors: Kamel Khalili, Bala Cynwyd, PA (US); Thomas Malcolm, Bedminster, NJ (US); Kenneth I. Kohn, West Bloomfield, MI (US)

(73) Assignees: Excision BioTherapeutics, Inc., Bedminster; Temple University of the Commonwealth System of Higher Education, Philadelphia ( * ) Notice: Subject to any disclaimer, the term of this patent is extended or adjusted under 35 U.S.C. 154(b) by 0 days.

This patent is subject to a terminal disclaimer.

(21) Appl. No.: 15/864,309

(22) Filed: Jan. 8, 2018

(65) Prior Publication Data

US 2018/0140682 A1    May 24, 2018

Related U.S. Application Data

(63) Continuation-in-part of application No. PCT/US2016/065583, filed on Dec. 8, 2016.

(60) Provisional application No. 62/265,109, filed on Dec. 9, 2015.

(51) Int. Cl.
| | |
|---|---|
| *C12Q 1/70* | (2006.01) |
| *A61K 38/46* | (2006.01) |
| *A61K 39/00* | (2006.01) |
| *A61K 48/00* | (2006.01) |
| *A61P 31/20* | (2006.01) |
| *C07K 16/28* | (2006.01) |
| *C12N 15/11* | (2006.01) |
| *A61K 39/395* | (2006.01) |

(52) U.S. Cl.
CPC ...... *A61K 38/465* (2013.01); *A61K 39/39541* (2013.01); *A61K 48/00* (2013.01); *A61P 31/20* (2018.01); *C07K 16/2839* (2013.01); *C12N 15/11* (2013.01); *C12Q 1/70* (2013.01); *A61K 2039/505* (2013.01); *C12N 2310/20* (2017.05)

(58) Field of Classification Search
CPC ............... A61K 2300/00; A61K 39/12; A61K 2039/53; A61K 39/42; A61K 2039/5254; A61K 2039/6075; A61K 38/465; A61K 39/39541; A61K 48/00; A61K 2039/505; C12N 7/00; C12N 15/1131; C12N 15/86; C12N 9/22; C12N 2710/22011; C12N 2710/22034; C12N 2310/11; C12N 2310/141; C12N 2501/727; C12N 2710/22043; C12N 2710/22041; C12N 2710/22071; C12N 2320/30; C12N 2310/20; C12N 15/00; C12N 15/111; C12N 15/11; C07K 14/005; C07K 16/084; C07K 14/025; C07K 14/01; C07K 16/2839; A61P 31/20; C12Q 1/70
See application file for complete search history.

(56) References Cited

U.S. PATENT DOCUMENTS

| | | | |
|---|---|---|---|
| 2012/0046340 A1 | 2/2012 | Gruber et al. | |
| 2015/0010901 A1 | 1/2015 | Khalili et al. | |
| 2017/0333572 A1* | 11/2017 | Khalili | ............ C12N 9/22 |

(Continued)

FOREIGN PATENT DOCUMENTS

| | | | |
|---|---|---|---|
| WO | WO-2014113493 A1 * | 7/2014 | ........... C07K 14/195 |
| WO | WO 2015184259 | 12/2015 | |

OTHER PUBLICATIONS

Wollebo HS, Bellizzi A, Kaminski R, Hu W, White MK, Khalili K. CRISPR/Cas9 System as an Agent for Eliminating Polyomavirus JC Infection. PLoS One. Sep. 11, 2015;10(9):e0136046. doi: 10.1371/journal.pone.0136046. eCollection 2015.*

(Continued)

*Primary Examiner* — Rachel B Gill
(74) *Attorney, Agent, or Firm* — Kohn & Associates, PLLC

(57) ABSTRACT

A method of eliminating the risk of JCV activation in a subject undergoing immunosuppressive therapy, by administering an effective amount of a gene editing composition directed toward at least one target sequence in the JCV genome, cleaving the target sequence in the JCV genome, disrupting the JCV genome, eliminating the JCV infection, eliminating the risk of JCV activation, and treating the subject with an immunosuppressive therapy. A pharmaceutical composition including at least one isolated nucleic acid sequence encoding a CRISPR-associated endonuclease and at least one gRNA having a spacer sequence complementary to a target sequence in a JCV DNA, the isolated nucleic acid sequences being included in at least one expression vector. Pharmaceutical compositions including at least one isolated nucleic acid sequence encoding at least one TALEN, at least one ZFN, and gene editing composition of C2c1, C2c3, TevCas9, Archaea Cas9, CasY.1-CasY.6, CasX, or argonaute protein, which target at least one nucleotide sequence of the JCV genome.

11 Claims, 4 Drawing Sheets

Specification includes a Sequence Listing.

(56) References Cited

U.S. PATENT DOCUMENTS

2018/0201921 A1* 7/2018 Malcolm .............. C12N 15/102
2018/0208914 A1* 7/2018 Malcolm ................ C12N 9/22

OTHER PUBLICATIONS

Cox DB, Platt RJ, Zhang F. Therapeutic genome editing: prospects and challenges. Nat Med. Feb. 2015;21(2):121-31.*

Cavanagh P, Garrity A. "CRISPR Mechanism", CRISPR/Cas9, Tufts University, 2014. https://sites.tufts.edu/crispr/. Accessed Sep. 10, 2018.*

Zhang Y, Ge X, Yang F, Zhang L, Zheng J, Tan X, Jin Zb, Qu J, Gu F. Comparison of non-canonical PAMs for CRISPR/Cas9-mediated DNA cleavage in human cells. Sci Rep. Jun. 23, 2014;4:5405.*

Pattanayak V, Guilinger JP, Liu DR. Determining the specificities of TALENs, Cas9, and other genome-editing enzymes. Methods Enzymol. 2014;546:47-78.*

White MK, Hu W, Khalili K. The CRISPR/Cas9 genome editing methodology as a weapon against human viruses. Discov Med. Apr. 2015;19(105):255-62.*

Hardy R. FDA hits pause on one of the first US human clinical trials to use CRISPR. https://newatlas.com/us-crispr-human-trial-hold-fda/54862/. May 31, 2018.*

Bondy-Denomy J, Garcia B, Strum S, Du M, Rollins MF, Hidalgo-Reyes Y, Wiedenheft B, Maxwell KL, Davidson AR. Multiple mechanisms for CRISPR-Cas inhibition by anti-CRISPR proteins. Nature. Oct. 1, 2015;526(7571):136-9. Epub Sep. 23, 2015.*

Wagner DL, et. al. High prevalence of *S. pyogenes* Cas9-specific T cell sensitization within the adult human population—A balanced effector/regulatory T cell response. bioRxiv 295139; doi: https://doi.org/10.1101/295139. Apr. 4, 2018.*

Chew WL. Immunity to CRISPR Cas9 and Cas12a therapeutics. Wiley Interdiscip Rev Syst Biol Med. Jan. 2018;10(1). Epub Oct. 30, 2017.*

Charlesworth CT, et. al. Identification of Pre-Existing Adaptive Immunity to Cas9 Proteins in Humans. bioRxiv 243345. Jan. 5, 2018.*

Yu C, Liu Y, Ma T, Liu K, Xu S, Zhang Y, Liu H, La Russa M, Xie M, Ding S, Qi LS. Small molecules enhance CRISPR genome editing in pluripotent stem cells. Cell Stem Cell. Feb. 5, 2015;16(2):142-7.*

Bennasser Y, Le SY, Benkirane M, Jeang KT. Evidence that HIV-1 encodes an siRNA and a suppressor of RNA silencing. Immunity. May 2005;22(5):607-19. Erratum in: Immunity. Jun. 2005;22(6):773.*

* cited by examiner

FIG. 1

```
2581 cagctttact taacagttgc agttattttg ggggaggggt ctttggtttt ttgaaacatt
2641 gaaagccttt acagatgtga aaagtgcagt tttcctgtgt gtctgcacca gaggcttctg
2701 agacctggga aaagcattgt gattgtgatt cagtgcttga tccatgtcca gagtcttctg
2761 cttcagaatc ttcctctcta ggaaagtcaa gaatgggtct ccccatacca acattagctt
2821 tcatagtaga aaatgtatac atgcttattt ctaaatccag cctttcttc cactgcacaa
2881 tcctctcatg aatggcagct gcaaagtcag caactggcct aaaccagatt aaaagcaaaa
2941 gcaaagtcat accactttgc aaaatccttt tttctagcaa atactcagag cagcttagtg
3001 attttctcag gtaggccttt ggtctaaaat ctatctgcct tacaaatctg gcctgtaaag
3061 ttctaggcac tgaatattca ttcatggtta caattccagg tggaaacacc tgtgttcttt
3121 tgttttggtg ttttctctct aaattaactt ttacacttcc atctaagtaa tctcttaagc
3181 aatcaaggtt gcttatgcca tgccctgaag gtaaatccct tgactctgca ccagtgcctt
3241 ttacatcctc aaatacaacc ataaactgat ctatacccac tcctaattca agtttaatc
3301 tttctaatgg catattaaca tttaatgact ttcccccaca gagatcaagt aaagctgcag
3361 ctaaagtagt tttgccactg tctattggcc ccttgaatag ccagtacctt ttttttggaa
3421 tgtttaatac aatgcatttt agaaagtcat aaataacagt gtccatttga ggcagcaagc
3481 aatgaatcca ggccacccca gccatatatt gctctaaaac agcattgcca tgtgccccaa
3541 aaattaagtc cattttatca agcaagaaat taaaccttc aactaacatt tcttctctgg
3601 tcatgtggat gctgtcaacc ctttgtttgg ctgctacagt atcaacagcc tgctggcaaa
3661 tgctttttg attttgcta tctgcaaaaa tttgggcatt ataatagtgt ttttcatgat
3721 ggttaaagtg atttggctga tcctttttt cacattttt gcattgctgt gggttttcct
3781 gaaagtctaa gtacatgccc ataagcaaaa aaacatcctc acacttggtt tccaaggcat
3841 actgtgtaac taatttccat gaaacctgct tagtttcttc tggttcttct gggttaaagt
3901 catgctcctt aaggccccc tgaatacttt cttccactac tgcatatggc tgtctacaca
3961 gggcactata aaacaagtat tccttattca cacctttaca aattaaaaaa ctaaaggtac
4021 atagttttg acagtagtta ttaattgctg acactctatg tctatgtggt gttaagaaaa
4081 acaaaatatt atgaccccca aaaccatgtc tacttataaa agttacagaa tattttccca
4141 taagtttctt atataaaatt tgagcttttt ctttagtggt atacacagca aagaagcaa
4201 cagttctatt actaaacaca gcttgactga ggaatgcatg cagatctaca ggaaagtctt
4261 tagggtcttc taccttttt ttcttttag gtggggtaga gtgttgggat cctgtgtttt
4321 catcatcact ggcaaacatt tcttcatggc aaaacaggtc ttcatcccac ttctcattaa
4381 atgtattcca ccaggattcc cattcatctg ttccataggt tggcacctaa aaaaaaacaa
4441 ttaagtttat tgtaaaaaac aaaatgccct gcaaagaaa aatagtggtt taccttaaag
4501 ctttagatcc ctgtagggg tgtctccaag aactttctcc cagcaatgaa gagcttcttg
4561 ggttaagtca cacccaaacc attgtctgaa gcaatcaaag caatagcaat ctatccacac
4621 aagtgggctg cttcttaaaa attttctgtt tctatgcctt aattttagca tgcacattaa
4681 acaggggcaa tgcactgaag gattagtggc acagttaggc cattccttgc aataaagggt
4741 atcagaatta ggaggaaaat cacaaccaac ctctgaacta ttccatgtac caaaatcagg
4801 ctgatgagca acttttacac cttgttccat ttttatat aaaaaattca ttctcttcat
4861 cttgtcttcg tccccacctt tatcagggtg gagttctttg catttttca gataagcttt
4921 tctcatgaca ggaatgttcc cccatgcaga cctatcaagg cctaataaat ccataagctc
4981 catggattcc tccctattca gcactttgtc cattttagct ttttgcagca aaaaattact
5041 gcaaaaaagg gaaaaacaag ggaatttccc tggcctccta aaaagcctcc acgcccttac
5101 tacttctgag taagcttgga ggcggaggcg    (SEQ ID NO: 13)
```

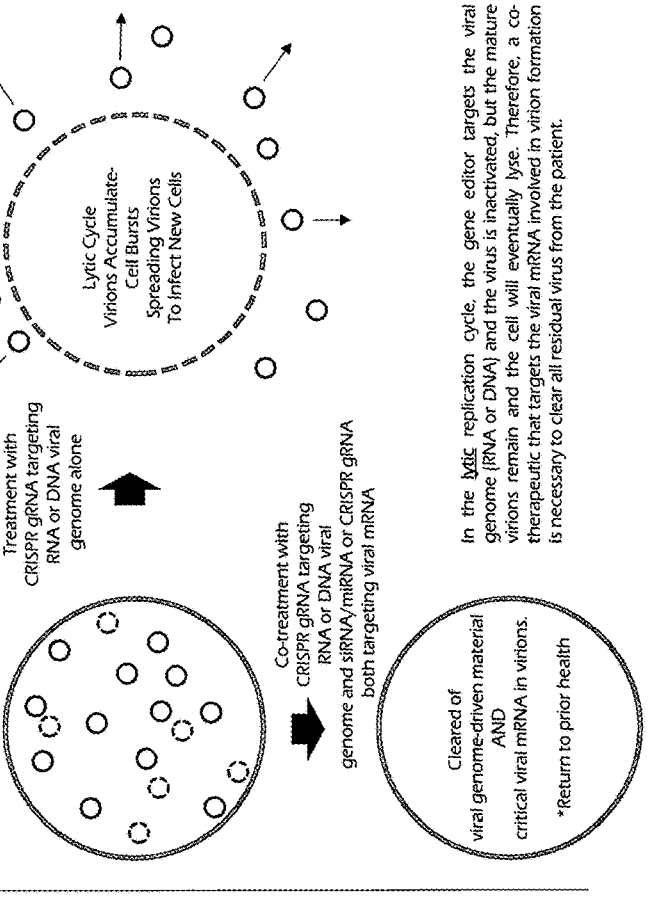
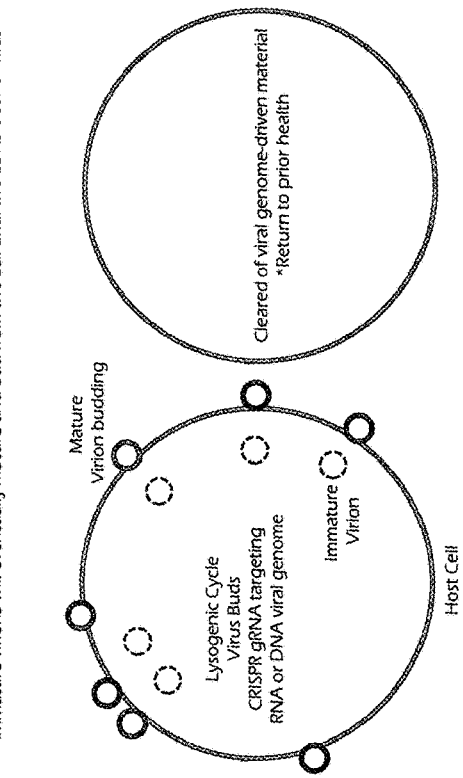
FIGURE 2A
FIGURE 2B

| Taxonomic group | Cas effector | NCBI Accession | Coordinates | Repeat length | # spacers | Spacers avg. length |
|---|---|---|---|---|---|---|
| ARMAN-1 | Cas9 | MOEG01000017 | 1827..7130 | 36 | 271 | 34.5 |
| ARMAN-4 | Cas9 | KY040241 | 11779..14900 | 36 | 1 | 36 |
| Deltaproteobacteria | CasX | MGPG01000094 | 4319..9866 | 37 | 5 | 33.6 |
| Planctomycetes | CasX | MHYZ01000150 | 1..5586 | 37 | 7 | 32.3 |
| Candidatus Katanobacteria | CasY.1 | MOEH01000029 | 459..5716 | 26 | 14 | 17.1 |
| Candidatus Vogelbacteria | CasY.2 | MOEJ01000028 | 7322..13087 | 26 | 18 | 17.3 |
| Candidatus Vogelbacteria | CasY.3 | MOEK01000006 | 1..4657 | 26 | 12 | 17.3 |
| Candidatus Parcubacteria | CasY.4 | KY040242 | 1..5193 | 25 | 13 | 18.4 |
| Candidatus Komeilibacteria | CasY.5 | MOEI01000022 | 2802..7242 | 36 | 8 | 26 |
| Candidatus Kerfeldbacteria | CasY.6 | MHKD01000036 | 11503..15366 | NA | NA | NA |

FIGURE 4

SEQUENCE LISTING

<160> NUMBER OF SEQ ID NOS: 249

<210> SEQ ID NO 1
<211> LENGTH: 31
<212> TYPE: DNA
<213> ORGANISM: JC virus

<400> SEQUENCE: 1
aaatgcaaag aactccaccc tgatgaaggt g                            31

<210> SEQ ID NO 2
<211> LENGTH: 34
<212> TYPE: DNA
<213> ORGANISM: JC virus

<400> SEQUENCE: 2
aaatgcaaag aactccaccc tgatgaaggt gggg                         34

<210> SEQ ID NO 3
<211> LENGTH: 31
<212> TYPE: DNA
<213> ORGANISM: JC virus

<400> SEQUENCE: 3
cacctttatc agggtggagt tctttgcatt t                            31

<210> SEQ ID NO 4
<211> LENGTH: 34
<212> TYPE: DNA
<213> ORGANISM: JC virus

<400> SEQUENCE: 4
ccccaccttt atcagggtgg agttctttgc attt                         34

<210> SEQ ID NO 5
<211> LENGTH: 40
<212> TYPE: DNA
<213> ORGANISM: JC virus

<400> SEQUENCE: 5
gatgaatggg aatcctggtg gaatacattt aatgagaagt                   40

<210> SEQ ID NO 6
<211> LENGTH: 43
<212> TYPE: DNA
<213> ORGANISM: JC virus

<400> SEQUENCE: 6
gatgaatggg aatcctggtg gaatacattt aatgagaagt ggg               43

<210> SEQ ID NO 7
<211> LENGTH: 40
<212> TYPE: DNA
<213> ORGANISM: JC virus

<400> SEQUENCE: 7
acttctcatt aaatgtattc caccaggatt cccattcatc                   40

<210> SEQ ID NO 8
<211> LENGTH: 43
<212> TYPE: DNA
<213> ORGANISM: JC virus

<400> SEQUENCE: 8
cccacttctc attaaatgta ttccaccagg attcccattc atc         43

<210> SEQ ID NO 9
<211> LENGTH: 33
<212> TYPE: DNA
<213> ORGANISM: JC virus

<400> SEQUENCE: 9
aaggtactgg ctattcaagg ggccaataga cag         33

<210> SEQ ID NO 10
<211> LENGTH: 36
<212> TYPE: DNA
<213> ORGANISM: JC virus

<400> SEQUENCE: 10
aaggtactgg ctattcaagg ggccaataga cagtgg         36

<210> SEQ ID NO 11
<211> LENGTH: 33
<212> TYPE: DNA
<213> ORGANISM: JC virus

<400> SEQUENCE: 11
ctgtctattg gccccttgaa tagccagtac ctt         33

<210> SEQ ID NO 12
<211> LENGTH: 36
<212> TYPE: DNA
<213> ORGANISM: JC virus

<400> SEQUENCE: 12
ccactgtcta ttggcccctt gaatagccag tacctt         36

<210> SEQ ID NO 13
<211> LENGTH: 2550
<212> TYPE: DNA
<213> ORGANISM: JC virus

<400> SEQUENCE: 13
cagctttact taacagttgc agttattttg ggggagggggt cttggttttt ttgaaacatt     60
gaaagccttt acagatgtga aaagtgcagt tttcctgtgt gtctgcacca gaggcttctg    120
agacctggga aaagcattgt gattgtgatt cagtgcttga tccatgtcca gagtcttctg    180
cttcagaatc ttcctctcta ggaaagtcaa gaatgggtct ccccatacca acattagctt    240
tcatagtaga aaatgtatac atgcttattt ctaaatccag cctttctttc cactgcacaa    300
tcctctcatg aatggcagct gcaaagtcag caactggcct aaaccagatt aaaagcaaaa    360
gcaaagtcat accactttgc aaaatccttt tttctagcaa atactcagag cagcttagtg    420
attttctcag gtaggccttt ggtctaaaat ctatctgcct tacaaatctg gcctgtaaag    480
ttctaggcac tgaatattca ttcatggtta caattccagg tggaaacacc tgtgttcttt    540
tgttttggtg ttttctctct aaattaactt ttacacttcc atctaagtaa tctcttaagc    600
aatcaaggtt gcttatgcca tgccctgaag gtaaatccct tgactctgca ccagtgcctt    660
ttacatcctc aaatacaacc ataaactgat ctatacccac tcctaattca agtttaatc     720
tttctaatgg catattaaca tttaatgact tccccccaca gagatcaagt aaagctgcag    780
ctaaagtagt tttgccactg tctattggcc ccttgaatag ccagtacctt tttttttggaa   840

```
tgtttaatac aatgcatttt agaaagtcat aaataacagt gtccatttga ggcagcaagc    900
aatgaatcca ggccacccca gccatatatt gctctaaaac agcattgcca tgtgccccaa    960
aaattaagtc cattttatca agcaagaaat taaaccttc aactaacatt tcttctctgg   1020
tcatgtggat gctgtcaacc ctttgtttgg ctgctacagt atcaacagcc tgctggcaaa   1080
tgcttttttg attttgcta tctgcaaaaa tttgggcatt ataatagtgt tttcatgat    1140
ggttaaagtg atttggctga tccttttttt cacatttttt gcattgctgt gggttttcct   1200
gaaagtctaa gtacatgccc ataagcaaaa aaacatcctc acacttggtt tccaaggcat   1260
actgtgtaac taatttccat gaaacctgct tagtttcttc tggttcttct gggttaaagt   1320
catgctcctt aaggccccc tgaatacttt cttccactac tgcatatggc tgtctacaca    1380
gggcactata aaacaagtat tccttattca cacctttaca aattaaaaaa ctaaaggtac   1440
atagtttttg acagtagtta ttaattgctg acactctatg tctatgtggt gttaagaaaa   1500
acaaaatatt atgaccccca aaaccatgtc tacttataaa agttacagaa tattttcca    1560
taagttttct atataaaatt tgagcttttt ctttagtggt atacacagca aaagaagcaa   1620
cagttctatt actaaacaca gcttgactga ggaatgcatg cagatctaca ggaaagtctt   1680
tagggtcttc tacctttttt ttctttttag gtggggtaga gtgttgggat cctgtgtttt   1740
catcatcact ggcaaacatt tcttcatggc aaaacaggtc ttcatcccac ttctcattaa   1800
atgtattcca ccaggattcc cattcatctg ttccataggt tggcacctaa aaaaaaacaa   1860
ttaagtttat tgtaaaaaac aaaatgccct gcaaagaaa aatagtggtt taccttaaag    1920
ctttagatcc ctgtagggggg tgtctccaag aactttctcc cagcaatgaa gagcttcttg   1980
ggttaagtca caccaaaacc attgtctgaa gcaatcaaag caatagcaat ctatccacac   2040
aagtgggctg cttcttaaaa attttctgtt tctatgcctt aattttagca tgcacattaa   2100
acagggcaa tgcactgaag gattagtggc acagttaggc cattccttgc aataaagggt    2160
atcagaatta ggaggaaaat cacaaccaac ctctgaacta ttccatgtac caaaatcagg   2220
ctgatgagca acttttacac cttgttccat tttttatat aaaaaattca ttctcttcat    2280
cttgtcttcg tccccacctt tatcagggtg gagttcttg catttttca gataagcttt     2340
tctcatgaca ggaatgttcc cccatgcaga cctatcaagg cctaataaat ccataagctc   2400
catggattcc tccctattca gcactttgtc catttttagct ttttgcagca aaaaattact   2460
gcaaaaaagg gaaaaacaag ggaatttccc tggcctccta aaaagcctcc acgcccttac   2520
tacttctgag taagcttgga ggcggaggcg                                    2550
```

<210> SEQ ID NO 14
<211> LENGTH: 27
<212> TYPE: DNA
<213> ORGANISM: JC virus

<400> SEQUENCE: 14
ttacttaaca gttgcagtta ttttggg                                         27

<210> SEQ ID NO 15
<211> LENGTH: 27
<212> TYPE: DNA
<213> ORGANISM: JC virus

<400> SEQUENCE: 15
ttattttggg ggagggtct ttggttt                                          27

```
<210> SEQ ID NO 16
<211> LENGTH: 27
<212> TYPE: DNA
<213> ORGANISM: JC virus

<400> SEQUENCE: 16
ttagctttca tagtagaaaa tgtatac                                            27

<210> SEQ ID NO 17
<211> LENGTH: 27
<212> TYPE: DNA
<213> ORGANISM: JC virus

<400> SEQUENCE: 17
ttatttctaa atccagcctt tctttcc                                            27

<210> SEQ ID NO 18
<211> LENGTH: 27
<212> TYPE: DNA
<213> ORGANISM: JC virus

<400> SEQUENCE: 18
ttagtgattt tctcaggtag gcctttg                                            27

<210> SEQ ID NO 19
<211> LENGTH: 27
<212> TYPE: DNA
<213> ORGANISM: JC virus

<400> SEQUENCE: 19
ttacaattcc aggtggaaac acctgtg                                            27

<210> SEQ ID NO 20
<211> LENGTH: 27
<212> TYPE: DNA
<213> ORGANISM: JC virus

<400> SEQUENCE: 20 ttaacttttta cacttccatc taagtaa                                           27

<210> SEQ ID NO 21
<211> LENGTH: 27
<212> TYPE: DNA
<213> ORGANISM: JC virus

<400> SEQUENCE: 21
ttacacttcc atctaagtaa tctctta                                            27

<210> SEQ ID NO 22
<211> LENGTH: 27
<212> TYPE: DNA
<213> ORGANISM: JC virus

<400> SEQUENCE: 22
ttaagcaatc aaggttgctt atgccat                                            27

<210> SEQ ID NO 23
<211> LENGTH: 27
<212> TYPE: DNA
<213> ORGANISM: JC virus

<400> SEQUENCE: 23
ttatgccatg ccctgaaggt aaatccc                                            27
```

```
<210> SEQ ID NO 24
<211> LENGTH: 27
<212> TYPE: DNA
<213> ORGANISM: JC virus

<400> SEQUENCE: 24
ttacatcctc aaatacaacc ataaact                                        27

<210> SEQ ID NO 25
<211> LENGTH: 27
<212> TYPE: DNA
<213> ORGANISM: JC virus

<400> SEQUENCE: 25
ttaatctttc taatggcata ttaacat                                        27

<210> SEQ ID NO 26
<211> LENGTH: 27
<212> TYPE: DNA
<213> ORGANISM: JC virus

<400> SEQUENCE: 26
ttaacattta atgactttcc cccacag                                        27

<210> SEQ ID NO 27
<211> LENGTH: 27
<212> TYPE: DNA
<213> ORGANISM: JC virus

<400> SEQUENCE: 27
ttaatgactt tcccccacag agatcaa                                        27

<210> SEQ ID NO 28
<211> LENGTH: 27
<212> TYPE: DNA
<213> ORGANISM: JC virus

<400> SEQUENCE: 28
ttaatacaat gcattttaga aagtcat                                        27

<210> SEQ ID NO 29
<211> LENGTH: 27
<212> TYPE: DNA
<213> ORGANISM: JC virus

<400> SEQUENCE: 29
ttaagtccat tttatcaagc aagaaat                                        27

<210> SEQ ID NO 30
<211> LENGTH: 27
<212> TYPE: DNA
<213> ORGANISM: JC virus

<400> SEQUENCE: 30
ttatcaagca agaaattaaa cctttca                                        27

<210> SEQ ID NO 31
<211> LENGTH: 27
<212> TYPE: DNA
<213> ORGANISM: JC virus

<400> SEQUENCE: 31
ttaaagtgat ttggctgatc ctttttt                                        27
```

```
<210> SEQ ID NO 32
<211> LENGTH: 27
<212> TYPE: DNA
<213> ORGANISM: JC virus

<400> SEQUENCE: 32
ttaaagtcat gctccttaag gcccccc                                        27

<210> SEQ ID NO 33
<211> LENGTH: 27
<212> TYPE: DNA
<213> ORGANISM: JC virus

<400> SEQUENCE: 33
ttattcacac ctttacaaat taaaaaa                                        27

<210> SEQ ID NO 34
<211> LENGTH: 27
<212> TYPE: DNA
<213> ORGANISM: JC virus

<400> SEQUENCE: 34
ttacaaatta aaaactaaa ggtacat                                         27

<210> SEQ ID NO 35
<211> LENGTH: 27
<212> TYPE: DNA
<213> ORGANISM: JC virus

<400> SEQUENCE: 35
ttaaaaaact aaaggtacat agttttt                                        27

<210> SEQ ID NO 36
<211> LENGTH: 27
<212> TYPE: DNA
<213> ORGANISM: JC virus

<400> SEQUENCE: 36
ttattaattg ctgacactct atgtcta                                        27

<210> SEQ ID NO 37
<211> LENGTH: 27
<212> TYPE: DNA
<213> ORGANISM: JC virus

<400> SEQUENCE: 37
ttaattgctg acactctatg tctatgt                                        27

<210> SEQ ID NO 38
<211> LENGTH: 27
<212> TYPE: DNA
<213> ORGANISM: JC virus

<400> SEQUENCE: 38
ttaagaaaaa caaatatta tgacccc                                         27

<210> SEQ ID NO 39
<211> LENGTH: 27
<212> TYPE: DNA
<213> ORGANISM: JC virus

<400> SEQUENCE: 39
```
ttataaaagt tacagaatat ttttcca                                27

<210> SEQ ID NO 40
<211> LENGTH: 27
<212> TYPE: DNA
<213> ORGANISM: JC virus

<400> SEQUENCE: 40
ttacagaata tttttccata agtttct                                27

<210> SEQ ID NO 41
<211> LENGTH: 27
<212> TYPE: DNA
<213> ORGANISM: JC virus

<400> SEQUENCE: 41
ttagtggtat acacagcaaa agaagca                                27

<210> SEQ ID NO 42
<211> LENGTH: 27
<212> TYPE: DNA
<213> ORGANISM: JC virus

<400> SEQUENCE: 42
ttaggtgggg tagagtgttg ggatcct                                27

<210> SEQ ID NO 43
<211> LENGTH: 27
<212> TYPE: DNA
<213> ORGANISM: JC virus

<400> SEQUENCE: 43
ttaaatgtat tccaccagga ttcccat                                27

<210> SEQ ID NO 44
<211> LENGTH: 27
<212> TYPE: DNA
<213> ORGANISM: JC virus

<400> SEQUENCE: 44
ttaagtttat tgtaaaaaac aaaatgc                                27

<210> SEQ ID NO 45
<211> LENGTH: 27
<212> TYPE: DNA
<213> ORGANISM: JC virus

<400> SEQUENCE: 45
ttattgtaaa aacaaaatg ccctgca                                 27

<210> SEQ ID NO 46
<211> LENGTH: 27
<212> TYPE: DNA
<213> ORGANISM: JC virus

<400> SEQUENCE: 46
ttaaagcttt agatccctgt aggggt                                 27

<210> SEQ ID NO 47
<211> LENGTH: 27
<212> TYPE: DNA
<213> ORGANISM: JC virus

<400> SEQUENCE: 47
ttaagtcaca cccaaaccat tgtctga        27

<210> SEQ ID NO 48
<211> LENGTH: 27
<212> TYPE: DNA
<213> ORGANISM: JC virus

<400> SEQUENCE: 48
ttaaaaattt tctgtttcta tgcctta        27

<210> SEQ ID NO 49
<211> LENGTH: 27
<212> TYPE: DNA
<213> ORGANISM: JC virus

<400> SEQUENCE: 49
ttagcatgca cattaaacag gggcaat        27

<210> SEQ ID NO 50
<211> LENGTH: 27
<212> TYPE: DNA
<213> ORGANISM: JC virus

<400> SEQUENCE: 50
ttaaacaggg gcaatgcact gaaggat        27

<210> SEQ ID NO 51
<211> LENGTH: 27
<212> TYPE: DNA
<213> ORGANISM: JC virus

<400> SEQUENCE: 51
ttagtggcac agttaggcca ttccttg        27

<210> SEQ ID NO 52
<211> LENGTH: 27
<212> TYPE: DNA
<213> ORGANISM: JC virus

<400> SEQUENCE: 52
ttaggccatt ccttgcaata aagggta        27

<210> SEQ ID NO 53
<211> LENGTH: 27
<212> TYPE: DNA
<213> ORGANISM: JC virus

<400> SEQUENCE: 53
ttaggaggaa aatcacaacc aacctct        27

<210> SEQ ID NO 54
<211> LENGTH: 27
<212> TYPE: DNA
<213> ORGANISM: JC virus

<400> SEQUENCE: 54
ttacaccttg ttccattttt ttatata        27

<210> SEQ ID NO 55
<211> LENGTH: 27
<212> TYPE: DNA
<213> ORGANISM: JC virus

<400> SEQUENCE: 55
ttatataaaa aattcattct cttcatc                    27

<210> SEQ ID NO 56
<211> LENGTH: 27
<212> TYPE: DNA
<213> ORGANISM: JC virus

<400> SEQUENCE: 56 ttagctttt gcagcaaaaa attactg                     27

<210> SEQ ID NO 57
<211> LENGTH: 27
<212> TYPE: DNA
<213> ORGANISM: JC virus

<400> SEQUENCE: 57
ttactgcaaa aagggaaaa acaaggg                     27

<210> SEQ ID NO 58
<211> LENGTH: 27
<212> TYPE: DNA
<213> ORGANISM: JC virus

<400> SEQUENCE: 58
ttactacttc tgagtaagct tggaggc                    27

<210> SEQ ID NO 59
<211> LENGTH: 27
<212> TYPE: DNA
<213> ORGANISM: JC virus

<400> SEQUENCE: 59
tttacttaac agttgcagtt attttgg                    27

<210> SEQ ID NO 60
<211> LENGTH: 27
<212> TYPE: DNA
<213> ORGANISM: JC virus

<400> SEQUENCE: 60
ttttggggga gggtctttg gttttttt                    27

<210> SEQ ID NO 61
<211> LENGTH: 27
<212> TYPE: DNA
<213> ORGANISM: JC virus

<400> SEQUENCE: 61
tttggttttt tgaaacattg aaagcct                    27

<210> SEQ ID NO 62
<211> LENGTH: 27
<212> TYPE: DNA
<213> ORGANISM: JC virus

<400> SEQUENCE: 62 tttttttgaaa cattgaaagc ctttaca                   27

<210> SEQ ID NO 63
<211> LENGTH: 27
<212> TYPE: DNA
<213> ORGANISM: JC virus

-continued

```
<400> SEQUENCE: 63
tttcctgtgt gtctgcacca gaggctt                                27

<210> SEQ ID NO 64
<211> LENGTH: 27
<212> TYPE: DNA
<213> ORGANISM: JC virus

<400> SEQUENCE: 64
tttcatagta gaaaatgtat acatgct                                27

<210> SEQ ID NO 65
<211> LENGTH: 27
<212> TYPE: DNA
<213> ORGANISM: JC virus

<400> SEQUENCE: 65
tttctaaatc cagcctttct ttccact                                27

<210> SEQ ID NO 66
<211> LENGTH: 27
<212> TYPE: DNA
<213> ORGANISM: JC virus

<400> SEQUENCE: 66 tttcttttcca ctgcacaatc ctctcat                               27

<210> SEQ ID NO 67
<211> LENGTH: 27
<212> TYPE: DNA
<213> ORGANISM: JC virus

<400> SEQUENCE: 67
tttccactgc acaatcctct catgaat                                27

<210> SEQ ID NO 68
<211> LENGTH: 27
<212> TYPE: DNA
<213> ORGANISM: JC virus

<400> SEQUENCE: 68
tttgcaaaat ccttttttct agcaaat                                27

<210> SEQ ID NO 69
<211> LENGTH: 27
<212> TYPE: DNA
<213> ORGANISM: JC virus

<400> SEQUENCE: 69 tttttttctag caaatactca gagcagc                               27

<210> SEQ ID NO 70
<211> LENGTH: 27
<212> TYPE: DNA
<213> ORGANISM: JC virus

<400> SEQUENCE: 70
tttctagcaa atactcagag cagctta                                27

<210> SEQ ID NO 71
<211> LENGTH: 27
<212> TYPE: DNA
```

```
<213> ORGANISM: JC virus

<400> SEQUENCE: 71
ttttctcagg taggcctttg gtctaaa                                27

<210> SEQ ID NO 72
<211> LENGTH: 27
<212> TYPE: DNA
<213> ORGANISM: JC virus

<400> SEQUENCE: 72
tttggtctaa aatctatctg ccttaca                                27

<210> SEQ ID NO 73
<211> LENGTH: 27
<212> TYPE: DNA
<213> ORGANISM: JC virus

<400> SEQUENCE: 73
ttttgttttg gtgttttctc tctaaat                                27

<210> SEQ ID NO 74
<211> LENGTH: 27
<212> TYPE: DNA
<213> ORGANISM: JC virus

<400> SEQUENCE: 74
ttttctctct aaattaactt ttacact                                27

<210> SEQ ID NO 75
<211> LENGTH: 27
<212> TYPE: DNA
<213> ORGANISM: JC virus

<400> SEQUENCE: 75
ttttacatcc tcaaatacaa ccataaa                                27

<210> SEQ ID NO 76
<211> LENGTH: 27
<212> TYPE: DNA
<213> ORGANISM: JC virus

<400> SEQUENCE: 76
tttaatcttt ctaatggcat attaaca                                27

<210> SEQ ID NO 77
<211> LENGTH: 27
<212> TYPE: DNA
<213> ORGANISM: JC virus

<400> SEQUENCE: 77
tttctaatgg catattaaca tttaatg                                27

<210> SEQ ID NO 78
<211> LENGTH: 27
<212> TYPE: DNA
<213> ORGANISM: JC virus

<400> SEQUENCE: 78
tttaatgact ttcccccaca gagatca                                27

<210> SEQ ID NO 79
<211> LENGTH: 27
```

```
<212> TYPE: DNA
<213> ORGANISM: JC virus

<400> SEQUENCE: 79
tttgccactg tctattggcc ccttgaa                                          27

<210> SEQ ID NO 80
<211> LENGTH: 27
<212> TYPE: DNA
<213> ORGANISM: JC virus

<400> SEQUENCE: 80 tttttttggaa tgtttaatac aatgcat                                         27

<210> SEQ ID NO 81
<211> LENGTH: 27
<212> TYPE: DNA
<213> ORGANISM: JC virus

<400> SEQUENCE: 81
tttttggaat gtttaataca atgcatt                                          27

<210> SEQ ID NO 82
<211> LENGTH: 27
<212> TYPE: DNA
<213> ORGANISM: JC virus

<400> SEQUENCE: 82
ttttggaatg tttaatacaa tgcattt                                          27

<210> SEQ ID NO 83
<211> LENGTH: 27
<212> TYPE: DNA
<213> ORGANISM: JC virus

<400> SEQUENCE: 83
tttaatacaa tgcattttag aaagtca                                          27

<210> SEQ ID NO 84
<211> LENGTH: 27
<212> TYPE: DNA
<213> ORGANISM: JC virus

<400> SEQUENCE: 84
ttttagaaag tcataaataa cagtgtc                                          27

<210> SEQ ID NO 85
<211> LENGTH: 27
<212> TYPE: DNA
<213> ORGANISM: JC virus

<400> SEQUENCE: 85
tttgaggcag caagcaatga atccagg                                          27

<210> SEQ ID NO 86
<211> LENGTH: 27
<212> TYPE: DNA
<213> ORGANISM: JC virus

<400> SEQUENCE: 86
ttttatcaag caagaaatta aacctttt                                         27

<210> SEQ ID NO 87
```

```
<211> LENGTH: 27
<212> TYPE: DNA
<213> ORGANISM: JC virus

<400> SEQUENCE: 87
tttatcaagc aagaaattaa acctttc                                27

<210> SEQ ID NO 88
<211> LENGTH: 27
<212> TYPE: DNA
<213> ORGANISM: JC virus

<400> SEQUENCE: 88
tttcaactaa catttcttct ctggtca                                27

<210> SEQ ID NO 89
<211> LENGTH: 27
<212> TYPE: DNA
<213> ORGANISM: JC virus

<400> SEQUENCE: 89
tttgtttggc tgctacagta tcaacag                                27

<210> SEQ ID NO 90
<211> LENGTH: 27
<212> TYPE: DNA
<213> ORGANISM: JC virus

<400> SEQUENCE: 90
tttggctgct acagtatcaa cagcctg                                27

<210> SEQ ID NO 91
<211> LENGTH: 27
<212> TYPE: DNA
<213> ORGANISM: JC virus

<400> SEQUENCE: 91 tttttttgatt tttgctatct gcaaaaa                               27

<210> SEQ ID NO 92
<211> LENGTH: 27
<212> TYPE: DNA
<213> ORGANISM: JC virus

<400> SEQUENCE: 92
tttttgattt tgctatctg caaaaat                                 27

<210> SEQ ID NO 93
<211> LENGTH: 27
<212> TYPE: DNA
<213> ORGANISM: JC virus

<400> SEQUENCE: 93 ttttgattt tgctatctgc aaaaatt                                 27

<210> SEQ ID NO 94
<211> LENGTH: 27
<212> TYPE: DNA
<213> ORGANISM: JC virus

<400> SEQUENCE: 94
tttgattttt gctatctgca aaaattt                                27
```

```
<210> SEQ ID NO 95
<211> LENGTH: 27
<212> TYPE: DNA
<213> ORGANISM: JC virus

<400> SEQUENCE: 95
tttttgctat ctgcaaaaat ttgggca                                          27

<210> SEQ ID NO 96
<211> LENGTH: 27
<212> TYPE: DNA
<213> ORGANISM: JC virus

<400> SEQUENCE: 96
tttgctatct gcaaaatttt gggcatt                                          27

<210> SEQ ID NO 97
<211> LENGTH: 27
<212> TYPE: DNA
<213> ORGANISM: JC virus

<400> SEQUENCE: 97
tttgggcatt ataatagtgt ttttcat                                          27

<210> SEQ ID NO 98
<211> LENGTH: 27
<212> TYPE: DNA
<213> ORGANISM: JC virus

<400> SEQUENCE: 98
ttttcatgat ggttaaagtg atttggc                                          27

<210> SEQ ID NO 99
<211> LENGTH: 27
<212> TYPE: DNA
<213> ORGANISM: JC virus

<400> SEQUENCE: 99
tttggctgat ccttttttc acatttt                                           27

<210> SEQ ID NO 100
<211> LENGTH: 27
<212> TYPE: DNA
<213> ORGANISM: JC virus

<400> SEQUENCE: 100
tttttttcac attttttgca ttgctgt                                          27

<210> SEQ ID NO 101
<211> LENGTH: 27
<212> TYPE: DNA
<213> ORGANISM: JC virus

<400> SEQUENCE: 101
ttttttcaca ttttttgcat tgctgtg                                          27

<210> SEQ ID NO 102
<211> LENGTH: 27
<212> TYPE: DNA
<213> ORGANISM: JC virus

<400> SEQUENCE: 102
tttttcacat ttttgcatt gctgtgg                                           27
```

<210> SEQ ID NO 103
<211> LENGTH: 27
<212> TYPE: DNA
<213> ORGANISM: JC virus

<400> SEQUENCE: 103
tttttcacat tttttgcatt gctgtgg                                              27

<210> SEQ ID NO 104
<211> LENGTH: 27
<212> TYPE: DNA
<213> ORGANISM: JC virus

<400> SEQUENCE: 104
ttttcacatt ttttgcattg ctgtggg                                              27

<210> SEQ ID NO 105
<211> LENGTH: 27
<212> TYPE: DNA
<213> ORGANISM: JC virus

<400> SEQUENCE: 105
tttcacattt tttgcattgc tgtgggt                                              27

<210> SEQ ID NO 106
<211> LENGTH: 27
<212> TYPE: DNA
<213> ORGANISM: JC virus

<400> SEQUENCE: 106 tttttttgcat tgctgtgggt tttcctg                                             27

<210> SEQ ID NO 107
<211> LENGTH: 27
<212> TYPE: DNA
<213> ORGANISM: JC virus

<400> SEQUENCE: 107
tttttgcatt gctgtgggtt ttcctga                                              27

<210> SEQ ID NO 108
<211> LENGTH: 27
<212> TYPE: DNA
<213> ORGANISM: JC virus

<400> SEQUENCE: 108
ttttgcattg ctgtgggttt tcctgaa                                              27

<210> SEQ ID NO 109
<211> LENGTH: 27
<212> TYPE: DNA
<213> ORGANISM: JC virus

<400> SEQUENCE: 109
tttgcattgc tgtgggtttt cctgaaa                                              27

<210> SEQ ID NO 110
<211> LENGTH: 27
<212> TYPE: DNA
<213> ORGANISM: JC virus

<400> SEQUENCE: 110
tttccatgaa acctgcttag tttcttc                                              27

<210> SEQ ID NO 111
<211> LENGTH: 27
<212> TYPE: DNA
<213> ORGANISM: JC virus

<400> SEQUENCE: 111
tttcttctgg ttcttctggg ttaaagt                                27

<210> SEQ ID NO 112
<211> LENGTH: 27
<212> TYPE: DNA
<213> ORGANISM: JC virus

<400> SEQUENCE: 112
tttcttccac tactgcatat ggctgtc                                27

<210> SEQ ID NO 113
<211> LENGTH: 27
<212> TYPE: DNA
<213> ORGANISM: JC virus

<400> SEQUENCE: 113
tttacaaatt aaaaaactaa aggtaca                                27

<210> SEQ ID NO 114
<211> LENGTH: 27
<212> TYPE: DNA
<213> ORGANISM: JC virus

<400> SEQUENCE: 114
tttttgacag tagttattaa ttgctga                                27

<210> SEQ ID NO 115
<211> LENGTH: 27
<212> TYPE: DNA
<213> ORGANISM: JC virus

<400> SEQUENCE: 115
ttttgacagt agttattaat tgctgac                                27

<210> SEQ ID NO 116
<211> LENGTH: 27
<212> TYPE: DNA
<213> ORGANISM: JC virus

<400> SEQUENCE: 116
tttgacagta gttattaatt gctgaca                                27

<210> SEQ ID NO 117
<211> LENGTH: 27
<212> TYPE: DNA
<213> ORGANISM: JC virus

<400> SEQUENCE: 117
tttttccata agtttcttat ataaaat                                27

<210> SEQ ID NO 118
<211> LENGTH: 27
<212> TYPE: DNA
<213> ORGANISM: JC virus

<400> SEQUENCE: 118

-continued ttttccataa gtttcttata taaaatt                                          27

<210> SEQ ID NO 119
<211> LENGTH: 27
<212> TYPE: DNA
<213> ORGANISM: JC virus

<400> SEQUENCE: 119
tttccataag tttcttatat aaaattt                                          27

<210> SEQ ID NO 120
<211> LENGTH: 27
<212> TYPE: DNA
<213> ORGANISM: JC virus

<400> SEQUENCE: 120
tttcttatat aaaatttgag cttttc                                          27

<210> SEQ ID NO 121
<211> LENGTH: 27
<212> TYPE: DNA
<213> ORGANISM: JC virus

<400> SEQUENCE: 121
tttttcttta gtggtataca cagcaaa                                          27

<210> SEQ ID NO 122
<211> LENGTH: 27
<212> TYPE: DNA
<213> ORGANISM: JC virus

<400> SEQUENCE: 122
ttttctttag tggtatacac agcaaaa                                          27

<210> SEQ ID NO 123
<211> LENGTH: 27
<212> TYPE: DNA
<213> ORGANISM: JC virus

<400> SEQUENCE: 123
tttctttagt ggtatacaca gcaaaag                                          27

<210> SEQ ID NO 124
<211> LENGTH: 27
<212> TYPE: DNA
<213> ORGANISM: JC virus

<400> SEQUENCE: 124
tttagtggta tacacagcaa aagaagc                                          27

<210> SEQ ID NO 125
<211> LENGTH: 27
<212> TYPE: DNA
<213> ORGANISM: JC virus

<400> SEQUENCE: 125
tttagggtct tctaccttt ttttcttt                                          27

<210> SEQ ID NO 126
<211> LENGTH: 27
<212> TYPE: DNA
<213> ORGANISM: JC virus

<400> SEQUENCE: 126

```
tttttttttct ttttaggtgg ggtagag                                              27

<210> SEQ ID NO 127
<211> LENGTH: 27
<212> TYPE: DNA
<213> ORGANISM: JC virus

<400> SEQUENCE: 127
tttttttctt tttaggtggg gtagagt                                               27

<210> SEQ ID NO 128
<211> LENGTH: 27
<212> TYPE: DNA
<213> ORGANISM: JC virus

<400> SEQUENCE: 128 tttttttcttt ttaggtgggg tagagtg                                              27

<210> SEQ ID NO 129
<211> LENGTH: 27
<212> TYPE: DNA
<213> ORGANISM: JC virus

<400> SEQUENCE: 129 tttttcttt taggtggggt agagtgt                                                27

<210> SEQ ID NO 130
<211> LENGTH: 27
<212> TYPE: DNA
<213> ORGANISM: JC virus

<400> SEQUENCE: 130
ttttcttttt aggtggggta gagtgtt                                               27

<210> SEQ ID NO 131
<211> LENGTH: 27
<212> TYPE: DNA
<213> ORGANISM: JC virus

<400> SEQUENCE: 131 tttctttta ggtggggtag agtgttg                                                27

<210> SEQ ID NO 132
<211> LENGTH: 27
<212> TYPE: DNA
<213> ORGANISM: JC virus

<400> SEQUENCE: 132
ttttcatcat cactggcaaa catttct                                               27

<210> SEQ ID NO 133
<211> LENGTH: 27
<212> TYPE: DNA
<213> ORGANISM: JC virus

<400> SEQUENCE: 133
tttcatcatc actggcaaac atttctt                                               27

<210> SEQ ID NO 134
<211> LENGTH: 27
<212> TYPE: DNA
<213> ORGANISM: JC virus
```

```
<400> SEQUENCE: 134
tttattgtaa aaacaaaat gccctgc                                        27

<210> SEQ ID NO 135
<211> LENGTH: 27
<212> TYPE: DNA
<213> ORGANISM: JC virus

<400> SEQUENCE: 135
tttagatccc tgtaggggt gtctcca                                        27

<210> SEQ ID NO 136
<211> LENGTH: 27
<212> TYPE: DNA
<213> ORGANISM: JC virus

<400> SEQUENCE: 136
tttctcccag caatgaagag cttcttg                                       27

<210> SEQ ID NO 137
<211> LENGTH: 27
<212> TYPE: DNA
<213> ORGANISM: JC virus

<400> SEQUENCE: 137
ttttctgttt ctatgcctta attttag                                       27

<210> SEQ ID NO 138
<211> LENGTH: 27
<212> TYPE: DNA
<213> ORGANISM: JC virus

<400> SEQUENCE: 138
ttttagcatg cacattaaac agggggca                                      27

<210> SEQ ID NO 139
<211> LENGTH: 27
<212> TYPE: DNA
<213> ORGANISM: JC virus

<400> SEQUENCE: 139
ttttacacct tgttccattt ttttata                                       27

<210> SEQ ID NO 140
<211> LENGTH: 27
<212> TYPE: DNA
<213> ORGANISM: JC virus

<400> SEQUENCE: 140
tttacacctt gttccatttt tttatat                                       27

<210> SEQ ID NO 141
<211> LENGTH: 27
<212> TYPE: DNA
<213> ORGANISM: JC virus

<400> SEQUENCE: 141 tttttttatat aaaaaattca ttctctt                                      27

<210> SEQ ID NO 142
<211> LENGTH: 27
<212> TYPE: DNA
<213> ORGANISM: JC virus
```

<400> SEQUENCE: 142 tttgcattttt tcagataag cttttct                              27

<210> SEQ ID NO 143
<211> LENGTH: 27
<212> TYPE: DNA
<213> ORGANISM: JC virus

<400> SEQUENCE: 143 tttttttcaga taagcttttc tcatgac                             27

<210> SEQ ID NO 144
<211> LENGTH: 27
<212> TYPE: DNA
<213> ORGANISM: JC virus

<400> SEQUENCE: 144
tttttcagat aagcttttct catgaca                              27

<210> SEQ ID NO 145
<211> LENGTH: 27
<212> TYPE: DNA
<213> ORGANISM: JC virus

<400> SEQUENCE: 145
ttttcagata agcttttctc atgacag                              27

<210> SEQ ID NO 146
<211> LENGTH: 27
<212> TYPE: DNA
<213> ORGANISM: JC virus

<400> SEQUENCE: 146
tttcagataa gcttttctca tgacagg                              27

<210> SEQ ID NO 147
<211> LENGTH: 27
<212> TYPE: DNA
<213> ORGANISM: JC virus

<400> SEQUENCE: 147
ttttctcatg acaggaatgt tcccca                               27

<210> SEQ ID NO 148
<211> LENGTH: 27
<212> TYPE: DNA
<213> ORGANISM: JC virus

<400> SEQUENCE: 148
tttgtccatt ttagcttttt gcagcaa                              27

<210> SEQ ID NO 149
<211> LENGTH: 27
<212> TYPE: DNA
<213> ORGANISM: JC virus

<400> SEQUENCE: 149
ttttagcttt ttgcagcaaa aaattac                              27

<210> SEQ ID NO 150
<211> LENGTH: 27
<212> TYPE: DNA

```
<213> ORGANISM: JC virus

<400> SEQUENCE: 150
tttagctttt tgcagcaaaa aattact                                    27

<210> SEQ ID NO 151
<211> LENGTH: 27
<212> TYPE: DNA
<213> ORGANISM: JC virus

<400> SEQUENCE: 151
ttttgcagca aaaattact gcaaaaa                                     27

<210> SEQ ID NO 152
<211> LENGTH: 27
<212> TYPE: DNA
<213> ORGANISM: JC virus

<400> SEQUENCE: 152
tttgcagcaa aaattactg caaaaaa                                     27

<210> SEQ ID NO 153
<211> LENGTH: 27
<212> TYPE: DNA
<213> ORGANISM: JC virus

<400> SEQUENCE: 153
tttccctggc tcctaaaaa gcctcca                                     27

<210> SEQ ID NO 154
<211> LENGTH: 27
<212> TYPE: DNA
<213> ORGANISM: JC virus

<400> SEQUENCE: 154
ttcctgtgtg tctgcaccag aggcttc                                    27

<210> SEQ ID NO 155
<211> LENGTH: 27
<212> TYPE: DNA
<213> ORGANISM: JC virus

<400> SEQUENCE: 155
ttctgagacc tgggaaaagc attgtga                                    27

<210> SEQ ID NO 156
<211> LENGTH: 27
<212> TYPE: DNA
<213> ORGANISM: JC virus

<400> SEQUENCE: 156
ttctgcttca gaatcttcct ctctagg                                    27

<210> SEQ ID NO 157
<211> LENGTH: 27
<212> TYPE: DNA
<213> ORGANISM: JC virus

<400> SEQUENCE: 157
ttcagaatct tcctctctag gaaagtc                                    27

<210> SEQ ID NO 158
<211> LENGTH: 27
```

<212> TYPE: DNA
<213> ORGANISM: JC virus

<400> SEQUENCE: 158
ttcctctcta ggaaagtcaa gaatggg 27

<210> SEQ ID NO 159
<211> LENGTH: 27
<212> TYPE: DNA
<213> ORGANISM: JC virus

<400> SEQUENCE: 159
ttctttccac tgcacaatcc tctcatg 27

<210> SEQ ID NO 160
<211> LENGTH: 27
<212> TYPE: DNA
<213> ORGANISM: JC virus

<400> SEQUENCE: 160
ttctagcaaa tactcagagc agcttag 27

<210> SEQ ID NO 161
<211> LENGTH: 27
<212> TYPE: DNA
<213> ORGANISM: JC virus

<400> SEQUENCE: 161
ttctcaggta ggcctttggt ctaaaat 27

<210> SEQ ID NO 162
<211> LENGTH: 27
<212> TYPE: DNA
<213> ORGANISM: JC virus

<400> SEQUENCE: 162
ttctaggcac tgaatattca ttcatgg 27

<210> SEQ ID NO 163
<211> LENGTH: 27
<212> TYPE: DNA
<213> ORGANISM: JC virus

<400> SEQUENCE: 163
ttcattcatg gttacaattc caggtgg 27

<210> SEQ ID NO 164
<211> LENGTH: 27
<212> TYPE: DNA
<213> ORGANISM: JC virus

<400> SEQUENCE: 164
ttcatggtta caattccagg tggaaac 27

<210> SEQ ID NO 165
<211> LENGTH: 27
<212> TYPE: DNA
<213> ORGANISM: JC virus

<400> SEQUENCE: 165
ttccaggtgg aaacacctgt gttcttt 27

<210> SEQ ID NO 166

```
<211> LENGTH: 27
<212> TYPE: DNA
<213> ORGANISM: JC virus

<400> SEQUENCE: 166
ttcttttgtt ttggtgtttt ctctcta                                              27

<210> SEQ ID NO 167
<211> LENGTH: 27
<212> TYPE: DNA
<213> ORGANISM: JC virus

<400> SEQUENCE: 167
ttctctctaa attaactttt acacttc                                              27

<210> SEQ ID NO 168
<211> LENGTH: 27
<212> TYPE: DNA
<213> ORGANISM: JC virus

<400> SEQUENCE: 168
ttccatctaa gtaatctctt aagcaat                                              27

<210> SEQ ID NO 169
<211> LENGTH: 27
<212> TYPE: DNA
<213> ORGANISM: JC virus

<400> SEQUENCE: 169
ttcaaagttt aatctttcta atggcat                                              27

<210> SEQ ID NO 170
<211> LENGTH: 27
<212> TYPE: DNA
<213> ORGANISM: JC virus

<400> SEQUENCE: 170
ttcaaagttt aatctttcta atggcat                                              27

<210> SEQ ID NO 171
<211> LENGTH: 27
<212> TYPE: DNA
<213> ORGANISM: JC virus

<400> SEQUENCE: 171
ttctaatggc atattaacat ttaatga                                              27

<210> SEQ ID NO 172
<211> LENGTH: 27
<212> TYPE: DNA
<213> ORGANISM: JC virus

<400> SEQUENCE: 172
ttcccccaca gagatcaagt aaagctg                                              27

<210> SEQ ID NO 173
<211> LENGTH: 27
<212> TYPE: DNA
<213> ORGANISM: JC virus

<400> SEQUENCE: 173
ttcaactaac atttcttctc tggtcat                                              27
```

-continued

<210> SEQ ID NO 174
<211> LENGTH: 27
<212> TYPE: DNA
<213> ORGANISM: JC virus

<400> SEQUENCE: 174
ttctctggtc atgtggatgc tgtcaac                                27

<210> SEQ ID NO 175
<211> LENGTH: 27
<212> TYPE: DNA
<213> ORGANISM: JC virus

<400> SEQUENCE: 175
ttcatgatgg ttaaagtgat ttggctg                                27

<210> SEQ ID NO 176
<211> LENGTH: 27
<212> TYPE: DNA
<213> ORGANISM: JC virus

<400> SEQUENCE: 176
ttcctgaaag tctaagtaca tgcccat                                27

<210> SEQ ID NO 177
<211> LENGTH: 27
<212> TYPE: DNA
<213> ORGANISM: JC virus

<400> SEQUENCE: 177
ttccatgaaa cctgcttagt ttcttct                                27

<210> SEQ ID NO 178
<211> LENGTH: 27
<212> TYPE: DNA
<213> ORGANISM: JC virus

<400> SEQUENCE: 178
ttcttctggt tcttctgggt taaagtc                                27

<210> SEQ ID NO 179
<211> LENGTH: 27
<212> TYPE: DNA
<213> ORGANISM: JC virus

<400> SEQUENCE: 179
ttctggttct tctggttaa agtcatg                                 27

<210> SEQ ID NO 180
<211> LENGTH: 27
<212> TYPE: DNA
<213> ORGANISM: JC virus

<400> SEQUENCE: 180
ttcttctggg ttaaagtcat gctcctt                                27

<210> SEQ ID NO 181
<211> LENGTH: 26
<212> TYPE: DNA
<213> ORGANISM: JC virus

<400> SEQUENCE: 181
ttctgggtta agtcatgct ccttaa                                  26

<210> SEQ ID NO 182
<211> LENGTH: 27
<212> TYPE: DNA
<213> ORGANISM: JC virus

<400> SEQUENCE: 182
ttccactact gcatatggct gtctaca        27

<210> SEQ ID NO 183
<211> LENGTH: 27
<212> TYPE: DNA
<213> ORGANISM: JC virus

<400> SEQUENCE: 183
ttcacacctt tacaaattaa aaaacta        27

<210> SEQ ID NO 184
<211> LENGTH: 27
<212> TYPE: DNA
<213> ORGANISM: JC virus

<400> SEQUENCE: 184
ttccataagt ttcttatata aaatttg        27

<210> SEQ ID NO 185
<211> LENGTH: 27
<212> TYPE: DNA
<213> ORGANISM: JC virus

<400> SEQUENCE: 185
ttcttatata aaatttgagc tttttct        27

<210> SEQ ID NO 186
<211> LENGTH: 27
<212> TYPE: DNA
<213> ORGANISM: JC virus

<400> SEQUENCE: 186
ttctattact aaacacagct tgactga        27

<210> SEQ ID NO 187
<211> LENGTH: 27
<212> TYPE: DNA
<213> ORGANISM: JC virus

<400> SEQUENCE: 187
ttctaccttt tttttctttt taggtgg        27

<210> SEQ ID NO 188
<211> LENGTH: 27
<212> TYPE: DNA
<213> ORGANISM: JC virus

<400> SEQUENCE: 188
ttctaccttt tttttctttt taggtgg        27

<210> SEQ ID NO 189
<211> LENGTH: 27
<212> TYPE: DNA
<213> ORGANISM: JC virus

<400> SEQUENCE: 189 ttcttttttag gtggggtaga gtgttgg        27

<210> SEQ ID NO 190
<211> LENGTH: 27
<212> TYPE: DNA
<213> ORGANISM: JC virus

<400> SEQUENCE: 190
ttcatcatca ctggcaaaca tttcttc					27

<210> SEQ ID NO 191
<211> LENGTH: 27
<212> TYPE: DNA
<213> ORGANISM: JC virus

<400> SEQUENCE: 191
ttcatcccac ttctcattaa atgtatt					27

<210> SEQ ID NO 192
<211> LENGTH: 27
<212> TYPE: DNA
<213> ORGANISM: JC virus

<400> SEQUENCE: 192
ttccaccagg attcccattc atctgtt					27

<210> SEQ ID NO 193
<211> LENGTH: 26
<212> TYPE: DNA
<213> ORGANISM: JC virus

<400> SEQUENCE: 193
ttccattcat ctgttccata ggttgg					26

<210> SEQ ID NO 194
<211> LENGTH: 27
<212> TYPE: DNA
<213> ORGANISM: JC virus

<400> SEQUENCE: 194
ttcatctgtt ccataggttg gcaccta					27

<210> SEQ ID NO 195
<211> LENGTH: 27
<212> TYPE: DNA
<213> ORGANISM: JC virus

<400> SEQUENCE: 195
ttccataggt tggcacctaa aaaaaaa					27

<210> SEQ ID NO 196
<211> LENGTH: 27
<212> TYPE: DNA
<213> ORGANISM: JC virus

<400> SEQUENCE: 196
ttctcccagc aatgaagagc ttcttgg					27

<210> SEQ ID NO 197
<211> LENGTH: 27
<212> TYPE: DNA
<213> ORGANISM: JC virus

<400> SEQUENCE: 197
ttcttgggtt aagtcacacc caaacca            27

<210> SEQ ID NO 198
<211> LENGTH: 27
<212> TYPE: DNA
<213> ORGANISM: JC virus

<400> SEQUENCE: 198
ttcttaaaaa ttttctgttt ctatgcc            27

<210> SEQ ID NO 199
<211> LENGTH: 27
<212> TYPE: DNA
<213> ORGANISM: JC virus

<400> SEQUENCE: 199
ttctgtttct atgccttaat tttagca            27

<210> SEQ ID NO 200
<211> LENGTH: 27
<212> TYPE: DNA
<213> ORGANISM: JC virus

<400> SEQUENCE: 200
ttccttgcaa taagggtat cagaatt             27

<210> SEQ ID NO 201
<211> LENGTH: 27
<212> TYPE: DNA
<213> ORGANISM: JC virus

<400> SEQUENCE: 201
ttccatgtac caaaatcagg ctgatga            27

<210> SEQ ID NO 202
<211> LENGTH: 27
<212> TYPE: DNA
<213> ORGANISM: JC virus

<400> SEQUENCE: 202
ttccattttt ttatataaaa aattcat            27

<210> SEQ ID NO 203
<211> LENGTH: 27
<212> TYPE: DNA
<213> ORGANISM: JC virus

<400> SEQUENCE: 203
ttcattctct tcatcttgtc ttcgtcc            27

<210> SEQ ID NO 204
<211> LENGTH: 27
<212> TYPE: DNA
<213> ORGANISM: JC virus

<400> SEQUENCE: 204
ttctcttcat cttgtcttcg tccccac            27

<210> SEQ ID NO 205
<211> LENGTH: 27
<212> TYPE: DNA
<213> ORGANISM: JC virus

<400> SEQUENCE: 205
ttcatcttgt cttcgtcccc accttta                                      27

<210> SEQ ID NO 206
<211> LENGTH: 27
<212> TYPE: DNA
<213> ORGANISM: JC virus

<400> SEQUENCE: 206
ttcgtcccca cctttatcag ggtggag                                      27

<210> SEQ ID NO 207
<211> LENGTH: 27
<212> TYPE: DNA
<213> ORGANISM: JC virus

<400> SEQUENCE: 207
ttctttgcat ttttttcagat aagcttt                                     27

<210> SEQ ID NO 208
<211> LENGTH: 27
<212> TYPE: DNA
<213> ORGANISM: JC virus

<400> SEQUENCE: 208
ttcagataag cttttctcat gacagga                                      27

<210> SEQ ID NO 209
<211> LENGTH: 27
<212> TYPE: DNA
<213> ORGANISM: JC virus

<400> SEQUENCE: 209
ttctcatgac aggaatgttc ccccatg                                      27

<210> SEQ ID NO 210
<211> LENGTH: 27
<212> TYPE: DNA
<213> ORGANISM: JC virus

<400> SEQUENCE: 210
ttcccccatg cagacctatc aaggcct                                      27

<210> SEQ ID NO 211
<211> LENGTH: 27
<212> TYPE: DNA
<213> ORGANISM: JC virus

<400> SEQUENCE: 211
ttcctcccta ttcagcactt tgtccat                                      27

<210> SEQ ID NO 212
<211> LENGTH: 27
<212> TYPE: DNA
<213> ORGANISM: JC virus

<400> SEQUENCE: 212
ttcagcactt tgtccatttt agctttt                                      27

<210> SEQ ID NO 213
<211> LENGTH: 27
<212> TYPE: DNA
<213> ORGANISM: JC virus

<400> SEQUENCE: 213
ttccctggcc tcctaaaaag cctccac 27

<210> SEQ ID NO 214
<211> LENGTH: 27
<212> TYPE: DNA
<213> ORGANISM: JC virus

<400> SEQUENCE: 214
ttctgagtaa gcttggaggc ggaggcg 27

<210> SEQ ID NO 215
<211> LENGTH: 27
<212> TYPE: DNA
<213> ORGANISM: JC virus

<400> SEQUENCE: 215
ttgcagttat tttggggag gggtctt 27

<210> SEQ ID NO 216
<211> LENGTH: 27
<212> TYPE: DNA
<213> ORGANISM: JC virus

<400> SEQUENCE: 216
ttgggggagg ggtctttggt tttttga 27

<210> SEQ ID NO 217
<211> LENGTH: 27
<212> TYPE: DNA
<213> ORGANISM: JC virus

<400> SEQUENCE: 217 ttggttttt gaaacattga aagcctt 27

<210> SEQ ID NO 218
<211> LENGTH: 27
<212> TYPE: DNA
<213> ORGANISM: JC virus

<400> SEQUENCE: 218
ttgaaacatt gaaagccttt acagatg 27

<210> SEQ ID NO 219
<211> LENGTH: 27
<212> TYPE: DNA
<213> ORGANISM: JC virus

<400> SEQUENCE: 219
ttgaaagcct ttacagatgt gaaaagt 27

<210> SEQ ID NO 220
<211> LENGTH: 27
<212> TYPE: DNA
<213> ORGANISM: JC virus

<400> SEQUENCE: 220
ttgtgattgt gattcagtgc ttgatcc 27

<210> SEQ ID NO 221
<211> LENGTH: 27
<212> TYPE: DNA
<213> ORGANISM: JC virus

<400> SEQUENCE: 221
ttgtgattca gtgcttgatc catgtcc                                              27

<210> SEQ ID NO 222
<211> LENGTH: 27
<212> TYPE: DNA
<213> ORGANISM: JC virus

<400> SEQUENCE: 222
ttgatccatg tccagagtct tctgctt                                              27

<210> SEQ ID NO 223
<211> LENGTH: 27
<212> TYPE: DNA
<213> ORGANISM: JC virus

<400> SEQUENCE: 223
ttgcaaaatc cttttttcta gcaaata                                              27

<210> SEQ ID NO 224
<211> LENGTH: 27
<212> TYPE: DNA
<213> ORGANISM: JC virus

<400> SEQUENCE: 224
ttggtgtttt ctctctaaat taactttt                                             27

<210> SEQ ID NO 225
<211> LENGTH: 27
<212> TYPE: DNA
<213> ORGANISM: JC virus

<400> SEQUENCE: 225
ttgccactgt ctattggccc cttgaat                                              27

<210> SEQ ID NO 226
<211> LENGTH: 27
<212> TYPE: DNA
<213> ORGANISM: JC virus

<400> SEQUENCE: 226
ttggcccctt gaatagccag taccttt                                              27

<210> SEQ ID NO 227
<211> LENGTH: 27
<212> TYPE: DNA
<213> ORGANISM: JC virus

<400> SEQUENCE: 227
ttgaatagcc agtacctttt ttttgga                                              27

<210> SEQ ID NO 228
<211> LENGTH: 27
<212> TYPE: DNA
<213> ORGANISM: JC virus

<400> SEQUENCE: 228
ttggaatgtt taatacaatg catttta                                              27

<210> SEQ ID NO 229
<211> LENGTH: 27
<212> TYPE: DNA

```
<213> ORGANISM: JC virus

<400> SEQUENCE: 229
ttgaggcagc aagcaatgaa tccaggc                                              27

<210> SEQ ID NO 230
<211> LENGTH: 27
<212> TYPE: DNA
<213> ORGANISM: JC virus

<400> SEQUENCE: 230
ttgccatgtg ccccaaaaat taagtcc                                              27

<210> SEQ ID NO 231
<211> LENGTH: 27
<212> TYPE: DNA
<213> ORGANISM: JC virus

<400> SEQUENCE: 231
ttgtttggct gctacagtat caacagc                                              27

<210> SEQ ID NO 232
<211> LENGTH: 27
<212> TYPE: DNA
<213> ORGANISM: JC virus

<400> SEQUENCE: 232
ttggctgcta cagtatcaac agcctgc                                              27

<210> SEQ ID NO 233
<211> LENGTH: 27
<212> TYPE: DNA
<213> ORGANISM: JC virus

<400> SEQUENCE: 233
ttgatttttg ctatctgcaa aaatttg                                              27

<210> SEQ ID NO 234
<211> LENGTH: 27
<212> TYPE: DNA
<213> ORGANISM: JC virus

<400> SEQUENCE: 234
ttgctatctg caaaaatttg ggcatta                                              27

<210> SEQ ID NO 235
<211> LENGTH: 27
<212> TYPE: DNA
<213> ORGANISM: JC virus

<400> SEQUENCE: 235
ttgggcatta taatagtgtt tttcatg                                              27

<210> SEQ ID NO 236
<211> LENGTH: 27
<212> TYPE: DNA
<213> ORGANISM: JC virus

<400> SEQUENCE: 236
ttggctgatc ctttttttca cattttt                                              27

<210> SEQ ID NO 237
<211> LENGTH: 27
```

```
<212> TYPE: DNA
<213> ORGANISM: JC virus

<400> SEQUENCE: 237
ttgctgtggg ttttcctgaa agtctaa                                               27

<210> SEQ ID NO 238
<211> LENGTH: 27
<212> TYPE: DNA
<213> ORGANISM: JC virus

<400> SEQUENCE: 238
ttggtttcca aggcatactg tgtaact                                               27

<210> SEQ ID NO 239
<211> LENGTH: 27
<212> TYPE: DNA
<213> ORGANISM: JC virus

<400> SEQUENCE: 239
ttgacagtag ttattaattg ctgacac                                               27

<210> SEQ ID NO 240
<211> LENGTH: 27
<212> TYPE: DNA
<213> ORGANISM: JC virus

<400> SEQUENCE: 240
ttgctgacac tctatgtcta tgtggtg                                               27

<210> SEQ ID NO 241
<211> LENGTH: 27
<212> TYPE: DNA
<213> ORGANISM: JC virus

<400> SEQUENCE: 241
ttgactgagg aatgcatgca gatctac                                               27

<210> SEQ ID NO 242
<211> LENGTH: 27
<212> TYPE: DNA
<213> ORGANISM: JC virus

<400> SEQUENCE: 242
ttgggatcct gtgttttcat catcact                                               27

<210> SEQ ID NO 243
<211> LENGTH: 27
<212> TYPE: DNA
<213> ORGANISM: JC virus

<400> SEQUENCE: 243
ttgggttaag tcacacccaa accattg                                               27

<210> SEQ ID NO 244
<211> LENGTH: 27
<212> TYPE: DNA
<213> ORGANISM: JC virus

<400> SEQUENCE: 244
ttgtctgaag caatcaaagc aatagca                                               27

<210> SEQ ID NO 245
```

```
<211> LENGTH: 27
<212> TYPE: DNA
<213> ORGANISM: JC virus

<400> SEQUENCE: 245
ttgcaataaa gggtatcaga attagga                                          27

<210> SEQ ID NO 246
<211> LENGTH: 27
<212> TYPE: DNA
<213> ORGANISM: JC virus

<400> SEQUENCE: 246
ttgttccatt tttttatata aaaaatt                                          27

<210> SEQ ID NO 247
<211> LENGTH: 27
<212> TYPE: DNA
<213> ORGANISM: JC virus

<400> SEQUENCE: 247
ttgtcttcgt ccccaccttt atcaggg                                          27

<210> SEQ ID NO 248
<211> LENGTH: 27
<212> TYPE: DNA
<213> ORGANISM: JC virus

<400> SEQUENCE: 248
ttgcattttt tcagataagc ttttctc                                          27

<210> SEQ ID NO 249
<211> LENGTH: 27
<212> TYPE: DNA
<213> ORGANISM: JC virus

<400> SEQUENCE: 249
ttgcagcaaa aaattactgc aaaaaag                                          27
```

GENE EDITING METHODS AND COMPOSITIONS FOR ELIMINATING RISK OF JC VIRUS ACTIVATION AND PML (PROGRESSIVE MULTIFOCAL LEUKOENCEPHALOPATHY) DURING IMMUNOSUPPRESSIVE THERAPY

FIELD OF THE INVENTION

The present invention relates to methods and compositions for eliminating John Cunningham Virus (JCV) from host cells prior to and during the administration of immunosuppressive therapy, to eliminate the risk of activation of latent JCV, and the consequent onset of progressive multifocal leukoencephalopathy (PML). In particular, the invention relates to strategies for eliminating JCV by administration of compositions including Clustered Regularly Interspaced Short Palindromic Repeats (CRISPR) associated endonucleases, and one or more specific guide RNA sequences, to cleave target sites within the JCV genome. The invention also relates to strategies including the administration of JCV-targeting compositions including zinc-finger nucleases (ZFN), or transcription activator-like effector nucleases (TALEN).

BACKGROUND

Therapies have been developed to treat a wide range of formerly intractable diseases or conditions, such as multiple sclerosis; various cancers, autoimmune diseases such as Crohn's disease, ulcerative colitis, psoriasis, psoriatic arthritis, ankylosing spondylitis, and rheumatoid arthritis; and organ transplant rejection. A partial list of some of these therapies, and their mechanisms of action, is shown in TABLE 1. It can be seen, from TABLE 1, that these therapies cause immunosuppression either by inactivation, inhibition, or immobilization of immune effector cells (B-cells, T-cells, dendritic cells, monocytes, macrophages), or by cytotoxic side effects on immune effector cells.

TABLE 1

Drugs that have been shown to trigger JC Virus and result in PML:

| Drug | Treatment | MOA |
|---|---|---|
| IMMUNOMODULATORS | | |
| Brentuximab vedotin | Hodgkin's lymphomas | anti-CD30 |
| Rituximab | B-cell cancers | inhibits B-cell activity |
| Natalizumab | Multiple Sclerosis and Crohn's Disease | anti-alpha-4 integrin. α4-integrin is required for white blood cells to move into organs by preventing their crossing of blood vessel walls to reach affected organs |
| Fingolimod | Multiple Sclerosis | |
| Efalizumab | Psoriasis | inhibits lymphocyte activation |
| Vedolizumab | ulcerative colitis and Crohn's disease | Blocking the α4β7 integrin causes gut-selective anti-inflammatory activity |
| Dimethyl fumarate | psoriasis, necrobiosis lipoidica, granuloma annulare, sarcoidosis, and Multiple Sclerosis | hypoxic cell radiosensitizer |
| IMMUNOSUPPRESSANTS | | |
| Belatacept | immunosuppressant | blocks T-cell activation |
| Tacrolimus | immunosuppressant | Calcineurin Inhibitors/T-cell inhibitors |
| Sirolimus | immunosuppressant | mTOR inhibitors |
| Glucocorticoids | immunosuppressant | steroids |
| Methotrexate | immunosuppressant | antimetabolites |
| Azathioprine | immunosuppressant | antimetabolites |
| Cyclosporine | immunosuppressant | T-cell inhibitors |
| Cyclophosphamide | immunosuppressant | alkylating agents |
| Chlorambucil | immunosuppressant | alkylating agents |
| Mycophenolate mofetil | immunosuppressant | Antiproliferative/antibiotic agent |
| Daclizumab | immunosuppressant | prevents T-cell activation |
| Infliximab | Crohn's disease, ulcerative colitis, psoriasis, psoriatic arthritis, ankylosing spondylitis, and rheumatoid arthritis | anti-TNFα |
| Ocrelizumab | Immunosuppressant | Humanized anti-CD20 monoclonal antibody that binds CD20 on B-lymphocytes |
| Alemtuzumab | Immunosuppressant | An anti-CD52 monoclonal antibody that binds CD52, on the surface of mature lymphocytes to treat chronic lymphocytic leukemia, cutaneous T-cell lymphoma, T-cell lymphoma and Multiple Sclerosis |

TABLE 1-continued

Drugs that have been shown to trigger JC Virus and result in PML:

| Drug | Treatment | MOA |
|---|---|---|
| Laquinimod | Immunomodulator | For treatment of MS |
| Daclizumab | Immunosuppressant | Binds to CD25, the alpha subunit of the IL-2 receptor of T-cells. A humanized anti-CD25 monoclonal antibody for the treatment of relapsing forms of MS. |

The immunosuppressive action of these therapies carries the risk of activation of opportunistic pathogens that are normally kept in check by the immune system. Among the most serious risks is the risk of activation of John Cunningham Virus (JCV), a human neurotropic polyomavirus. JCV is the etiological agent of a fatal demyelinating disease, progressive multifocal leukoencephalopathy (PML). Lytic infection of JCV in glial cells of the central nervous system (CNS) results in the death of oligodendrocytes, the cells that are responsible for the production of myelin sheaths of neurons in the brain. This leads to a broad range of mild to severe neurological disturbances and eventually death (Berger, 2011). There are a number of predisposing factors to PML, all of which involve some level of impairment of the immune system.

Seroepidemological data indicate that the 75-80% of the human population is infected with JCV. Much of this infection occurs during childhood, by largely unknown routes (Saribas, et al., 2010). The virus typically remains latent, causing no symptoms. In a setting of impaired immunity, especially cellular immunity, the virus can reactivate, proliferating and inducing the symptoms of PML (Waggoner, et al, 2009). Latent virus can be maintained in the urinary tract and bone marrow, in the spleen and other lymphoid tissues, and in the CNS (Bayliss, et al., 2012). Reactivation during immunosuppression can reflect the reactivation of latent virus in the CNS, as well as the hematogenous spread of reactivated virus to the CNS (Bag, et al., 2010).

The JCV genome is comprised of double-stranded circular DNA of 5.1 kb in size, which codes for two classes of proteins at the early phase of viral infection, i.e. before DNA replication, and at the late phase of the infection cycle (DeCaprio, et al., 2013). A bi-directional coding sequence positioned between the early and late genes is responsible for viral gene expression and contains the origin of viral DNA replication. The viral early protein, large T-antigen (T-Ag), and a family of smaller sized T-Ag proteins, are produced by alternative splicing, and have a regulatory role in orchestrating the viral replication cycle. The large T-Ag, in particular, is responsible for initiation of viral DNA replication and the stimulation of viral late gene transcription, and thus is critical for all aspects of the viral life cycle (for review see White and Khalili, 2004). T-Ag binds to several cellular proteins such as p53 and pRb, and dysregulates proliferation of host cells. The late proteins include the viral capsid proteins VP1, VP2, and VP3 and a small regulatory protein known as agnoprotein (Khalili, et al., 2005).

Treatments for autoimmune disorders such as multiple sclerosis and rheumatoid arthritis, with new therapeutic immunomodulatory monoclonal antibodies, including natalizumab (Chakley and Berger, 2013) efalizumab (Schwab, et al., 2012), and rituximab Clifford, et al., 2011), are recognized as a predisposing factors for PML (Nagayama, et al., 2013). As a consequence of the risk of JCV activation and PML, these treatments, and many of the other treatments listed in Table 1, must to be administered in sub-optimal concentrations with extensive patient monitoring. In some cases, the PML risk is sufficient to cause the removal of immunosuppressive drugs from the market, thereby barring patient access to potentially life-saving treatments.

A number of treatment options have been applied to PML, largely without success (Tavazzi, et al. 2012). Diverse approaches have targeted various points in the viral life cycle, such as cellular entry and replication. Since interaction between JCV and the serotonin 2A receptor (5-HT2AR) has been reported to be required for viral entry (Elphick, et al., 2004), risperidone, which binds 5HT2AR, has been tested but found to have no effect (Chapagain, et al., 2008). Small molecule inhibitors of viral replication such as cidofovir have been tested in vitro and in vivo, but have yielded conflicting results (Andrei, et al., 1997, Hou and Major, 1998). Alternative strategies are urgently required for dealing with this fatal demyelinating disease.

One potentially effective strategy would be to eliminate latent JCV from the host cells of patients prior to the start of immunosuppressive therapy, or during and after the course of therapy. With no latent virus to be activated, there would be no need to treat an active JCV infection. New and developing gene editing systems that target the JCV viral genome would be particularly attractive tools for JCV elimination. Example systems include zinc-finger nucleases (ZFN), transcription activator-like effector nucleases (TALEN) and Clustered Regulatory Interspaced Short Palindromic Repeat (CRISPR)-associated nuclease systems (Gaj, et al., 2013).

In particular, tools and techniques based on CRISPR/ endonuclease DNA editing systems offer unprecedented control over genome editing (Mali, et al., 2013, Hsu, et al., 2014). The CRISPR/Cas9 (CRISPR-associated endonuclease 9) system was developed from the adaptive immune system of bacteria and archaea. The CRISPR/Cas9 system uses short guide RNAs (gRNAs) to direct the cleavage of specific nucleic acid target sequences by a Cas9 endonuclease (Bhaya, et al., 2011). The cleavage, usually a blunt ended double-strand cut, can cause deletions, insertions, and excisions of stretches of DNA, caused by defective DNA repair. Recently, it was reported that CRISPR/Cas9 can be used to eliminate JCV from latently infected cells and prevent new JCV infection (Wollebo, et al., 2015). Recently, the range of targets has been expanded by the introduction of a CRISPR system that utilizes an alternative endonuclease, Cpf1, which is directed by gRNAs different from those which direct Cas9, to target sequences different from those cleaved by Cas9 (Zetsche, et al., 2015). There is a need for compositions and methods for the employment of these gene editing systems in treatments to eliminate latent JCV from patient cells prior to immunosuppressive treatments.

SUMMARY

The present invention provides a method of eliminating the risk of JCV activation in a subject undergoing immunosuppressive therapy, by administering an effective amount of a gene editing composition directed toward at least one target sequence in the JCV genome, cleaving the target sequence in the JCV genome, disrupting the JCV genome, eliminating the JCV infection, eliminating the risk of JCV activation, and treating the subject with an immunosuppressive therapy before, during or after administering the gene editing composition.

The present invention also provides for a pharmaceutical composition including at least one isolated nucleic acid sequence encoding a CRISPR-associated endonuclease and at least one gRNA having a spacer sequence complementary to a target sequence in a JCV DNA, the isolated nucleic acid sequences being included in at least one expression vector.

The present invention further provides for a pharmaceutical composition including at least one isolated nucleic acid sequence encoding at least one TALEN, which targets at least one nucleotide sequence of the JCV genome, the isolated nucleic acid sequence being included in at least one expression vector.

The present invention still further provides for a pharmaceutical composition including at least one isolated nucleic acid sequence encoding at least one ZFN, which targets at least one nucleotide sequence of the JCV genome, the isolated nucleic acid sequence being included in at least one expression vector.

The present invention also provides for a pharmaceutical composition for use in eliminating John Cunningham Virus (JCV) from a host cell infected with JCV, including at least one isolated nucleic acid sequence encoding a gene editing composition chosen from C2c1, C2c3, TevCas9, Archaea Cas9, CasY.1-CasY.6, CasX, and argonaute protein, which targets at least one nucleotide sequence of the JCV genome, the isolated nucleic acid sequences being included in at least one expression vector.

BRIEF DESCRIPTION OF THE DRAWINGS

Other advantages of the present invention are readily appreciated as the same becomes better understood by reference to the following detailed description when considered in connection with the accompanying drawing wherein:

FIG. 1 shows a nucleotide sequence encoding the large T antigen of JCV;

FIG. 2A is a diagram of lysogenic replication, and FIG. 2B is a diagram of lytic replication;

FIG. 4 is a chart of various Cas effectors.

DETAILED DESCRIPTION

Figure 3:
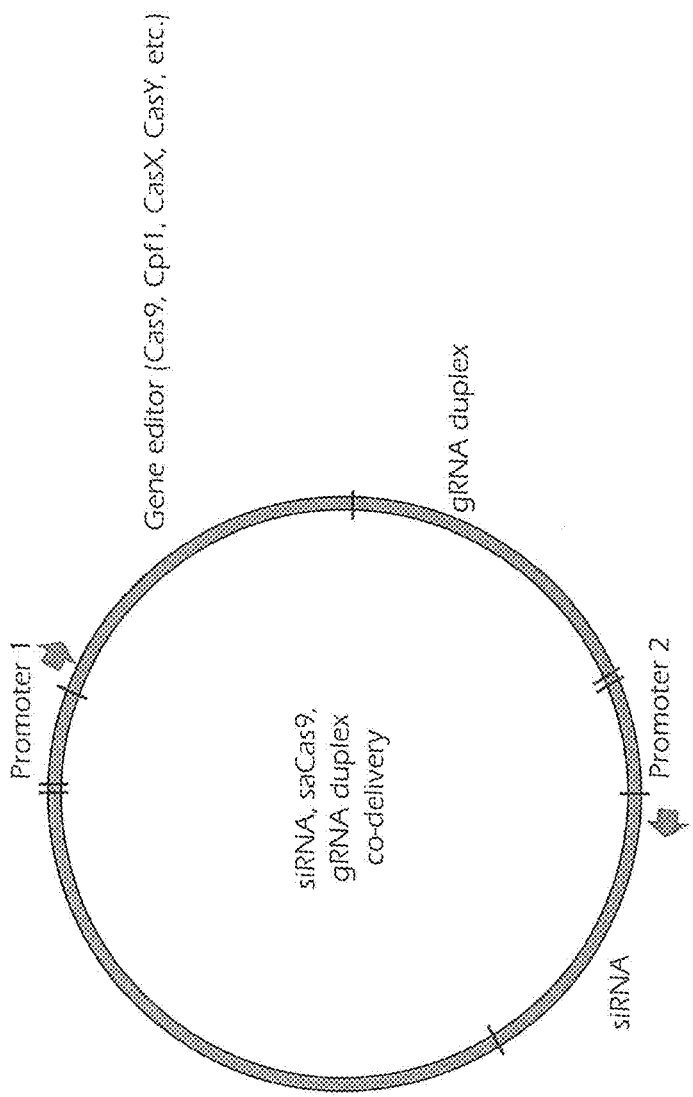
FIG. 3 is a diagram of siRNA, gene editor, and gRNA duplex codelivery.

The present invention represents the first application of gene editing technology to the problem of latent JCV reservoirs in candidate patients for immunosuppressive therapy. With the reservoirs eliminated by a gene editing system, the risk of PML by JCV activation is obviated. Immunosuppressive treatments previously deemed to be too risky for use in the face of latent JCV can now be freely administered, with no need for deliberate under-treatment to reduce risk. The methods and compositions of the present invention can serve as co-therapeutics for any of the treatments listed in TABLE 1, and for all immunosuppressive treatments that can activate JCV, including currently extant treatments, and those to be developed in the future.

CRISPR Compositions and Methods for Eliminating the Risk of JCV Activation During Immunosuppressive Therapy.

One preferred gene editing means for eliminating latent JCV is RNA-guided CRISPR technology. In a CRISPR system, CRISPR clusters encode spacers, which are sequences complementary to target sequences ("protospacers") in a viral nucleic acid, or in another nucleic acid to be targeted. CRISPR clusters are transcribed and processed into mature CRISPR RNAs (crRNAs). CRISPR clusters also encode CRISPR associated (Cas) proteins, which include DNA endonucleases. The crRNA binds to target DNA sequence, whereupon the Cas endonuclease cleaves the target DNA at or adjacent to the target sequence.

One useful CRISPR system includes the CRISPR associated endonuclease Cas9. Cas9 is guided by a mature crRNA that contains about 20-30 base pairs (bp) of spacer and a trans-activated small RNA (tracrRNA) that serves as a guide for ribonuclease III-aided processing of pre-crRNA. The crRNA:tracrRNA duplex directs Cas9 to target DNA via complementary base pairing between the spacer on the crRNA and the target sequence on the target DNA. Cas9 recognizes a trinucleotide (NGG) photospacer adjacent motif (PAM) to decide the cut site (the $3^{rd}$ nucleotide from PAM). The crRNA and tracrRNA can be expressed separately or engineered into an artificial chimeric small guide RNA (sgRNA) via a synthetic stem loop (AGAAAU) to mimic the natural crRNA/tracrRNA duplex. Such sgRNAs, can be synthesized or in vitro transcribed for direct RNA transfection, or they can be expressed in situ, e.g. from U6 or H1-promoted RNA expression vectors. The term "guide RNA" (gRNA) will be used to denote either a crRNA:tracrRNA duplex or an sgRNA. It will be understood the term "gRNA complementary to" a target sequence indicates a gRNA whose spacer sequence is complementary to the target sequence.

Other CRISPR systems that can be used include CRISPR/Cpf1, which is a DNA-editing technology analogous to the CRISPR/Cas9 system, characterized in 2015 by Feng Zhang's group from the Broad Institute and MIT. Cpf1 is an RNA-guided endonuclease of a class II CRISPR/Cas system. This acquired immune mechanism is found in Prevotella and Francisella bacteria. It prevents genetic damage from viruses. Cpf1 genes are associated with the CRISPR locus, coding for an endonuclease that use a guide RNA to find and cleave viral DNA. Cpf1 is a smaller and simpler endonuclease than Cas9, overcoming some of the CRISPR/Cas9 system limitations. Cpf1 is further described below.

Argonaute proteins can also be used. Argonaute proteins are proteins of the PIWI protein superfamily that contain a PIWI (P element-induced wimpy testis) domain, a MID (middle) domain, a PAZ (Piwi-Argonaute-Zwille) domain and an N-terminal domain. Argonaute proteins are capable of binding small RNAs, such as microRNAs, small interfering RNAs (siRNAs), and Piwi-interacting RNAs. Argonaute proteins can be guided to target sequences with these RNAs in order to cleave mRNA, inhibit translation, or induce mRNA degradation in the target sequence. There are several different human Argonaute proteins, including AGO1, AGO2, AGO3, and AGO4 that associate with small RNAs. AGO2 has slicer ability, i.e. acts as an endonuclease.

Argonaute proteins can be used for gene editing. Endonucleases from the Argonaute protein family (from Natronobacterium gregoryi Argonaute) also use oligonucleotides as guides to degrade invasive genomes. Work by Gao et al has shown that the Natronobacterium gregoryi Argonaute (NgAgo) is a DNA-guided endonuclease suitable for genome editing in human cells. NgAgo binds 5' phosphorylatedsingle-stranded guide DNA (gDNA) of ~24 nucleotides, efficiently creates site-specific DNA double-strand breaks when loaded with the gDNA. The NgAgo-gDNA system does not require a protospacer-adjacent motif (PAM), as does Cas9, and preliminary characterization suggests a low tolerance to guide-target mismatches and high efficiency in editing (G+C)-rich genomic targets. The Argonaute protein endonucleases used in the present invention can also be Rhodobacter sphaeroides Argonaute (RsArgo). RsArgo can provide stable interaction with target DNA strands and guide RNA, as it is able to maintain base-pairing in the 3'-region of the guide RNA between the N-terminal and PIWI domains. RsArgo is also able to specifically recognize the 5' base-U of guide RNA, and the duplex-recognition loop of the PAZ domain with guide RNA can be important in DNA silencing activity. Other prokaryotic Argonaute proteins (pAgos) can also be used in DNA interference and cleavage. The Argonaute proteins can be derived from *Arabidopsis thaliana, D. melanogaster, Aquifex aeolicus, Thermus thermophiles, Pyrococcus furiosus, Thermus thermophilus* JL-18, *Thermus thermophilus* strain HB27, *Aquifex aeolicus* strain VF5, *Archaeoglobus fulgidus, Anoxybacillus flavithermus, Halogeometricum borinquense, Microsystis aeruginosa, Clostridium bartlettii, Halorubrum lacusprofundi, Thermosynechococcus elongatus*, and *Synechococcus elongatus*. Argonaute proteins can also be used that are endo-nucleolytically inactive but post-translational modifications can be made to the conserved catalytic residues in order to activate them as endonucleases. Therefore, the present invention also provides for a pharmaceutical composition including at least one isolated nucleic acid sequence encoding at least one argonaute protein, which targets at least one nucleotide sequence of the JCV genome, the isolated nucleic acid sequences being included in at least one expression vector. This composition can further include any of siRNA, miRNAs, shRNAs, or RNAi further described below.

Human WRN is a RecQ helicase encoded by the Werner syndrome gene. It is implicated in genome maintenance, including replication, recombination, excision repair and DNA damage response. These genetic processes and expression of WRN are concomitantly upregulated in many types of cancers. Therefore, it has been proposed that targeted destruction of this helicase could be useful for elimination of cancer cells. Reports have applied the external guide sequence (EGS) approach in directing an RNase P RNA to efficiently cleave the WRN mRNA in cultured human cell lines, thus abolishing translation and activity of this distinctive 3'-5' DNA helicase-nuclease. RNase P RNA is another potential endonuclease for use with the present invention.

The Class 2 type VI-A CRISPR/Cas effector "C2c2" demonstrates an RNA-guided RNase function. C2c2 from the bacterium *Leptotrichia shahii* provides interference against RNA phage. In vitro biochemical analysis show that C2c2 is guided by a single crRNA and can be programmed to cleave ssRNA targets carrying complementary protospacers. In bacteria, C2c2 can be programmed to knock down specific mRNAs. Cleavage is mediated by catalytic residues in the two conserved HEPN domains, mutations in which generate catalytically inactive RNA-binding proteins. The RNA-focused action of C2c2 complements the CRISPR-Cas9 system, which targets DNA, the genomic blueprint for cellular identity and function. The ability to target only RNA, which helps carry out the genomic instructions, offers the ability to specifically manipulate RNA in a high-throughput manner—and manipulate gene function more broadly. These results demonstrate the capability of C2c2 as a new RNA-targeting tools.

Another Class 2 type V-B CRISPR/Cas effector "C2c1" can also be used in the present invention for editing DNA. C2c1 contains RuvC-like endonuclease domains related distantly to Cpf1 (described below). C2c1 can target and cleave both strands of target DNA site-specifically. According to Yang, et al. (PAM-Dependent Target DNA Recognition and Cleavage by C2c1 CRISPR-Cas Endonuclease, Cell, 2016 Dec. 15; 167(7):1814-1828)), a crystal structure confirms *Alicyclobacillus acidoterrestris* C2c1 (AacC2c1) binds to sgRNA as a binary complex and targets DNAs as ternary complexes, thereby capturing catalytically competent conformations of AacC2c1 with both target and non-target DNA strands independently positioned within a single RuvC catalytic pocket. Yang, et al. confirms that C2c1-mediated cleavage results in a staggered seven-nucleotide break of target DNA, crRNA adopts a pre-ordered five-nucleotide A-form seed sequence in the binary complex, with release of an inserted tryptophan, facilitating zippering up of 20-bp guide RNA:target DNA heteroduplex on ternary complex formation, and that the PAM-interacting cleft adopts a "locked" conformation on ternary complex formation.

C2c3 is a gene editor effecor of type V-C that is distantly related to C2c1, and also contains RuvC-like nuclease domains. C2c3 is also similar to the CasY.1-CasY.6 group described below.

A CRISPR/TevCas9 system can also be used. In some cases it has been shown that once CRISPR/Cas9 cuts DNA in one spot, DNA repair systems in the cells of an organism will repair the site of the cut. The TevCas9 enzyme was developed to cut DNA at two sites of the target so that it is harder for the cells' DNA repair systems to repair the cuts (Wolfs, et al., Biasing genome-editing events toward precise length deletions with an RNA-guided TevCas9 dual nuclease, PNAS, doi:10.1073). The TevCas9 nuclease is a fusion of a I-Tevi nuclease domain to Cas9.

The gene editor effector can also be Archaea Cas9. The size of Archaea Cas9 is 950aa ARMAN 1 and 967aa ARMAN 4. The Archaea Cas9 can be derived from ARMAN-1 (*Candidatus Micrarchaeum acidiphilum* ARMAN-1) or ARMAN-4 (*Candidatus Parvarchaeum acidiphilum* ARMAN-4). Two examples of Archaea Cas9 are provided in FIG. 2, derived from ARMAN-1 and ARMAN-4. The sequences for ARMAN 1 and ARMAN 4 are below.

```
ARMAN 1 amino acid sequence 950aa
(SEQ ID NO: 250):
MRDSITAPRYSSALAARIKEFNSAFKLGIDLGTKTGGVALVKDNKVLLAKTFLDYHKQTLEERRIHRRNR

RSRLARRKRIARLRSWILRQKIYGKQLPDPYKIKKMQLPNGVRKGENWIDLVVSGRDLSPEAFVRAITLI
```

-continued

FQKRGQRYEEVAKEIEEMSYKEFSTHIKALTSVTEEEFTALAAEIERRQDVVDTDKEAERYTQLSELLSK

VSESKSESKDRAQRKEDLGKVVNAFCSAHRIEDKDKWCKELMKLLDRPVRHARFLNKVLIRCNICDRATP

KKSRPDVRELLYFDTVRNFLKAGRVEQNPDVISYYKKIYMDAEVIRVKILNKEKLTDEDKKQKRKLASEL

NRYKNKEYVTDAQKKMQEQLKTLLFMKLTGRSRYCMAHLKERAAGKDVEEGLHGVVQKRHDRNIAQRNHD

LRVINLIESLLFDQNKSLSDAIRKNGLMYVTIEAPEPKTKHAKKGAAVVRDPRKLKEKLFDDQNGVCIYT

GLQLDKLEISKYEKDHIFPDSRDGPSIRDNLVLTTKEINSDKGDRTPWEWMHDNPEKWKAFERRVAEFYK

KGRINERKRELLLNKGTEYPGDNPTELARGGARVNNFITEFNDRLKTHGVQELQTIFERNKPIVQVVRGE

ETQRLRRQWNALNQNFIPLKDRAMSFNHAEDAAIAASMPPKFWREQIYRTAWHFGPSGNERPDFALAELA

PQWNDFFMTKGGPIIAVLGKTKYSWKHSIIDDTIYKPFSKSAYYVGIYKKPNAITSNAIKVLRPKLLNGE

HTMSKNAKYYHQKIGNERFLMKSQKGGSIITVKPHDGPEKVLQISPTYECAVLTKHDGKIIVKFKPIKPL

RDMYARGVIKAMDKELETSLSSMSKHAKYKELHTHDIIYLPATKKHVDGYFIITKLSAKHGIKALPESMV

KVKYTQIGSENNSEVKLTKPKPEITLDSEDITNIYNFTR

ARMAN 1 nucleic acid sequence
(SEQ ID NO: 251):
atga gagactctat tactgcacct agatacagct ccgctcttgc cgccagaata aggagttta attctgcttt caagttagga atcgacctag gaacaaaaac cggcggcgta gcactggtaa aagacaacaa agtgctgctc gctaagacat cctcgatta ccataaacaa acactggagg aaaggaggat ccatagaaga aacagaagga gcaggctagc caggcggaag aggattgctc ggctgcgatc atggatactc agacagaaga tttatggcaa gcagcttcct gacccataca aaatcaaaaa aatgcagttg cctaatggtg tacgaaaagg ggaaaactgg attgacctgg tagtttctgg acgggacctt tcaccagaag ccttcgtgcg tgcaataact ctgatattcc aaaagagagg gcaaagatat gaagaagtgg ccaaagagat agaagaaatg agttacaagg aattagtac tcacataaaa gccctgacat ccgttactga agaagaattt actgctctgg cagcagagat agaacggagg caggatgtgg ttgacacaga caaggaggcc gaacgctata cccaattgtc tgagttgctc tccaaggtct cagaaagcaa atctgaatct aaagacagag cgcagcgtaa ggaggatctc ggaaaggtgg tgaacgcttt ctgcagtgct catcgtatcg aagacaagga taatggtgt aaagaactta tgaaattact agacagacca gtcagacacg ctaggttcct taacaaagta ctgatacgtt gcaatatctg cgatagggca acccctaaga aatccagacc tgacgtgagg gaactgctat attttgacac agtaagaaac ttcttgaagg ctggaagagt gggagcaaaac ccagacgtta ttagttacta taaaaaaatt tatatggatg cagaagtaat cagggtcaaa attctgaata aggaaaagct gactgatgag acaaaaagc aaaagaggaa attagcgagc gaacttaaca ggtacaaaaa caagaatac gtgactgatg cgcagaagaa gatgcaagag caacttaaga cattgctgtt catgaagctg acaggcaggt ctagatactg catggctcat cttaaggaaa gggcagcagg caaagatgta gaagaaggac ttcatggcgt tgtgcagaaa agacacgaca ggaacatagc acagcgcaat cacgacttac gtgtgattaa tcttattgag agtctgcttt tcgaccaaaa caaatcgctc tccgatgcaa taaggaagaa cgggttaatg tatgttacta ttgaggctcc agagccaaag actaagcacg caaagaaagg cgcagctgtg gtaagggatc ccagaaagtt gaaggagaag ttgtttgatg atcaaaacgg cgtttgcata tacgggct tgcagttaga caaattagag ataagtaaat acgagaagga ccatatcttt ccagattcaa gggatggacc atctatcagg acaatcttg tactcactac aaaagagata aattcagaca aggcgatag accccatgg gaatggatgc atgataaccc agaaaaatgg aaagcgttcg agagaagagt cgcagaattc tataagaaag -continued

```
gcagaataaa tgagaggaaa agagaactcc tattaaacaa aggcactgaa tacccctggcg ataacccgac tgagctggcg cggggaggcg cccgtgttaa caactttatt actgaattta atgaccgcct caaaacgcat ggagtccagg aactgcagac catctttgag cgtaacaaac caatagtgca ggtagtcagg ggtgaagaaa cgcagcgtct cgcagacaa tggaatgcac taaaccagaa tttcatacca ctaaaggaca gggcaatgtc gttcaaccac gctgaagacg cagccatagc agcaagcatg ccaccaaaat tctggaggga gcagatatac cgtactgcgt ggcactttgg acctagtgga aatgagagac cggactttgc tttggcagaa ttggcgccac aatggaatga cttctttatg actaagggcg gtccaataat agcagtgctg ggcaaaacga agtatagttg gaagcacagc ataattgatg acactatata caagccattc agcaaaagtg cttactatgt tgggatatac aaaaagccga acgccatcac gtccaatgct ataaaagtct taaggccaaa actcttaaat ggcgaacata caatgtctaa gaatgcaaag tattatcatc agaagattgg taatgagcgc ttcctcatga aatctcagaa aggtggatcg ataattacag taaaaccaca cgacggaccg gaaaaagtgc ttcaaatcag ccctacatat gaatgcgcag tccttactaa gcatgacggt aaaataatag tcaaatttaa accaataaag ccgctacggg acatgtatgc ccgcggtgtg attaaagcca tggacaaaga gcttgaaaca agcctctcta gcatgagtaa acacgctaag tacaaggagt tacacactca tgatatcata tatctgcctg ctacaaagaa gcacgtagat ggctacttca taataaccaa actaagtgcg aaacatggca taaaagcact ccccgaaagc atggttaaag tcaagtatac tcaaattggg agtgaaaaca atagtgaagt gaagcttacc aaaccaaaac cagagataac tttggatagt gaagatatta caaacatata taatttcacc cgctaag
```

ARMAN 4 amino acid sequence 967aa
(SEQ ID NO: 252):
MLGSSRYLRYNLTSFEGKEPFLIMGYYKEYNKELSSKAQKEFNDQISEFNSYYKLGIDLGDKTGIAIVKG

NKIILAKTLIDLHSQKLDKRREARRNRRTRLSRKKRLARLRSWVMRQKVGNQRLPDPYKIMHDNKYWSIY

NKSNSANKKNWIDLLIHSNSLSADDFVRGLTIIFRKRGYLAFKYLSRLSDKEFEKYIDNLKPPISKYEYD

EDLEELSSRVENGEIEEKKFEGLKNKLDKIDKESKDFQVKQREEVKKELEDLVDLFAKSVDNKIDKARWK

RELNNLLDKKVRKIRFDNRFILKCKIKGCNKNTPKKEKVRDFELKMVLNNARSDYQISDEDLNSFRNEVI

NIFQKKENLKKGELKGVTIEDLRKQLNKTFNKAKIKKGIREQIRSIVFEKISGRSKFCKEHLKEFSEKPA

PSDRINYGVNSAREQHDFRVLNFIDKKIFKDKLIDPSKLRYITIESPEPETEKLEKGQISEKSFETLKEK

LAKETGGIDIYTGEKLKKDFEIEHIFPPRARMGPSIRENEVASNLETNKEKADRTPWEWFGQDEKRWSEFE

KRVNSLYSKKKISERKREILLNKSNEYPGLNPTELSRIPSTLSDFVESIRKMFVKYGYEEPQTLVQKGKP

IIQVVRGRDTQALRWRWHALDSNIIPEKDRKSSFNHAEDAVIAACMPPYYLRQKIFREEAKIKRKVSNKE

KEVTRPDMPTKKIAPNWSEFMKTRNEPVIEVIGKVKPSWKNSIMDQTFYKYLLKPFKDNLIKIPNVKNTY

KWIGVNGQTDSLSLPSKVLSISNKKVDSSTVLLVHDKKGGKRNWVPKSIGGLLVYITPKDGPKRIVQVKP

ATQGLLIYRNEDGRVDAVREFINPVIEMYNNGKLAFVEKENEEELLKYFNLLEKGQKFERIRRYDMITYN

SKFYYVTKINKNHRVTIQEESKIKAESDKVKSSSGKEYTRKETEELSLQKLAELISI

ARMAN 4 nucleic acid sequence
(SEQ ID NO: 253):

```
at gttaggctcc agcaggtacc tccgttataa cctaacctcg tttgaaggca aggagccatt tttaataatg ggatattaca aagagtataa taaggaatta agttccaaag ctcaaaaaga atttaatgat caaatttctg aatttaattc gtattacaaa ctaggtatag atctcggaga taaaacagga attgcaatcg taaagggcaa caaaataatc ctagcaaaaa cactaattga
```

-continued

```
tttgcattcc caaaaattag ataaaagaag ggaagctaga agaaatagaa gaactcggct ttccagaaag aaaaggcttg cgagattaag atcgtgggta atgcgtcaga aagttggcaa tcaaagactt cccgatccat ataaaataat gcatgacaat aagtactggt ctatatataa taagagtaat tctgcaaata aaaagaattg gatagatctg ttaatccaca gtaactcttt atcagcagac gattttgtta gaggcttaac tataattttc agaaaagag gctatttagc atttaagtat cttcaaggt taagcgataa ggaatttgaa aaatacatag ataacttaaa accacctata agcaaatacg agtatgatga ggatttagaa gaattatcaa gcagggttga aaatggggaa atagaggaaa agaaattcga aggcttaaag aataagctag ataaaataga caaagaatct aaagactttc aagtaaagca aagagaagaa gtaaaaaagg aactggaaga cttagttgat ttgttttgcta aatcagttga taataaaata gataaagcta ggtggaaaag ggagctaaat aatttattgg ataagaaagt aaggaaaata cggtttgaca accgctttat tttgaagtgc aaaattaagg gctgtaacaa gaatactcca aagaaagaga aggtcagaga ttttgaattg aagatggttt taaataatgc tagaagcgat tatcagattt ctgatgagga tttaaactct tttagaaatg aagtaataaa tatatttcaa aagaaggaaa acttaaagaa aggagagctg aaaggagtta ctattgaaga tttgagaaag cagcttaata aaacttttaa taaagccaag attaaaaaag ggataaggga gcagataagg tctatcgtgt ttgaaaaaat tagtggaagt agtaaattct gcaaagaaca tctaaaagaa ttttctgaga agccggctcc ttctgacagg attaattatg gggttaattc agcaagagaa caacatgatt ttagagtctt aaatttcata gataaaaaa tattcaaaga taagttgata gatccctcaa aattgaggta tataactatt gaatctccag aaccagaaac agagaagttg gaaaaaggtc aaatatcaga gaagagcttc gaaacattga aagaaaaatt ggctaaagaa acaggtggta ttgatatata cactggtgaa aaattaaaga aagactttga aatagagcac atattcccaa gagcaaggat ggggccttct ataagggaaa acgaagtagc atcaaatctg gaaacaaata aggaaaaggc cgatagaact ccttgggaat ggtttgggca agatgaaaaa agatggtcag agtttgagaa aagagttaat tctctcttata gtaaaaagaa aatatcagag agaaaagag aaattttgtt aaataagagt aatgaatatc cgggattaaa ccctacagaa ctaagtagaa tacctagtac gctgagcgac ttcgttgaga gtataagaaa aatgtttgtt aagtatggct atgaagagcc tcaaactttg gttcaaaaag gaaaaccgat aatacaagtt gttagaggca gagacacaca agctttgagg tggagatggc atgcattaga tagtaatata ataccagaaa aggacaggaa aagttcattt aatcacgctg aagatgcagt tattgccgcc tgtatgccac cttactatct caggcaaaaa atatttagag aagaagcaaa aataaaaaga aaagtaagca ataaggaaaa ggaagttaca cggcctgaca tgcctactaa aaagatagct ccgaactggt cggaattat gaaaactaga aatgagccgg ttattgaagt aataggaaaa gttaagccaa gctgaaaaaa cagcataatg gatcaaacat tttataaata tcttttgaag ccatttaaag ataacctgat aaaaatacc aacgttaaaa atacatacaa gtggatagga gttaatggac aaactgattc attatccctc ccgagtaagg tcttatctat ctctaataaa aaggttgatt cttctacagt tcttcttgtg catgataaga agggtggtaa gcggaattgg gtacctaaaa gtataggggg tttgttggta tatataactc ctaaagacgg gccgaaaaga atagttcaag taaagccagc aactcagggt ttgttaatat atagaaatga agatggcaga gtagatgctg taagagagtt cataaatcca gtgatagaaa tgtataataa tggcaaattg gcatttgtag aaaaagaaaa tgaagaagag cttttgaaat attttaattt gctggaaaaa ggtcaaaaat ttgaaagaat
```

-continued

```
aagacggtat gatatgataa cctacaatag taaattttac tatgtaacaa aaataaacaa gaatcacaga gttactatac aagaagagtc taagataaaa gcagaatcag acaaagttaa gtcctcttca ggcaaagagt atactcgtaa ggaaaccgag gaattatcac ttcaaaaatt agcggaatta attagtatat aaaa
```

The gene editor effector can also be CasX, examples of which are shown in FIG. 4. CasX has a TTC PAM at the 5' end (similar to Cpf1). The TTC PAM can have limitations in viral genomes that are GC rich, but not so much in those that are GC poor. The size of CasX (986 bp), smaller than other type V proteins, provides the potential for four gRNA plus one siRNA in a delivery plasmid. CasX can be derived from Deltaproteobacteria or Planctomycetes. The sequences for these CasX effectors are below.

```
CasX.1 Planctomycetes amino acid sequence 978aa
(SEQ ID NO: 254):
MQEIKRINKIRRRLVKDSNTKKAGKTGPMKTLLVRVMTPDLRERLENLRKKPENIPQPISNTSRANLNKLLTDYTEMKKAILHVYWE EFQKDPVGLMSRVAQPAPKNIDQRKLIPVKDGNERLTSSGFACSQCCQPLYVYKLEQVNDKGKPHTNYFGRCNVSEHERLILLSPHK PEANDELVTYSLGKFGQRALDFYSIHVTRESNHPVKPLEQIGGNSCASGPVGKALSDACMGAVASFLTKYQDIILEHQKVIKKNEKR LANLKDIASANGLAFPKITLPPQPHTKEGIEAYNNVVAQIVIWVNLNLWQKLKIGRDEAKPLQRLKGFPSFPLVERQANEVDWWDMV CNVKKLINEKKEDGKVFWQNLAGYKRQEALLPYLSSEEDRKKGKKFARYQFGDLLLHLEKKHGEDWGKVYDEAWERIDKKVEGLSKH IKLEEERRSEDAQSKAALTDWLRAKASFVIEGLKEADKDEFCRCELKLQKWYGDLRGKPFAIEAENSILDISGFSKQYNCAFIWQKD GVKKLNLYLIINYFKGGKLRFKKIKPEAFEANRFYTVINKKSGEIVPMEVNFNFDDPNLIILPLAFGKROGREFIWNDLLSLETGSL KLANGRVIEKTLYNRRTRODEPALFVALTFERREVLDSSNIKPMNLIGIDRGENIPAVIALTDPEGCPLSRFKDSLGNPTHILRIGE SYKEKORTIQAAKEVEORRAGGYSRKYASKAKNLADDMVRNTARDLLYYAVTODAMLIFENLSRGFGRQGKRTFMAERQYTRMEDWL TAKLAYEGLPSKTYLSKTLAQYTSKTCSNCGFTITSADYDRVLEKLKKTATGWMTTINGKELKVEGQITYYNRYKRQNVVKDLSVEL DRLSEESVNNDISSWTKGRSGEALSLLKKRFSHRPVQEKFVCLNCGFETHADEQAALNIARSWLFLRSQEYKKYQTNKTTGNTDKRA

FVETWQSFYRKKLKEVWKPAV

CasX.1 Planctomycetes nucleic acid sequence
(SEQ ID NO: 255):
atgct tcttatttat cggagatatc ttcaaacacc atcaacatgg caatggtgaa ccattaatat tctttgatgc ttcttattta tcggagatat cttcaaacat tgcccatttt acaggcatat cttctggctc tttgatgctt cttatttatc ggagatatct tcaaacgtaa tgtattgaga agacatcaa gattagataa ctttgatgct tcttatttat cggagatatc ttcaaacaca gaaacctgca aagattgtat atatataagc tttgatgctt cttatttatc ggagatatct tcaaacgata cgtattttag cccgtctatt tggggattaa cttttgatgct tcttatttat cggagatatc ttcaaacccc gcatatccag atttttcaat gacttctgga aattgtattt tcaatatttt acaagttgcg gaggatacct taataattt agcagagtta cgcactgtaa acctgttctt ctcacaaaaa gctttaacat cagattttca aagaacttct tatgtaattt ataagaatct aaaaaaacag ctctgggttt gcatccagaa ctctccgata aataagcgct ttacccatac gacatagtcg ctggtgatgg ctctcaaagt aatgagataa aagcgccagt aataatttac tattcacaaa tcctttcgtc aagcttaaaa tcaatcaaag accatatccc cttcattcca aatagcagcg cttccgtacc tttctatccg ttcatatatc tcctctgaga gaggataaat taccagactt atagagccat ccataaatcc ttttttctta aggttgagct ttagatcagc ccaccttgct tttgaaaggt taaactcaaa gacagaatat tgaatccgaa caccataggc ttccagaagt ttaactaacc gtgccctgac cttatcatct tcaatatcat aacaaatgag atgtcgcatt ttaaagctct ataggcttat aacattccct atcatcttga atatgctggc taaacaacct aacctgccgc tcaactgcgt gctgatacgt tattgattgg ataagtaaat tggttttctg ctcatctacc ttaaagaatt gatgccattt tttgattact tttggatagg catccttatt cagccaaaca ccttttttggt cagtttcttt cctgaaatcg tctgtatcca cttcccttct atttatcaaa ttgatcacaa aacggtcagc caacggccgc cactcctcca gaagatcgca tattaaagag ggacgaccat aatagacgtc atgcaagtaa ccaaaggccg gtcaaaaccc gacgagtaat gcagtcgaat gtatttcgtt gaacaggagg gtgtagataa ggctcatcat ggcgttgatt tcatcctcag gaggtctctt
```

-continued

```
ggtacggcgc acaaaaacaa agcttggatg ctttaagata gccgaaaaat tgccataata ctgccttgtt gttgcgcctt ctattccacg caaggtctct aaatcagtga cggcgttgat ttcggtacac tcgattctca aaccaagtct atatttatca agtaatgatt gctggttttt gatcttaccg gcaacgatac ttttttgcaat ttcaagtttt ttgtggggat caaaatgctt atgaatttgc gcccgacgaa taaacagatt tttgacgggt tcaaattgaa ggctcccttg atattcccat ctgccgctaa agaaatgtat cggtatagat tattctctgc aaaggctaat aacacggcta tcgagggtaa cccggccaac taccacgata tcttttacct tcattgcggg aatcttctgc cccttctctt cattgtcctt ttttatgaga atgcccgac cacgacaatc caaaatgaat tcatcacccg tgagatagag ggttatcctg tcggttatag cggtcatcag taagccttt attttttctaa ccaagtattg aaggaagaca cgattcacta tactggcact gcggacacct atggtcatca accttgggaa acctgcttat atcaaaggac aagaagcagt ctcgcagatt tgtaacaact tctacacaac gcactttcag ggttttatct ataacaattt ctttccgtct ccgtgtttca cagaaaaata tttcaccaac tggtatattg acattataca tctcttcaag gcaaattgcc tgtaacccaa tctgaacgtg gaagttctca aaatcccta ccttccctgt ctttgtttcg ataggaatcg gtatcccatc cctccactcg ataaggtctg cccggcctgc caaaccgagc ttattgctgt aaagatacac gcctgttacc tgcttacaat cagggcagct tctctgcgat gatttatcca ccgccctgtg cgcgtgtatg gcctctgtaa agtggatgct cttagccata ttacgccgtt ctccaacaaa ggcataccat gcattgcgcg acaatagat tgactccatt accgtgctga tgtgcaatat cagacggctg gtttccatac ttctttgagc ttctttctgt aaaaggattg ccatgtttca acaaatgccc ttttgtcagt atttccggtc gttttattgg tttgatacttcttatattct tgagaacgga gaaagagcca cgaccttgca atattcagtg ctgcttgttc gtctgcatgg gtttcaaaac cacagttcag gcaaacaaac ttttcctgca ccggcctgtg actaaatctc tttttagca gagataaagc ttcaccactg cggccttttg tccaactaga aatatcatta tttaccgact cttccgaaag tctatccagc tctacagaga ggtcttttac cacattctgc cttttatacc ggttatagta tgttatctgt ccttcaactt ttaactcttt tccattgatt gtagtcatcc atccagtagc cgtcttcttg agcttttcga gcaccctgtc ataatctgca cttgtgattg taaaaccaca attagaacat gtctttgagg tatactgtgc cagagtcttt gaaagatagg ttttttgatgg cagaccttca taggcaagct ttgcagtcag ccagtcttcc atcctcgtgt actgcctttc cgccataaaa gtcctcttgc cttgtctacc aaaaccgcgg gaaagatttt caaaaatgag cattgcatct tgagtaacag cataatataa gaggtcacga gctgtatttc ttaccatatc gtccgccaga ttcttcgcct tgatgcata ttttctcgaa tatccgcctg cccgcctttg ttcaacttct ttagcagcct gaatagtccg ttgttttttcc ttataactttt ctccattcg caaaatatgc gttggattgc ccaatgaatc tttgaatctt dacaaggggc atccttccgg gtctgttaat gctatgactg ccgggatatt ttctccccgg tctattccta tcagattcat cggttttata ttcgatgagt caagcacctc tcttctttca aatgtcaggg caacaaaaag tgctggttca tcctgtctcg tccttctgtt atagagcgtt ttttcaataa ccctgccatt ggcgagtttc aatgaacccg tctcaaggct caataggtcg ttccagataa actccctccc ctgccttttt ccaaaggcca aaggcagaat tatcaaattc gggtcatcaa aattgaagtt gacctccata ggcacaatct caccgctttt tttattaatt actgtataaa acctatttgc ttcaaaagct tctggcttga ttttttttgaa gcgtagctta ccacctttga agtaatttat tattaaataa agatttaact tctttacgcc gtctttctgc catataaatg cacaattata ctgtttagaa aatccgctta tatctaaaat gctgttctct gcttctatag caaatggttt tcctctcaaa tctccatacc acttttgaag ctttaactca cacctgcaaa actcatcctt atcagcttct ttgagcccctt caataacaaa agaggccttt gccctgagcc aatcagtgag ggcagccttt gattgagcat cttcagacct tctttcttcc tccaacttta tgtgcttact cagaccttca acttttttat ctattctttc ccatgcctca tcataaactt tgccccaatc ttcaccgtgt ttcttttcaa ggtgaagcaa aaggtcacca aactgataac gcgcaaactt ttttcctttt ttacggtctt cttcagacga aagatatgga agcaaggctt cctgccttt atatccagca agattttgcc agaagacctt cccgtcctct ttcttttcgt taatcaactt tttgacatta cagaccatat cccaccaatc aacctcattc gcctggcgtt caacaagagg gaaggacgga aaacccttaa gccgctgtaa gggctttgcc tcatccctgc caattttgag tttctgccaa agattcaggt ttacccagat cactatctga gcaacaacat tgttataagc ttcaatccct tcttttgtat
```

```
gcggttgcgg tggaagagtg attttaggaa atgcaagccc gtttgcactt gctatatcct ttagatttgc caatctcttt tcgttttttt ttataacctt ttggtgttcg aggatgatgt cctggtactt tgtaaggaaa ctggctactg ctcccataca ggcatcagat aaagccttac aacgggacc acttgcgcag ctattgccac cgatctgttc tagcggcttt acaggatggt tcgattctct tgttacgtgg attgaataaa agtccaatgc cctttgaccg aacttcccca acgaatacgt tactagctcg tcatttgcct ccggtttatg cggcgagagc aatatcaaac gttcatgctc ggagacatta aacggccaa agtaatttgt atggggctta cccttgtcat tcacttgttc aagcttataa acatagaggg gttgacagca ctgagaacag gcaaatccag aacttgttag tctctcattt ccgtccttca ccggaatcaa ttttctctga tcaatattct tgggcgctgg ttgtgcaacc ctgctcatca atccgacagg gtcttttttgg aactcttccc aataaacatg caggattgct ttcttcattt ccgtatagtc agtgaggagt ttatttaaat ttgcacgtga agtatttgaa atgggctgag gaatgttttc cggcttttg cgaagattct ctaacctttc tctcaggtca ggtgtcataa cccgaacgag caaggttttc ataggggccgg ttttgccggc ttttttcgtg ttgctatcct ttaccaatct ccttcgtatt ttattttatcc tttttattc ctgcatcttt
```

CasX.1 Deltaproteobacteria amino acid sequence 986aa
(SEQ ID NO: 256):
MEKRINKIRKKLSADNATKPVSRSGPMKTLLVRVMTDDLKKRLEKRRKKPEVMPQVISNNAANNLRMLLDDYTKMKEAILQVYWQEF KDDHVGLMCKFAQPASKKIDONKLKPEMDEKGNLTTAGFACSQCGQPLFVYKLEQVSEKGKAYTNYFGRCNVAEHEKLILLAQLKPE KDSDEAVTYSLGKFGQRALDFYSIHVTKESTHPVKPLAQIAGNRYASGPVGKALSDACMGTIASFLSKYQDIIIEHQKVVKGNQKRL ESLRELAGKENLEYPSVTLPPQPHTKEGVDAYNEVIARVRMWVNLNLWQKLKLSRDDAKPLLRLKGFPSFPVVERRENEVDWWNTIN EVKKLIDAKRDMGRVFWSGVTAEKRNTILEGYNYLPNENDHKKREGSLENPKKPAKRQFGDLLLYLEKKYAGDWGKVFDEAWERIDK KIAGLTSHIEREEARNAEDAQSKAVLTDWLRAKASFVLERLKEMDEKEFYACEIQLQKWYGDLRGNPFAVEAENRVVDISGFSIGSD GHSIQYRNLLAWKYLENGKREFYLLMNYGKKGRIRFTDGTDIKKSGKWQGLLYGGGKAKVIDLTFDPDDEQUILPLAFGTROGREFI WNDLLSLETGLIKLANGRVIEKTIYNKKIGRDEPALFVALTFERREVVDPSNIKPVNLIGVDRGENIPAVIALTDPEGCPLPEFKDS SGGPTDILRIGEGYKEKQRAIQAAKEVEQRRAGGYSRKFASKSRNLADDMVRNSARDLFYHAVTHDAVLVFENLSRGFGRQGKRTFM TERQYTKMEDWLTAKLAYEGLTSKTYLSKTLAQYTSKTCSNCGFTITTADYDGMLVRLKKTSDGWATTLNNKELKAEGQITYYNRYK RQTVEKELSAELDRLSEESGNNDISKWTKGRRDEALFLLKKRFSHRPVQEQFVCLDCGHEVHADEQAALNIARSWLFLNSNSTEFKS

YKSGKQPFVGAWQAFYKRRLKEVWKPNA

CasX.1 Deltaproteobacteria nucleic acid sequence
(SEQ ID NO: 257):
```
at ggaaaagaga ataaacaaga tacgaaagaa actatcggcc gataatgcca caaagcctgt gagcaggagc ggccccatga aaacactcct tgtccgggtc atgacggacg acttgaaaaa agactggag aagcgtcgga aaaagccgga agttatgccg caggttattt caaataacgc agcaaacaat cttagaatgc tccttgatga ctatacaaag atgaaggagg cgatactaca agtttactgg caggaattta aggacgacca tgtgggcttg atgtgcaaat tgcccagcc tgcttccaaa aaaattgacc agaacaaact aaaaccggaa atggatgaaa aggaaatct aacaactgcc ggttttgcat gttctcaatg cggtcagccg ctatttgttt ataagcttga acaggtgagt gaaaaaggca aggcttatac aaattacttc ggccggtgta atgtggccga gcatgagaaa ttgattcttc ttgctcaatt aaaacctgaa aaagacagtg acgaagcagt gacatactcc cttggcaaat tcggccagag ggcattggac tttattcaa tccacgtaac aaaagaatcc accatccag taaagcccct ggcacagatt gcgggcaacc gctatgcaag cggacctgtt ggcaaggccc tttccgatgc ctgtatgggc actatagcca gtttctcttc gaaatatcaa gacatcatca tagaacatca aaaggttgtg aagggtaatc aaaagaggtt agagagtctc agggaattgg cagggaaaga aaatcttgag tacccatcgg ttacactgcc gccgcagccg catacgaaag aaggggttga cgcttataac gaagttattg caagggtacg tatgtgggtt aatcttaatc tgtggcaaaa gctgaagctc agccgtgatg acgcaaaacc gctactgcgg ctaaaaggat tcccatcttt cctgttgtg gagcggcgtg aaaacgaagt tgactggtgg aatacgatta atgaagtaaa aaaactgatt gacgctaaac gagatatggg acgggtattc tggagcggcg ttaccgcaga aaagagaaat accatccttg aaggatacaa ctatctgcca aatgagaatg accataaaaa gagagagggc agtttggaaa acccta agaa gcctgccaaa cgccagtttg gagacctctt gctgtatctt gaaaagaaat atgccggaga ctggggaaag
```

```
gtcttcgatg aggcatggga gaggatagat aagaaaatag ccggactcac aagccatata gagcgcgaag aagcaagaaa cgcggaagac gctcaatcca aagccgtact tacagactgg ctaagggcaa aggcatcatt tgttcttgaa agactgaagg aaatggatga aaaggaattc tatgcgtgtg aaatccaact tcaaaaatgg tatggcgatc ttcgaggcaa cccgtttgcc gttgaagctg agaatagagt tgttgatata agcgggtttt ctatcggaag cgatggccat tcaatccaat acagaaatct ccttgcctgg aaatatctgg agaacggcaa gcgtgaattc tatctgttaa tgaattatgg caagaaaggg cgcatcagat ttacagatgg aacagatatt aaaaagagcg gcaaatggca gggactatta tatgcggtg gcaaggcaaa ggttattgat ctgactttcg accccgatga tgaacagttg ataatcctgc cgctggcctt tggcacaagg caaggccgcg agtttatctg gaacgatttg ctgagtcttg aaacaggcct gataaagctc gcaaacggaa gagttatcga aaaaacaatc tataacaaaa aaatagggcg ggatgaaccg gctctattcg ttgccttaac atttgagcgc cgggaagttg ttgatccatc aaatataaag cctgtaaacc ttataggcgt tgaccgcggc gaaaacatcc cggcggttat tgcattgaca gaccctgaag gttgtccttt accggaattc aaggattcat caggggggccc aacagacatc ctgcgaatag gagaaggata taaggaaaag cagagggcta ttcaggcagc aaaggaggta gagcaaaggc gggctggcgg ttattcacgg aagtttgcat ccaagtcgag gaacctggcg gacgacatgg tgagaaattc agcgcgagac cttttttacc atgccgttac ccacgatgcc gtccttgtct ttgaaaacct gagcaggggg tttggaaggc agggcaaaag gaccttcatg acggaaagac aatatacaaa gatggaagac tggctgacag cgaagctcgc atacgaaggt cttacgtcaa aaacctacct ttcaaagacg ctggcgcaat atacgtcaaa aacatgctcc aactgcgggt tactataac gactgccgat tatgacggga tgttggtaag gcttaaaaag acttctgatg gatgggcaac taccctcaac aacaaagaat taaaagccga aggccagata acgtattata accggtataa aaggcaaacc gtggaaaaag aactctccgc agagcttgac aggctttcag aagagtcggg caataatgat atttctaagt ggaccaaggg tcgccgggac gaggcattat ttttgttaaa gaaaagattc agccatcggc ctgttcagga acagtttgtt tgcctcgatt gcggccatga agtccacgcc gatgaacagg cagccttgaa tattgcaagg tcatggcttt ttctaaactc aaattcaaca gaattcaaaa gttataaatc gggtaaacag cccttcgttg gtgcttggca ggccttttac aaaaggaggc ttaaagaggt atggaagccc aacgcctgat
```

The gene editor effector can also be CasY.1-CasY.6, examples of which are shown in FIG. 4. CasY.1-CasY.6 has TA PAM, and a shorter PAM sequence can be useful as there are less targeting limitations. The size of CasY.1-CasY.6 (1125 bp) provides the potential for two gRNA plus one siRNA or four gRNA in a delivery plasmid. CasY.1-CasY.6 can be derived from phyla radiation (CPR) bacteria, such as, but not limited to, katanobacteria, vogelbacteria, parcubacteria, komeilibacteria, or kerfeldbacteria The sequences for CasY.1-CasY.6 are below.

```
CasY.1 Candidatus katanobacteria amino acid sequence 1125aa
(SEQ ID NO: 258):
MRKKLFKGYILHNKRLVYTGKAAIRSIKYPLVAPNKTALNNLSEKIIYDYEHLFGPLNVASYARNSNRYSLVDFWIDSLRAGVIWQSK STSLIDLISKLEGSKSPSEKIFEQIDFELKNKLDKEQFKDIILLNTGIRSSSNVRSLRGRFLKCFKEEFRDTEEVIACVDKWSKDLIV EGKSILVSKQFLYWEEEFGIKIFPHFKDNHDLPKLTFFVEPSLEFSPHLPLANCLERLKKFDISRESLLGLDNNFSAFSNYFNELFNL LSRGEIKKIVTAVLAVSKSWENEPELEKRLHFLSEKAKLLGYPKLTSSWADYRMIIGGKIKSWHSNYTEQLIKVREDLKKHQIALDKL QEDLKKVVDSSLREQIEAQREALLPLLDTMLKEKDFSDDLELYRFILSDFKSLLNGSYQRYIQTEEERKEDRDVTKKYKDLYSNLRNI PRFFGESKKEQFNKFINKSLPTIDVGLKILEDIRNALETVSVRKPPSITEEYVTKQLEKLSRKYKINAFNSNRFKQITEQVLRKYNNG ELPKISEVFYRYPRESHVAIRILPVKISNPRKDISYLLDKYQISPDWKNSNPGEVVDLIEIYKLTLGWLLSCNKDFSMDFSSYDLKLF PEAASLIKNFGSCLSGYYLSKMIFNCITSEIKGMITLYTRDKFVVRYVTQMIGSNQKFPLLCLVGEKQTKNFSRNWGVLIEEKGDLGE EKNQEKCLIFKDKTDFAKAKEVEIFKNNIWRIRTSKYQIQFLNRLFKKTKEWDLMNLVLSEPSLVLEEEWGVSWDKDKLLPLLKKEKS CEERLYYSLPLNLVPATDYKEQSAEIEQRNTYLGLDVGEFGVAYAVVRIVRDRIELLSWGFLKDPALRKIRERVQDMKKKQVMAVFSS SSTAVARVREMAIHSLRNQIHSIALAYKAKIIYEISISNFETGGNRMAKIYRSIKVSDVYRESGADTLVSEMIWGKKNKQMGNHISSY ATSYTCCNCARTPFELVIDNDKEYEKGGDEFIFNVGDEKKVRGFLQKSLLGKTIKGKEVLKSIKEYARPPIREVLLEGEDVEQLLKRR

GNSYIYRCPFCGYKTDADIQAALNIACRGYISDNAKDAVKEGERKLDYILEVRKLWEKNGAVLRSAKFL
```

CasY.1 Candidatus katanobacteria nucleic acid sequence
(SEQ ID NO: 259):
at gcgcaaaaaa ttgtttaagg gttacatttt acataataag aggcttgtat atacaggtaa agctgcaata cgttctatta aatatccatt agtcgctcca aataaaacag ccttaaacaa tttatcagaa aagataattt atgattatga gcatttattc ggacctttaa atgtggctag ctatgcaaga aattcaaaca ggtacagcct tgtggatttt tggatagata gcttgcgagc aggtgtaatt tggcaaagca aaagtacttc gctaattgat ttgataagta agctagaagg atctaaatcc ccatcagaaa agatatttga acaaatagat tttgagctaa aaaataagtt ggataaagag caattcaaag atattattct tcttaataca ggaattcgtt ctagcagtaa tgttcgcagt ttgagggggc gctttctaaa gtgttttaaa gaggaattta gagataccga gaggttatc gcctgtgtag ataaatggag caaggacctt atcgtagagg gtaaaagtat actagtgagt aaacagtttc tttattggga agaagagttt ggtattaaaa ttttttcctca ttttaaagat aatcacgatt taccaaaact aacttttttt gtggagcctt ccttggaatt tagtccgcac ctccctttag ccaactgtct tgagcgtttg aaaaaattcg atatttcgcg tgaaagtttg ctcgggttag acaataattt ttcggccttt tctaattatt tcaatgagct ttttaactta ttgtccaggg gggagattaa aaagattgta acagctgtcc ttgctgtttc taaatcgtgg gagaatgagc cagaattgga aaagcgctta catttttga gtgagaaggc aaagttatta gggtaccta agcttacttc ttcgtgggcg gattatagaa tgattattgg cggaaaaatt aaatcttggc attctaacta taccgaacaa ttaataaaag ttagagagga cttaaagaaa catcaaatcg cccttgataa attacaggaa gatttaaaaa aagtagtaga tagctcttta agagaacaaa tagaagctca acgagaagct ttgcttcctt tgcttgatac catgttaaaa gaaaaagatt tttccgatga tttagagctt tacagattta tcttgtcaga ttttaagagt ttgttaaatg ggtcttatca aagatatatt caaacagaag aggagagaaa ggaggacaga gatgttacca aaaaatataa agatttatat agtaatttgc gcaacatacc tagattttt ggggaaagta aaaaggaaca attcaataaa tttataaata aatctctccc gaccatagat gttggtttaa aaatacttga ggatattcgt aatgctctag aaactgtaag tgttcgcaaa ccccccttcaa taacagaaga gtatgtaaca aagcaacttg agaagttaag tagaaagtac aaaattaacg ccttttaattc aaacagattt aaacaaataa ctgaacaggt gctcagaaaa tataataacg gagaactacc aaagatctcg gaggtttttt atagataccc gagagaatct catgtggcta taagaatatt acctgttaaa ataagcaatc caagaaagga tatatcttat cttctcgaca aatatcaaat tagccccgac tggaaaaaca gtaacccagg agaagttgta gatttgatag agatatataa attgacattg ggttggctct tgagttgtaa caaggatttt tcgatggatt tttcatcgta tgacttgaaa ctcttcccag aagccgcttc cctcataaaa aattttggct cttgcttgag tggttactat ttaagcaaaa tgatatttaa ttgcataacc agtgaaataa agggatgat tactttatat actagagaca agtttgttgt tagatatgtt acacaaatga taggtagcaa tcagaaattt cctttgttat gtttggtggg agagaaacag actaaaaact tttctcgcaa ctggggtgta ttgatagaag agaagggaga tttgggggag gaaaaaaacc aggaaaaatg tttgatattt aaggataaaa cagattttgc taaagctaaa gaagtagaaa ttttttaaaaa taatatttgg cgtatcagaa cctctaagta ccaaatccaa tttttgaata ggcttttaaa gaaaaccaaa gaatgggatt taatgaatct tgtattgagc gagcctagct tagtattgga ggaggaatgg ggtgtttcgt gggataaaga taaactttta cctttactga agaaagaaaa atcttgcgaa gaaagattat attactcact tccccttaac ttggtgcctg ccacagatta taaggagcaa tctgcagaaa tagagcaaag gaatacatat ttgggtttgg atgttggaga atttggtgtt gcctatgcag tggtaagaat agtaaggac agaatagagc ttctgtcctg gggattcctt aaggacccag ctcttcgaaa aataagagag cgtgtacagg atatgaagaa aaagcaggta atggcagtat tttctagctc ttccacagct gtcgcgcgag tacgagaaat ggctatacac tctttaagaa atcaaattca tagcattgct ttggcgtata aagcaaagat aatttatgag atatctataa gcaattttga gacaggtggt aatagaatgg ctaaaatata ccgatcctata aaggtttcag atgtttatag ggagagtggt gcggataccc tagtttcaga gatgatctgg ggcaaaaaga ataagcaaat gggaaaccat atatcttcct atgcgacaag ttacacttgt tgcaattgtg caagaaccccc ttttgaactt gttatagata atgacaagga atatgaaaag ggaggcgacg aatttatttt taatgttggc gatgaaaaga aggtaagggg gttttttacaa aagagtctgt taggaaaaac aattaaaggg aaggaagtgt tgaagtctat aaaagagtac gcaaggccgc

```
ctataaggga agtcttgctt gaaggagaag atgtagagca gttgttgaag aggagaggaa atagctatat ttatagatgc ccttttttgtg atataaaac tgatgcggat attcaagcgg cgttgaatat agcttgtagg ggatatattt cggataacgc aaaggatgct gtgaaggaag gagaaagaaa attagattac attttggaag ttagaaaatt gtgggagaag aatggagctg ttttgagaag cgccaaattt ttatagtt
```

CasY.2 Candidatus vogelbacteria amino acid sequence 1226aa
(SEQ ID NO: 260):

MQKVRKTLSEVHKNPYGTKVRNAKTGYSLQIERLSYTGKEGMRSFKIPLENKNKEVFDEFVKKIRNDYISQVGLLNLSDWYEHYQEKQ

EHYSLADFWLDSLRAGVIFAHKETEIKNLISKIRGDKSIVDKFNASIKKKHADLYALVDIKALYDFLTSDARRGLKTEEEFFNSKRNT

LFPKFRKKDNKAVDLWVKKFIGLDNKDKLNFTKKFIGFDPNPQIKYDHTFFFHQDINFDLERITTPKELISTYKKFLGKNKDLYGSDE

TTEDQLKMVLGFHNNHGAFSKYFNASLEAFRGRDNSLVEQIINNSPYWNSHRKELEKRIIFLQVQSKKIKETELGKPHEYLASFGGKF

ESWVSNYLRQEEEVKRQLFGYEENKKGQKKFIVGNKQELDKIIRGTDEYEIKAISKETIGLTQKCLKLLEQLKDSVDDYTLSLYRQLI

VELRIRLNVEFQETYPELIGKSEKDKEKDAKNKRADKRYPQIFKDIKLIPNFLGETKQMVYKKFIRSADILYEGINFIDQIDKQITQN

LLPCFKNDKERIEFTEKQFETLRRKYYLMNSSRFHHVIEGIINNRKLIEMKKRENSELKTFSDSKFVLSKLFLKKGKKYENEVYYTFY

INPKARDQRRIKIVLDINGNNSVGILQDLVQKLKPKWDDIIKKNDMGELIDAIEIEKVRLGILIALYCEHKFKIKKELLSLDLFASAY

QYLELEDDPEELSGTNLGRFLQSLVCSEIKGAINKISRTEYIERYTVQPMNTEKNYPLLINKEGKATWHIAAKDDLSKKKGGGTVAMN

QKIGKNFFGKQDYKTVFMLQDKRFDLLTSKYHLQFLSKTLDTGGGSWWKNKNIDLNLSSYSFIFEQKVKVEWDLTNLDHPIKIKPSEN

SDDRRLFVSIPFVIKPKQTKRKDLQTRVNYMGIDIGEYGLAWTIINIDLKNKKINKISKQGFIYEPLTHKVRDYVATIKDNQVRGTFG

MPDTKLARLRENAITSLRNQVHDIAMRYDAKPVYEFEISNFETGSNKVKVIYDSVKRADIGRGQNNTEADNTEVNLVWGKTSKQFGSQ

IGAYATSYICSFCGYSPYYEFENSKSGDEEGARDNLYQMKKLSRPSLEDFLOGNPVYKTFRDFDKYKNDQRLQKTGDKDGEWKTHRGN

TAIYACQKCRHISDADIQASYWIALKQVVRDFYKDKEMDGDLIQGDNKDKRKVNELNRLIGVHKDVPIINKNLITSLDINLL

CasY. Candidatus vogelbacteria nucleic acid sequence
(SEQ ID NO: 261):

```
a tggtattagg ttttcataat aatcacggcg cttttttctaa gtatttcaac gcgagcttgg aagcttttag ggggagagac aactccttgg ttgaacaaat aattaataat tctccttact ggaatagcca tcggaaagaa ttggaaaaga gaatcatttt tttgcaagtt cagtctaaaa aaataaaaga gaccgaactg ggaaagcctc acgagtatct tgcgagtttt ggcgggaagt ttgaatcttg ggtttcaaac tatttacgtc aggaagaaga ggtcaaacgt caacttttg gttatgagga gaataaaaaa ggccagaaaa aatttatcgt gggcaacaaa caagagctag ataaaatcat cagagggaca gatgagtatg agattaaagc gatttctaag gaaaccattg gacttactca gaaatgttta aaattacttg aacaactaaa agatagtgtc gatgattata cacttagcct atatcggcaa ctccatagtcg aattgagaat cagactgaat gttgaattcc aagaaactta tccggaatta atcggtaaga gtgagaaaga taaagaaaaa gatgcgaaaa ataaacgggc agacaagcgt tacccgcaaa tttttaagga tataaaatta atccccaatt ttctcggtga aacgaaacaa atggtatata gaaatttat tcgttccgct gacatccttt atgaaggaat aaattttatc gaccagatca taaacagat tactcaaaat tgttgccctt gttttaagaa cgacaaggaa cggattgaat ttaccgaaaa acaatttgaa actttacggc gaaaatacta tctgatgaat agttcccgtt ttcaccatgt tattgaagga ataatcaata ataggaaact tattgaaatg aaaaagagag aaaatagcga gttgaaaact ttctccgata gtaagtttgt tttatctaag ctttttctta aaaaaggcaa aaatatgaa atgaggtct attatacttt ttatataaat ccgaaagctc gtgaccagcg acggataaaa attgttcttg atataaatgg gaacaattca gtcggaattt tacaagatct tgtccaaaag ttgaaaccaa atgggacga catcataaag aaaaatgata tgggagaatt aatcgatgca atcgagattg agaaagtccg gctcggcatc ttgatagcgt tatactgtga gcataaattc aaaattaaaa aagaactctt gtcattagat ttgtttgcca gtgcctatca atatctagaa ttggaagatg accctgaaga actttctggg acaaacctag gtcggttttt acaatccttg gtctgctccg aaattaaagg tgcgattaat aaaataagca ggacagaata tatagagcgg tatactgtcc agccgatgaa tacggagaaa aactatcctt tactcatcaa taaggaggga aaagccactt ggcatattgc tgctaaggat gacttgtcca agaagaaggg tgggggcact gtcgctatga atcaaaaaat cggcaagaat ttttttggga aacaagatta taaaactgtg tttatgcttc aggataagcg gtttgatcta ctaaccctcaa agtatccactt gcagttttta
```

```
tctaaaactc ttgatactgg tggagggtct tggtggaaaa acaaaaatat tgatttaaat ttaagctctt attctttcat tttcgaacaa aaagtaaaag tcgaatggga tttaaccaat cttgaccatc ctataaagat taagcctagc gagaacagtg atgatagaag cttttcgta tccattcctt ttgttattaa accgaaacag acaaaaagaa aggatttgca aactcgagtc aattatatgg ggattgatat cggagaatat ggtttggctt ggacaattat taatattgat ttaaagaata aaaaaataaa taagatttca aaacaaggtt tcatctatga gccgttgaca cataaagtgc gcgattatgt tgctaccatt aaagataatc aggttagagg aacttttggc atgcctgata cgaaactagc cagattgcga gaaaatgcca ttaccagctt cgcaatcaa gtgcatgata ttgctatgcg ctatgacgcc aaaccggtat atgaatttga aatttccaat tttgaaacgg ggtctaataa agtgaaagta atttatgatt cggttaagcg agctgatatc ggccgaggcc agaataatac cgaagcagac aatactgagg ttaatcttgt ctgggggaag acaagcaaac aatttggcag tcaaatcggc gcttatgcga caagttacat ctgttcattt tgtggttatt ctccatatta tgaatttgaa aattctaagt cgggagatga agaagggct agagataatc tatatcagat gaagaaattg agtcgcccct ctcttgaaga tttcctccaa ggaaatccgg tttataagac atttagggat tttgataagt ataaaaacga tcaacggttg caaaagacgg gtgataaaga tggtgaatgg aaaacacaca gagggaatac tgcaatatac gcctgtcaaa agtgtagaca tatctctgat gcggatatcc aagcatcata ttggattgct ttgaagcaag ttgtaagaga ttttttataaa gacaaagaga tggatggtga tttgattcaa ggagataata aagacaagag aaaagtaaac gagcttaata gacttattgg agtacataaa gatgtgccta ataaaataa aaatttaata acatcactcg acataaactt actataga
```
CasY.3 Candidatus vogelbacteria amino acid sequence 1200aa
(SEQ ID NO: 262):
MKAKKSFYNQKRKFGKRGYRLHDERIAYSGGIGSMRSIKYELKDSYGIAGLRNRIADATISDNKWLYGNINLNDYLEWRSSKTDKQIE
DGDRESSLLGFWLEALRLGFVFSKQSHAPNDFNETALQDLFETLDDDLKHVLDRKKWCDFIKIGTPKTNDQGRLKKQIKNLLKGNKRE
EIEKTLNESDDELKEKINRIADVFAKNKSDKYTIFKLDKPNTEKYPRINDVQVAFFCHPDFEEITERDRTKTLDLIINRFNKRYEITE
NKKDDKTSNRMALYSLNQGYIPRVLNDLFLFVKDNEDDFSQFLSDLENFFSFSNEQIKIIKERLKKLKKYAEPIPGKPQLADKWDDYA
SDFGGKLESWYSNRIEKLKKIPESVSDLRNNLEKIRNVLKKQNNASKILELSQKIlEYIRDYGVSFEKPEIIKFSWINKTKDGQKKVF
YVAKMADREFIEKLDLWMADLRSQLNEYNQDNKVSFKKKGKKIEELGVLDFALNKAKKNKSTKNENGWQQKLSESIQSAPLFFGEGNR
VRNEEVYNLKDLLFSEIKNVENILMSSEAEDLKNIKIEYKEDGAKKGNYVLNVLARFYARFNEDGYGGWNKVKTVLENIAREAGTDFS
KYGNNNNRNAGRFYLNGRERQVFTLIKFEKSITVEKILELVKLPSLLDEAYRDLVNENKNHKLRDVIQLSKTIMALVLSHSDKEKQIG
GNYIHSKLSGYNALISKRDFISRYSVQTTNGTQCKLAIGKGKSKKGNEIDRYFYAFQFFKNDDSKINLKVIKNNSHKNIDFNDNENKI
NALQVYSSNYQIQFLDWFFEKHQGKKTSLEVGGSFTIAEKSLTIDWSGSNPRVGFKRSDTEEKRVFVSQPFTLIPDDEDKERRKERMI
KTKNRFIGIDIGEYGLAWSLIEVDNGDKNNRGIRQLESGFITDNQQQVLKKNVKSWRQNQIRQTFTSPDTKIARLRESLIGSYKNQLE
SLMVAKKANLSFEYEVSGFEVGGKRVAKIYDSIKRGSVRKKDNNSONDQSWGKKGINEWSFETTAAGTSQFCTHCKRWSSLAIVDIEE
YELKDYNDNLFKVKINDGEVRLLGKKGWRSGEKIKGKELFGPVKDAMRPNVDGLGMKIVRKYLKLDLRDWVSRYGNMAIFICPYVDC
HHISHADKQAAFNIAVRGYLKSVNPDRAIKHGDKGLSRDFLCQEEGKLNFEQIGLL CasY.3 Candidatus vogelbacteria nucleic acid sequence
(SEQ ID NO: 263):
```
atgaaa gctaaaaaaa gttttttataa tcaaaagcgg aagttcggta aagaggtta tcgtcttcac gatgaacgta tcgcgtattc aggagggatt ggatcgatgc gatctattaa atatgaattg aaggattcgt atggaattgc tgggcttcgt aatcgaatcg ctgacgcaac tatttctgat aataagtggc tgtacgggaa tataaatcta atgattatt tagagtggcg atcttcaaag actgacaaac agattgaaga cggagaccga gaatcatcac tcctgggttt tggctggaa gcgttacgac tgggattcgt gttttcaaaa caatctcatg ctccgaatga ttttaacgag accgctctac aagatttgtt tgaaactctt gatgatgatt tgaaacatgt tcttgatagg aaaaaatggt gtgactttat caagatagga cacctaaga caaatgacca aggtcgttta aaaaaacaaa tcaagaattt gttaaaagga aacaagagag aggaaattga aaaactctc aatgaatcag acgatgaatt gaaagagaaa ataaacagaa ttgccgatgt ttttgcaaaa aataagtctg ataaatacac aattttcaaa ttagataaac ccaatacgga aaaatacccc agaatcaacg atgttcaggt ggcgtttttt tgtcatcccg attttgagga
```

```
aattacagaa cgagatagaa caaagactct agatctgatc attaatcggt ttaataagag atatgaaatt accgaaaata
aaaaagatga caaaacttca aacaggatgg ccttgtattc cttgaaccag ggctatattc ctcgcgtcct gaatgattta
ttcttgtttg tcaaagacaa tgaggatgat tttagtcagt ttttatctga tttggagaat ttcttctctt tttccaacga
acaaattaaa ataataaagg aaaggttaaa aaaacttaaa aaatatgctg aaccaattcc cggaaagccg caacttgctg
ataaatggga cgattatgct tctgattttg gcggtaaatt ggaaagctgg tactccaatc gaatagagaa attaaagaag
attccggaaa gcgtttccga tctgcggaat aatttggaaa agatacgcaa tgttttaaaa aaacaaaata atgcatctaa
aatcctggag ttatctcaaa agatcattga atacatcaga gattatggag tttcttttga aaagccggag ataattaagt
tcagctggat aaataagacg aaggatggtc agaaaaaagt tttctatgtt gcgaaaatgg cggatagaga attcatagaa
aagcttgatt tatggatggc tgatttacgc agtcaattaa atgaatacaa tcaagataat aaagtttctt tcaaaaagaa
aggtaaaaaa atagaagagc tcggtgtctt ggattttgct cttaataaag cgaaaaaaaa taaaagtaca aaaaatgaaa
atggctggca acaaaaattg tcagaatcta ttcaatctgc cccgttattt tttggcgaag ggaatcgtgt acgaaatgaa
gaagtttata atttgaagga ccttctgttt tcagaaatca agaatgttga aaatatttta atgagctcgg aagcggaaga
cttaaaaaat ataaaaattg aatataaaga agatggcgcg aaaaaaggga actatgtctt gaatgtcttg gctagatttt
acgcgagatt caatgaggat ggctatggtg gttggaacaa agtaaaaacc gttttggaaa atattgcccg agaggcgggg
actgattttt caaaatatgg aaataataac aatagaaatg ccggcagatt ttatctaaac ggccgcgaac gacaagtttt
tactctaatc aagtttgaaa aaagtatcac ggtggaaaaa atacttgaat tggtaaaatt acctagccta cttgatgaag
cgtatagaga tttagtcaac gaaaataaaa atcataaatt acgcgacgta attcaattga gcaagacaat tatggctctg
gttttatctc attctgataa agaaaaacaa attggaggaa attatatcca tagtaaattg agcggataca atgcgcttat
ttcaaagcga gattttatct cgcggtatag cgtgcaaacg accaacggaa ctcaatgtaa attagccata ggaaaaggca
aaagcaaaaa aggtaatgaa attgacaggt atttctacgc tttttcaattt tttaagaatg acgacagcaa aattaattta
aaggtaatca aaaataattc gcataaaaac atcgatttca acgacaatga aaataaaatt aacgcattgc aagtgtattc
atcaaactat cagattcaat tcttagactg gttttttgaa aaacatcaag ggaagaaaac atcgctcgag gtcggcggat
cttttaccat cgccgaaaag agtttgacaa tagactggtc ggggagtaat ccgagagtcg gttttaaaag aagcgacacg
gaagaaaaga gggttttttgt ctcgcaacca tttacattaa taccagacga tgaagacaaa gagcgtcgta aagaaagaat
gataaagacg aaaaaccgtt ttatcggtat cgatatcggt gaatatggtc tggcttggag tctaatcgaa gtggacaatg
gagataaaaa taatagagga attagacaac ttgagagcgg ttttattaca gacaatcagc agcaagtctt aaagaaaaac
gtaaaatcct ggaggcaaaa ccaaattcgt caaacgttta cttcaccaga cacaaaaatt gctcgtcttc gtgaaagttt
gatcggaagt tacaaaaatc aactggaaag tctgatggtt gctaaaaaag caaatcttag ttttgaatac gaagtttccg
ggtttgaagt tgggggaaag agggttgcaa aaatatacga tagtataaag cgtgggtcgg tgcgtaaaaa ggataataac
tcacaaaatg atcaaagttg gggtaaaaag ggaattaatg agtggtcatt cgagacgacg gctgccggaa catcgcaatt
ttgtactcat tgcaagcggt ggagcagttt agcgatagta gatattgaag aatatgaatt aaaagattac aacgataatt
tatttaaggt aaaaattaat gatggtgaag ttcgtctcct tggtaagaaa ggttggagat ccggcgaaaa gatcaaaggg
aaagaattat ttggtcccgt caaagacgca atgcgcccaa atgttgacgg actagggatg aaaattgtaa aaagaaaata
tctaaaactt gatctccgcg attgggtttc aagatatggg aatatggcta ttttcatctg tccttatgtc gattgccacc
atatctctca tgcggataaa caagctgctt ttaatattgc cgtgcgaggg tatttgaaaa gcgttaatcc tgacagagca
ataaaacacg gagataaagg tttgtctagg gacttttttgt gccaagaaga gggtaagctt aattttgaac aaatagggtt
attatgaa
```

CasY.4 Candidatus parcubacteria amino acid sequence 1210aa
(SEQ ID NO: 264):
MSKRHPRISGVKGYRLHAQRLEYTGKSGAMRTIKYPLYSSPSGGRTVPREIVSAINDDYVGLYGLSNFDDLYNAEKRNEEKVYSVLD FWYDCVQYGAVFSYTAPGLLKNVAEVRGGSYELTKTLKGSHLYDELQIDKVIKFLNKKEISRANGSLDKLKKDIIDCFKAEYRERHK DQCNKLADDIKNAKKDAGASLGERQKKLFRDFFGISEQSENDKPSFTNPLNLTCCLLPFDTVNNNRNRGEVLFNKLKEYAQKLDKNE -continued GSLEMWEYIGIGNSGTAFSNFLGEGFLGRLRENKITELKKAMMDITDAWRGQEQEEELEKRLRILAALTIKLREPKFDNHWGGYRSD INGKLSSWLQNYINQTVKIKEDLKGHKKDLKKAKEMINRFGESDTKEEAVVSSLLESIEKIVPDDSADDEKPDIPAIAIYRRFLSDG RLTLNRFVQREDVQEALIKERLEAEKKKKPKKRKKKSDAEDEKETIDFKELFPHLAKPLKLVPNFYGDSKRELYKKYKNAAIYTDAL WKAVEKIYKSAFSSSLKNSFFDTDFDKDFFIKRLQKIFSVYRRFNTDKWKPIVKNSFAPYCDIVSLAENEVLYKPKQSRSRKSAAID KNRVRLPSTENIAKAGIALARELSVAGFDWKDLLKKEEHEEYIDLIELHKTALALLLAVTETQLDISALDFVENGTVKDFMKTRDGN LVLEGRFLEMFSQSIVFSELRGLAGLMSRKEFITRSAIQTMNGKQAELLYIPHEFQSAKITTPKEMSRAFLDLAPAEFATSLEPESL SEKSLLKLKQMRYYPHYFGYELTRTGQGIDGGVAENALRLEKSPVKKREIKCKQYKTLGRGQNKIVLYVRSSYYQTQFLEWFLHRPK NVQTDVAVSGSFLIDEKKVKTRWNYDALTVALEPVSGSERVFVSQPFTIFPEKSAEEEGQRYLGIDIGEYGIAYTALEITGDSAKIL DQNFISDPQLKTLREEVKGLKLDQRRGTFAMPSTKIARIRESLVHSLRNRIHHLALKHKAKIVYELEVSRFEEGKQKIKKVYATLKK ADVYSEIDADKNLQTTVWGKLAVASEISASYTSQFCGACKKLWRAEMQVDETITTQELIGTVRVIKGGTLIDAIKDFMRPPIFDEND

TPFPKYRDFCDKHHISKKMRGNSCLFICPFCRANADADIQASQTIALLRYVKEEKKVEDYFERFRKLKNIKVLGQMKKI

CasY.4 Candidatus parcubacteria nucleic acid sequence
(SEQ ID NO: 265):

atgagtaagc gacatcctag aattagcggc gtaaagggt accgtttgca tgcgcaacgg ctggaatata ccggcaaaag tggggcaatg cgaacgatta aatatcctct ttattcatct ccgagcggtg gaagaacggt tccgcgcgag atagtttcag caatcaatga tgattatgta gggctgtacg gtttgagtaa ttttgacgat ctgtataatg cggaaaagcg caacgaagaa aaggtctact cggttttaga ttttttggtac gactgcgtcc aatacggcgc ggttttttcg tatacagcgc cgggtctttt gaaaaatgtt gccgaagttc gcggggaag ctacgaactt acaaaaacgc ttaaaggag ccatttatat gatgaattgc aaattgataa agtaattaaa ttttgaata aaaaagaaat ttcgcagca aacgatcgc ttgataaact gaagaaagac atcattgatt gcttcaaagc agaatatcgg gaacgacata aagatcaatg caataaactg ctgatgata ttaaaaatgc aaaaaaagac gcgggagctt ctttagggga gcgtcaaaaa aaattattc gcgatttttt tggaatttca gagcagtctg aaaatgataa accgtcttt actaatccgc taaacttaac ctgctgtta ttgccttttg acacagtgaa taacaacaga aaccgcggcg aagttttgtt taacaagctc aaggaatatg ctcaaaaatt ggataaaaac gaagggtcgc ttgaaatgtg ggaatatatt ggcatcggga acagcggcac tgccttttct aattttttag gagaagggt tttgggcaga ttgcgcgaga ataaaattac agagctgaaa aaagccatga tggatattac agatgcatgg cgtgggcagg aacaggaaga agagttagaa aaacgtctgc ggatacttgc cgcgcttacc ataaaattgc gcgagccgaa atttgacaac cactggggag ggtatcgcag tgatataaac ggcaaattat ctagctggct tcagaattac ataaatcaaa cagtcaaaat caagaggac ttaaagggac acaaaaagga cctgaaaaaa gcgaaagaga tgataaatag gtttgggaa agcgacacaa aggaagaggc ggttgtttca tctttgcttg aaagcattga aaaaattgtt cctgatgata gcgctgatga cgagaaaccc gatattccag ctattgctat ctatcgccgc tttctttcgg atggacgatt aacattgaat cgctttgtcc aaagagaaga tgtgcaagag gcgctgataa aagaaagatt ggaagcggag aaaaagaaaa accgaaaaa gcgaaaaaag aaagtgacg ctgaagatga aaaagaaaca attgacttca aggagttatt tcctcatctt gccaaaccat taaattggt gccaaacttt acggcgaca gtaagcgtga gctgtacaag aaatataaga acgccgctat ttatacagat gctctgtgga agcagtgga aaaaatatac aaaagcgcgt tctcgtcgtc tctaaaaaat tcattttttg atacagattt tgataaagat ttttttatta gcggcttca gaaaattttt tcggtttatc gtcggtttaa tacagacaaa tggaaccga ttgtgaaaaa ctctttcgcg ccctattgcg acatcgtctc acttgcggag aatgaagttt tgtataaacc gaaacagtcg cgcagtagaa atctgccgc gattgataaa acagagtgc gtctcccttc cactgaaaat atcgcaaaag ctggcattgc cctcgcgcgg gagctttcag tcgcaggatt tgactggaaa gatttgttaa aaaagagga gcatgaagaa tacattgatc tcatagaatt gcacaaaacc gcgcttgcgc ttcttcttgc cgtaacagaa acacagcttg acataagcgc gttggatttt gtagaaaatg ggacggtcaa ggatttatg aaaacgcggg acggcaatct ggttttggaa gggcgttttc ttgaaatgtt ctcgcagtca attgtgtttt cagaattgcg cgggcttgcg ggtttaatga gccgcaagga atttatcact cgctccgcga ttcaaactat gaacggcaaa caggcggagc ttctctacat -continued

```
tccgcatgaa ttccaatcgg caaaaattac aacgccaaag gaaatgagca gggcgtttct tgaccttgcg cccgcggaat ttgctcacatc gcttgagcca gaatcgcttt cggagaagtc attattgaaa ttgaagcaga tgcggtacta tccgcattat tttggatatg agcttacgcg aacaggacag gggattgatg gtggagtcgc ggaaaatgcg ttacgacttg agaagtcgcc agtaaaaaaa cgagagataa aatgcaaaca gtataaaact ttgggacgcg gacaaaataa aatagtgtta tatgtccgca gttcttatta tcagacgcaa ttttttggaat ggtttttgca tcggccgaaa aacgttcaaa ccgatgttgc ggttagcggt tcgtttctta tcgacgaaaa gaaagtaaaa actcgctgga attatgacgc gcttacagtc gcgcttgaac cagtttccgg aagcgagcgg gtcttttgtct cacagccgtt tactattttt ccggaaaaaa gcgcagagga agaaggacag aggtatcttg gcatagacat cggcgaatac ggcattgcgt atactgcgct tgagataact ggcgacagtc caaagattct tgatcaaaat tttatttcag accccccagct taaaactctg cgcgaggagg tcaaaggatt aaaacttgac caaaggcgcg ggacatttgc catgccaagc acgaaaatcg cccgcatccg cgaaagcctt gtgcatagtt tgcggaaccg catacatcat cttgcgttaa agcacaaagc aaagattgtg tatgaattgg aagtgtcgcg tttttgaagag ggaaagcaaa aaattaagaa agtctacgct acgttaaaaa aagcggatgt gtattcagaa attgacgcgg ataaaaattt acaaacgaca gtatggggaa aattggccgt tgcaagcgaa atcagcgcaa gctatacaag ccagttttgt ggtgcgtgta aaaaattgtg gcgggcggaa atgcaggttg acgaaacaat tacaacccaa gaactaatcg gcacagttag agtcataaaa ggggggcactc ttattgacgc gataaaggat tttatgcgcc cgccgatttt tgacgaaaat gacactccat ttccaaaata tagagacttt tgcgacaagc atcacatttc caaaaaaatg cgtggaaaca gctgtttgtt catttgtcca ttctgccgcg caaacgcgga tgctgatatt caagcaagcc aaacaattgc gcttttaagg tatgttaagg aagagaaaaa ggtagaggac tactttgaac gatttagaaa gctaaaaaac attaaagtgc tcggacagat gaagaaaata tgatag
```

CasY.5 Candidatus komeilibacteria amino acid sequence 1192aa
(SEQ ID NO: 266):
MAESKQMQCRKCGASMKYEVIGLGKKSCRYMCPDCGNHTSARKIQNKKKRDKKYGSASKAQSQRIAVAGALYPDKKVQTIKTYKYPA
DLNGEVHDRGVAEKIEQAIQEDEIGLLGPSSEYACWIASQKQSEPYSVVDFWFDAVCAGGVFAYSGARLLSTVLQLSGEESVLRAAL
ASSPFVDDINLAQAEKFLAVSRRTGQDKLGKRIGECFAEGRLEALGIKDRMREFVQAIDVAQTAGQRFAAKLKIFGISQMPEAKQWN
NDSGLTVCILPDYYVPEENRADQLVVLLRRLREIAYCMGIEDEAGFEHLGIDPGALSNFSNGNPKRGFLGRLLNNDIIALANNMSAM
TPYWEGRKGELIERLAWLKHRAEGLYLKEPHFGNSWADHRSRIFSRIAGWLSGCAGKLKIAKDQISGVRTDLFLLKRLLDAVPQSAP
SPDFIASISALDRFLEAAESSQDPAEQVRALYAFHLNAPAVRSIANKAVQRSDSQEWLIKELDAVDHLEFNKAFPFFSDTGKKKKKG
ANSNGAPSEEEYTETESIQQPEDAEQEVNGQEGNGASKNQKKFQRIPRFFGEGSRSEYRILTEAPQYFDMFCNNMRAIFMQLESQPR
KAPRDFKCFLQNRLQKLYKQTFLNARSNKCRALLESVLISWGEFYTYGANEKKFRLRHEASERSSDPDYVVQQALEIARRLFLFGFE
WRDCSAGERVDLVEIHKKAISFLLAITQAEVSVGSYNWLGNSTVSRYLSVAGTDTLYGTQLEEFLNATVLSQMRGLAIRLSSQELKD
GFDVQLESSCQDNLQHLLVYRASRDLAACKRATCPAELDPKILVLPAGAFIASVMKMIERGDEPLAGAYLRHRPHSFGWQIRVRGVA
EVGMDQGTALAFQKPTESEPPFKIKPFSAQYGPVLWLNSSSYSQSQYLDGFLSQPKNWSMRVLPQAGSVRVEQRVALIWNLQAGKMRL
ERSGARAFFMPVPFSFRPSGSGDEAVLAPNRYLGLFPHSGGIEYAVVDVLDSAGFKILERGTIAVNGFSQKRGERQEEAHREKQRRG
ISDIGRKKPVQAEVDAANELHRKYTDVATRLGCRIVVQWAPQPKPGTAPTAQTVYARAVRTEAPRSGNQEDHARMKSSWGYTWSTYW
EKRKPEDILGISTQVYWTGGIGESCPAVAVALLGHIRATSTQTEWEKEEVVFGRLKKFFPS CasY.5 Candidatus komeilibacteria nucleic acid sequence
(SEQ ID NO: 267):

```
accaaccacc tattgcgtct ttttcgctca ttttagcaaa agtggctgtc tagacataca ggtggaaagg tgagagtaaa gacatggcct gaatagcgtc ctcgtcctcg tctagacata caggtggaaa ggtgagagta aagaccggag cactcatcct ctcactctat tttgtctaga catacaggtg gaaaggtgag agtaaagaca aaccgtgcca cactaaaccg atgagtctag acatacaggt ggaaaggtga gagtaaagac tcaagtaact acctgttctt tcacaagtct agacatacag gtggaaaggt gagagtaaag actcaagtaa ctacctgttc tttcacaagt ctagacctgc aggtggtaag gtgagagtaa agactcaagt aactacctgt tctttcacaa gtctagacct gcaggtggta aggtgagagt aaagactttt atcctcctct ctatgcttct gagtctagac atttaggtgg aaaggtgaga gtaaagactt gtggagatcc atgaacttcg gcagtctaga cctgcaggtg
```

-continued

```
gaaaggtgag agtaaagacg tccttcacac gatcttcctc tgttagtcta ggcctgcagg tggaaaggtg agagtaaaga
cgcataagcg taattgaagc tctctccggt ccagaccttg tcgcgcttgt gttgcgacaa aggcggagtc cgcaataagt
tcttttttaca atgttttttc cataaaaccg atacaatcaa gtatcggttt tgcttttttt atgaaaatat gttatgctat
gtgctcaaat aaaaatatca ataaaatagc gttttttga taatttatcg ctaaaattat acataatcac gcaacattgc
cattctcaca caggagaaaa gtcatggcag aaagcaagca gatgcaatgc cgcaagtgcg gcgcaagcat gaagtatgaa
gtaattggat tgggcaagaa gtcatgcaga tatatgtgcc cagattgcgg caatcacacc agcgcgcgca agattcagaa
caagaaaaag cgcgacaaaa agtatggatc cgcaagcaaa gcgcagagcc agaggatagc tgtggctggc gcgctttatc
cagacaaaaa agtgcagacc ataaagacct acaaataccc agcggatctg aatggcgaag ttcatgacag aggcgtcgca
gagaagattg agcaggcgat tcaggaagat gagatcggcc tgcttggccc gtccagcgaa tacgcttgct ggattgcttc
acaaaaacaa agcgagccgt attcagttgt agattttgg tttgacgcgg tgtgcgcagg cggagtattc gcgtattctg
gcgcgcgcct gctttccaca gtcctccagt tgagtggcga ggaaagcgtt ttgcgcgctg ctttagcatc tagcccgttt
gtagatgaca ttaatttggc gcaagcgaaa agttcctag ccgttagccg gcgcacaggc caagataagc taggcaagcg
cattggagaa tgtttcgcgg aaggccggct tgaagcgctt ggcatcaaag atcgcatgcg cgaattcgtg caagcgattg
atgtggccca accgcgggc cagcggttcg cggccaagct aaagatattc ggcatcagtc agatgcctga agccaagcaa
tggaacaatg attccgggct cactgtatgt attttgccgg attattatgt cccggaagaa aaccgcgcgg accagctggt
tgttttgctt cggcgcttac gcgagatcgc gtattgcatg ggaattgagg atgaagcagg atttgagcat ctaggcattg
accctggcgc tctttccaat ttttccaatg gcaatccaaa gcgaggattt ctcggccgcc tgctcaataa tgacattata
gcgctggcaa acaacatgtc agccatgacg ccgtattggg aaggcagaaa aggcgagttg attgagcgcc ttgcatggct
taaacatcgc gctgaaggat tgtatttgaa agagccacat ttcggcaact cctgggcaga ccaccgcagc aggattttca
gtcgcattgc gggctggctt tccggatgcg cgggcaagct caagattgcc aaggatcaga tttcaggcgt gcgtacggat
ttgtttctgc tcaagcgcct tctggatgcg gtaccgcaaa gcgcgccgtc gccggacttt attgcttcca tcagcgcgct
ggatcggttt ttggaagcgg cagaaagcag ccaggatccg gcagaacagg tacgcgcttt gtacgcgttt catctgaacg
cgcctgcggt ccgatccatc gccaacaagg cggtacagag gtctgattcc caggagtggc ttatcaagga actggatgct
gtagatcacc ttgaattcaa caaagcattt ccgttttttt cggatacagg aaagaaaaag aagaaggag cgaatagcaa
cggagcgcct tctgaagaag aatacacgga aacagaatcc attcaacaac cagaagatgc agagcaggaa gtgaatggtc
aagaaggaaa tggcgcttca aagaaccaga aaaagtttca gcgcattcct cgattttcg gggaagggtc aaggagtgag
tatcgaattt taacagaagc gccgcaatat tttgacatgt tctgcaataa tatgcgcgcg atctttatgc agctagagag
tcagccgcgc aaggcgcctc gtgatttcaa atgctttctg cagaatcgtt tgcagaagct ttacaagcaa acctttctca
atgctcgcag taataaatgc cgcgcgcttc tggaatccgt ccttatttca tggggagaat tttatactta tggcgcgaat
gaaaagaagt ttcgtctgcg ccatgaagcg agcgagcgca gctcggatcc ggactatgtg gttcagcagg cattggaaat
cgcgcgccgc cttttcttgt tcggatttga gtggcgcgat tgctctgctg gagagcgcgt ggatttggtt gaaatccaca
aaaaagcaat ctcatttttg cttgcaatca ctcaggccga ggtttcagtt ggttcctata actggcttgg gaatagcacc
gtgagccggt atctttcggt tgctggcaca gacacattgt acggcactca actgaggag ttttttgaacg ccacagtgct
ttcacagatg cgtgggctgg cgattcggct ttcatctcag gagttaaaag acggatttga tgttcagttg gagagttcgt
gccaggacaa tctccagcat ctgctggtgt atcgcgcttc gcgcgacttg gctgcgtgca aacgcgctac atgcccggct
gaattggatc cgaaaattct tgttctgccg gctggtgcgt ttatcgcgag cgtaatgaaa atgattgagc gtggcgatga
accattagca ggcgcgtatt tgcgtcatcg gccgcattca ttcggctggc agatacgggt tcgtggagtg gcggaagtag
gcatggatca gggcacagcg ctagcattcc agaagccgac tgaatcagag ccgtttaaaa taaagccgtt ttccgctcaa
tacggcccag tactttggct taattcttca tcctatagcc agagccagta tctggatgga ttttaagcc agccaaagaa
ttggtctatg cgggtgctac ctcaagccgg atcagtgcgc gtggaacagc gcgttgctct gatatggaat ttgcaggcag
```

-continued

```
gcaagatgcg gctggagcgc tctggagcgc gcgcgttttt catgccagtg ccattcagct tcaggccgtc tggttcagga gatgaagcag tattggcgcc gaatcggtac ttgggacttt ttccgcattc cggaggaata gaatacgcgg tggtggatgt attagattcc gcgggtttca aaattcttga gcgcggtacg attgcggtaa atggcttttc ccagaagcgc ggcgaacgcc aagaggaggc acacagagaa aaacagagac gcggaatttc tgatataggc cgcaagaagc cggtgcaagc tgaagttgac gcagccaatg aattgcaccg caaatacacc gatgttgcca ctcgtttagg gtgcagaatt gtggttcagt gggcgcccca gccaaagccg gcacagcgc cgaccgcgca acagtatac gcgcgcgcag tgcggaccga agccgcga tctggaaatc aagaggatca tgctcgtatg aaatcctctt ggggatatac ctggagcacc tattgggaga gcgcaaacc agaggatatt ttggcatct caacccaagt atactggacc ggcggtatag gcgagtcatg tcccgcagtc gcggttgcgc ttttggggca cattagggca acatccactc aaactgaatg gaaaaagag gaggttgtat tcggtcgact gaagaagttc tttccaagct agacgatctt tttaaaaact gggctgctgg ctatcgtatg gtcagtagct cttattttt tacttgatat atggtattat
```

CasY.6 Candidatus kerfeldbacteria amino acid sequence 1287aa
(SEQ ID NO: 268):
MKRILNSLKVAALRLLFRGKGSELVKTVKYPLVSPVQGAVEELAEAIRHDNLHLFGQKEIVDLMEKDEGTQVYSVVDFWLDTLRLGMF FSPSANALKITLGKFNSDQVSPFRKVLEQSPFFLAGRLKVEPAERILSVEIRKIGKRENRVENYAADVETCFIGQLSSDEKQSIQKLA NDIWDSKDHEEQRMLKADFFAIPLIKDPKAVTEEDPENETAGKQKPLELCVCLVPELYTRGFGSIADFLVQRLTLLRDKMSTDTAEDC LEYVGIEEEKGNGMNSLLGTFLKNLQGDGFEQIFQFMLGSYVGWQGKEDVLRERLDLLAEKVKRLPKPKFAGEWSGHRMFLHGQLKSW SSNFFRLFNETRELLESIKSDIQHATMLISYVEEKGGYHPQLLSQYRKLMEQLPALRTKVLDPEIEMTHMSEAVRSYIMIHKSVAGFL PDLLESLDRDKDREFLLSIFPRIPKIDKKTKEIVAWELPGEPEEGYLFTANNLFRNFLENPKHVPRFMAERIPEDWTRLRSAPVWFDG MVKQWQKVVNQLVESPGALYQFNESFLRQRLQAMLTVYKRDLQTEKFLKLLADVCRPLVDFFGLGGNDIIFKSCQDPRKQWQTVIPLS VPADVYTACEGLAIRLRETLGFEWKNLKGHEREDFLRLHQLLGNLLFWIRDAKLVVKLEDWMNNPCVQEYVEARKAIDLPLEIFGFEV PIFLNGYLFSELRQLELLLRRKSVMTSYSVKTTGSPNRLFQLVYLPLNPSDPEKKNSNNFQERLDTPTGLSRRFLDLTLDAFAGKLLT DPVTQELKTMAGFYDHLFGFKLPCKLAAMSNHPGSSSKMVVLAKPKKGVASNIGFEPIPDPAHPVFRVRSSWPELKYLEGLLYLPEDT PLTIELAETSVSCQSVSSVAFDLKNLTTILGRVGEFRVTADQPFKLTPIIPEKEESFIGKTYLGLDAGERSGVGFAIVTVDGDGYEVQ RLGVHEDTQLMALQQVASKSLKEPVFQPLRKGTFRQQERIRKSLRGCYWNFYHALMIKYRAKVVHEESVGSSGLVGQWLRAFQKDLKK ADVLPKKGGKNGVDKKKRESSAQDTLWGGAFSKKEEQQIAFEVQAAGSSQFCLKCGWWFQLGMREVNRVQESGVVLDWNRSIVTFLIE SSGEKVYGFSPQQLEKGFRPDIETFKKMVRDFMRPPMFDRKGRPAAAYERFVLGRRHRRYRFDKVFEERFGRSALFICPRVGCGNFDH

SSEQSAVVLALIGYIADKEGMSGKKLVYVRLAELMAEWKLKKLERSRVEEQSSAQ

CasY.6 Candidatus kerfeldbacteria nucleic acid sequence
(SEQ ID NO: 269):

```
atgaagag aattctgaac agtctgaaag ttgctgcctt gagacttctg tttcgaggca aaggttctga attagtgaag acagtcaaat atccattggt ttccccggtt caaggcgcgg ttgaagaact tgctgaagca attcggcacg acaacctgca cctttttggg cagaaggaaa tagtggatct tatggagaaa gacgaaggaa cccaggtgta ttcggttgtg gattttggt tggataccct gcgtttaggg atgttttct caccatcagc gaatgcgttg aaaatcacgc tgggaaaatt caattctgat caggtttcac cttttcgtaa ggttttggag cagtcacctt ttttcttgc gggtcgcttg aaggttgaac ctgcggaaag gatactttct gttgaaatca gaaagattgg taaagagaa acagagttg agaactatgc cgccgatgtg agacatgct tcattggtca gctttcttca gatgagaaac agagtatcca gaagctggca atgatatct gggatagcaa ggatcatgag gaacagagaa tgttgaaggc ggattttttt gctataccct ttataaaga ccccaaagct gtcacagaag aagatcctga aaatgaaacg gcgggaaaac agaaaccgct tgaattatgt gtttgtcttg ttcctgagtt gtataccga ggtttcggct ccattgctga ttttctggtt cagcgactta ccttgctgcg tgacaaaatg agtaccgaca cggcggaaga ttgcctcgag tatgttggca ttgaggaaga aaaggcaat ggaatgaatt ccttgctcgg cactttttg aagaacctgc agggtgatgg ttttgaacag atttttcagt ttatgcttgg gtcttatgtt ggctggcagg gaaggaaga tgtactgcgc gaacgattgg atttgctggc cgaaaaagtc aaaagattac caaagccaaa atttgccgga gaatggagtg gtcatcgtat gtttctccat ggtcagctga aagctggtc gtcgaatttc ttccgtcttt ttaatgagac gcgggaactt ctggaaagta tcaagagtga
```

-continued

```
tattcaacat gccaccatgc tcattagcta tgtggaagag aaaggaggct atcatccaca gctgttgagt cagtatcgga agttaatgga acaattaccg gcgttgcgga ctaaggtttt ggatcctgag attgagatga cgcatatgtc cgaggctgtt cgaagttaca ttatgataca caagtctgta gcgggatttc tgccggattt actcgagtct ttggatcgag ataaggatag ggaatttttg ctttccatct ttcctcgtat tccaaagata gataagaaga cgaaagagat cgttgcatgg gagctaccgg gcgagccaga ggaaggctat ttgttcacag caaacaacct tttccggaat tttcttgaga atccgaaaca tgtgccacga tttatggcag agaggattcc cgaggattgg acgcgtttgc gctcggcccc tgtgtggttt gatgggatgg tgaagcaatg gcagaaggtg gtgaatcagt tggttgaatc tccaggcgcc ctttatcagt tcaatgaaag ttttttgcgt caaagactgc aagcaatgct tacggtctat aagcgggatc tccagactga gaagtttctg aagctgctgg ctgatgtctg tcgtccactc gttgattttt tcggacttgg aggaaatgat attatcttca agtcatgtca ggatccaaga aagcaatggc agactgttat tccactcagt gtcccagcgg atgtttatac agcatgtgaa ggcttggcta ttcgtctccg cgaaactctt ggattcgaat ggaaaaatct gaaaggacac gagcgggaag atttttttacg gctgcatcag ttgctgggaa atctgctgtt ctggatcagg gatgcgaaac ttgtcgtgaa gctggaagac tggatgaaca atccttgtgt tcaggagtat gtggaagcac gaaaagccat tgatcttccc ttggagattt tcggatttga ggtgccgatt tttctcaatg gctatctctt ttcggaactg cgccagctgg aattgttgct gaggcgtaag tcggtgatga cgtcttacag cgtcaaaacg acaggctcgc caaataggct cttccagttg gtttacctac ctctaaaccc ttcagatccg gaaaagaaaa attccaacaa ctttcaggag cgcctcgata cacctaccgg tttgtcgcgt cgtttttctgg atcttacgct ggatgcattt gctggcaaac tcttgacgga tccggtaact caggaactga agacgatggc cggttttttac gatcatctct ttggcttcaa gttgccgtgt aaactggcgg cgatgagtaa ccatccagga tcctcttcca aaatggtggt tctggcaaaa ccaaagaagg gtgttgctag taacatcggc tttgaaccta ttcccgatcc tgctcatcct gtgttccggg tgagaagttc ctggccggag ttgaagtacc tggaggggtt gttgtatctt cccgaagata caccactgac cattgaactg gcggaaacgt cggtcagttg tcagtctgtg agttcagtcg ctttcgattt gaagaatctg acgactatct tgggtcgtgt tggtgaattc agggtgacgg cagatcaacc tttcaagctg acgcccatta ttcctgagaa agaggaatcc ttcatcggga agacctacct cggtcttgat gctggagagc gatctggcgt tggtttcgcg attgtgacgg ttgacggcga tgggtatgag gtgcagaggt tgggtgtgca tgaagatact cagcttatgg cgcttcagca agtcgccagc aagtctctta aggagccggt ttttccagcca ctccgtaagg gcacatttcg tcagcaggag cgcattcgca aaagcctccg cggttgctac tggaatttct atcatgcatt gatgatcaag taccgagcta aagttgtgca tgaggaatcg gtgggttcat ccggtctggt ggggcagtgg ctgcgtgcat ttcagaagga tctcaaaaag gctgatgttc tgcccaagaa gggtggaaaa aatggtgtag acaaaaaaaa gagagaaagc agcgctcagg ataccttatg gggaggagct ttctcgaaga aggaagagca gcagatagcc tttgaggttc aggcagctgg atcaagccag ttttgtctga agtgtggttg gtggtttcag ttggggatgc gggaagtaaa tcgtgtgcag gagagtggcg tggtgctgga ctggaaccgg tccattgtaa ccttcctcat cgaatcctca ggagaaaagg tatatggttt cagtcctcag caactggaaa aaggctttcg tcctgacatc gaaacgttca aaaaaatggt aagggatttt atgagacccc ccatgtttga tcgcaaaggt cggccggccg cggcgtatga aagattcgta ctgggacgtc gtcaccgtcg ttatcgcttt gataaagttt ttgaagagag atttggtcgc agtgctcttt tcatctgccc gcgggtcggg tgtgggaatt tcgatcactc cagtgagcag tcagccgttg tccttgccct tattggttac attgctgata aggaagggat gagtggtaag aagcttgttt atgtgaggct ggctgaactt atggctgagt ggaagctgaa gaaactggag agatcaaggg tggaagaaca gagctcggca caataa
```

Any of the gene editor effectors herein can also be tagged with Tev or any other suitable homing protein domains. According to Wolfs, et al. (Proc Natl Acad Sci USA. 2016 Dec. 27; 113(52):14988-14993. doi: 10.1073/pnas.1616343114. Epub 2016 Dec. 12), Tev is an RNA-guided dual active site nuclease that generates two noncompatible DNA breaks at a target site, effectively deleting the majority of the target site such that it cannot be regenerated.

In one preferred embodiment of the present invention, the CRISPR-associated endonuclease is a Cas9 nuclease. The Cas9 nuclease can be a sequence from *Staphylococcus aureus*. The Cas9 nuclease can also have a nucleotide sequence identical to the wild type *Streptococcus pyogenes* sequence. In some embodiments, the CRISPR-associated endonuclease can be a sequence from other species, for example other *Streptococcus* species, such as *Thermophiles*;

Psuedomonas aeruginosa, Escherichia coli, or other sequenced bacteria genomes and archaea, or other prokaryotic microoganisms. Alternatively, the wild type *Streptococcus pyogenes* Cas9 sequence can be modified. Preferably, the nucleic acid sequence is be codon optimized for efficient expression in mammalian cells, i.e., "humanized." A humanized Cas9 nuclease sequence can be for example, the Cas9 nuclease sequence encoded by any of the expression vectors listed in Genbank accession numbers KM099231.1 GI:669193757; KM099232.1 GI:669193761; or KM099233.1 GI:669193765. Alternatively, the Cas9 nuclease sequence can be for example, the sequence contained within a commercially available vector such as PX330 or PX260 from Addgene (Cambridge, Mass.). In some embodiments, the Cas9 endonuclease can have an amino acid sequence that is a variant or a fragment of any of the Cas9 endonuclease sequences of Genbank accession numbers KM099231.1 GI:669193757; KM099232.1 GI:669193761; or KM099233.1 GI:669193765 or Cas9 amino acid sequence of PX330 or PX260 (Addgene, Cambridge, Mass.).

The Cas9 nucleotide sequence can be modified to encode biologically active variants of Cas9, and these variants can have or can include, for example, an amino acid sequence that differs from a wild type Cas9 by virtue of containing one or more mutations (e.g., an addition, deletion, or substitution mutation or a combination of such mutations). One or more of the substitution mutations can be a substitution (e.g., a conservative amino acid substitution). For example, a biologically active variant of a Cas9 polypeptide can have an amino acid sequence with at least or about 50% sequence identity (e.g., at least or about 50%, 55%, 60%, 65%, 70%, 75%, 80%, 85%, 90%, 95%, 97%, 98%, or 99% sequence identity) to a wild type Cas9 polypeptide. Conservative amino acid substitutions typically include substitutions within the following groups: glycine and alanine; valine, isoleucine, and leucine; aspartic acid and glutamic acid; asparagine, glutamine, serine and threonine; lysine, histidine and arginine; and phenylalanine and tyrosine.

The amino acid residues in the Cas9 amino acid sequence can be non-naturally occurring amino acid residues. Naturally occurring amino acid residues include those naturally encoded by the genetic code as well as non-standard amino acids (e.g., amino acids having the D-configuration instead of the L-configuration). The present peptides can also include amino acid residues that are modified versions of standard residues (e.g. pyrrolysine can be used in place of lysine and selenocysteine can be used in place of cysteine). Non-naturally occurring amino acid residues are those that have not been found in nature, but that conform to the basic formula of an amino acid and can be incorporated into a peptide. These include D-alloisoleucine(2R,3S)-2amino-3-methylpentanoic acid and L-cyclopentyl glycine (S)-2-amino-2-cyclopentyl acetic acid. For other examples, one can consult textbooks or the worldwide web (a site is currently maintained by the California Institute of Technology and displays structures of non-natural amino acids that have been successfully incorporated into functional proteins).

The Cas9 nuclease sequence can be a mutated sequence. For example the Cas9 nuclease can be mutated in the conserved HNH and RuvC domains, which are involved in strand specific cleavage. For example, an aspartate-to-alanine (D10A) mutation in the RuvC catalytic domain allows the Cas9 nickase mutant (Cas9n) to nick rather than cleave DNA to yield single-stranded breaks, and the subsequent preferential repair through HDR22 can potentially decrease the frequency of unwanted InDel mutations from off-target double-stranded breaks.

In addition to the wild type and variant Cas9 endonucleases previously described, the present invention also encompasses CRISPR systems including "enhanced-specificity" *S. pyogenes* Cas9 variants (eSpCas9), which dramatically reduce off-target cleavage. These variants are engineered with alanine substitutions to neutralize positively charged sites in a groove that interacts with the non-target strand of DNA. This modification reduces interaction of Cas9 with the non-target strand, thereby encouraging re-hybridization between target and non-target strands. The effect of this modification is a requirement for more stringent Watson-Crick pairing between the gRNA and the target DNA strand, which limits off-target cleavage (Slaymaker, et al., 2015).

Especially preferred are three variants found to have the best cleavage efficiency and fewest off-target effects: SpCas9(K855a), SpCas9(K810A/K1003A/r1060A) (a.k.a. eSpCas9 1.0), and SpCas9(K848A/K1003A/R1060A) (a.k.a. eSPCas9 1.1). Techniques for cloning and inducing cellular expression of these enhanced-specificity variants can be found in Slaymaker, et al. (2015), which is incorporated herein in its entirety. The invention is by no means limited to these variants, and also encompasses all Cas9 variants disclosed by Slaymaker, et al. (2015).

In some embodiments, compositions of the invention can include a CRISPR-associated endonuclease polypeptide encoded by any of the nucleic acid sequences described above. Polypeptides can be generated by a variety of methods including, for example, recombinant techniques or chemical synthesis. Once generated, polypeptides can be isolated and purified to any desired extent by means well known in the art. For example, one can use lyophilization following, for example, reversed phase (preferably) or normal phase HPLC, or size exclusion or partition chromatography on polysaccharide gel media such as Sephadex G-25. The composition of the final polypeptide may be confirmed by amino acid analysis after degradation of the peptide by standard means, by amino acid sequencing, or by FAB-MS techniques.

In exemplary embodiments, the present invention includes an engineered CRISPR system including Cas9 and one or more gRNAs complementary to a JCV T-Ag sequence. An exemplary JCV genome sequence is the Mad-1 strain, NCBI reference sequence, GenBank number: NC_001699.1, public GI (Frisque et al, 1984). In the Mad 1 strain, the T-Ag coding region begins at nucleotide (nt) 5013 of the 5130 nt circular Mad-1 JCV genome. The nucleotide sequence of the T-Ag coding region is shown as SEQ ID NO: 13 in FIG. 1.

The composition of the present invention can also include siRNA, miRNAs (micro-RNAs), shRNAs (short hairpin RNAs), or RNAis (RNA interference) that target critical RNAs (viral mRNA) that translate (non-coding or coding) viral proteins involved with the formation of viral proteins and/or virions. The siRNA, miRNAs, shRNAs, or RNAi can be included in the expression vectors described herein along with the gene editing compositions. These RNA interference approaches are there to suppress the lytic and lysogenic cycles of viruses in order to prevent the virus from continuing to infect new cells. This then allows for 'zoning in' on the viral genes with the gene editors herein, in order to not fight continual re-infection. In cases like HIV, there exists FDA approved viral replication inhibitors, and the RNA interference approach is not necessarily needed. However, for most viruses such treatments do not exist, so the RNA interference approach to inhibit replication is critical. FIGS. 2A-2B describe lysogenic and lytic replication. FIG. 3 describes co-delivery of the gene editors, gRNAs and siRNA.

RNAi-mediated knockdown can reduce gene function. shRNAs or siRNAs are used to produce short double stranded RNA molecules which are processed by Dicer and single stranded RNA base-pairs with a target mRNA. Argonaute proteins then assist with mRNA degradation or translation inhibition. This results in post transcriptional down-regulation of gene expression but does not change the genetic code.

shRNA is double stranded RNA created from a DNA construct encoding a sequence of single stranded RNA and its complement that are separated by a stuffer fragment that allows the RNA molecule to fold back on itself to create a hairpin loop. shRNA can come in two different designs of a simple stem-loop and a microRNA adapted shRNA. A simple stem-loop shRNA has a 50-70 nucleotide transcript that forms a stem-loop structure consisting of a 19 to 29 bp region of double stranded RNA (the stem) bridged by a region of predominantly single-stranded RNA (the loop) and a dinucleotide 3' overhang. A microRNA adapted shRNA is greater than 250 nucleotides and more closely resembles native pri-microRNA molecules and consists of a shRNA stem structure which may include microRNA-like mismatches, bridged by a loop and flanked by 5' and 3' endogenous microRNA sequences.

Use of shRNA in RNAi instead of siRNA can be preferred as it has a low rate of degradation and turnover. siRNA can have variable transfection efficiencies that limits siRNA-mediated RNAi to only those cells capable of transfection. After the vector has integrated into the host genome, shRNA is transcribed in the nucleus by polymerase II or polymerase III. Also, shRNA can be delivered into mammalian cells through infection with viral vectors unlike siRNA. After processing by Drosha, pre-shRNA is exported from the nucleus by Exportin 5, then processed by Dicer, and loaded into the RNA-inducing silencing complex (RISC). The sense strand is degraded and the antisense strand directs RISC to mRNA with a complementary sequence. If the sequence is perfectly complementary, RISC cleaves the mRNA. If the sequence is not perfectly complementary, RISC represses translation of the mRNA. In either case, the target gene can be silenced. Most vector-based shRNA systems contain a selectable marker to allow for the elimination of cells that have not been successfully transfected or transduced, and maintenance of cells with sustained gene knockdown. The shRNA expression cassettes can also be incorporated into viral vector systems, including retrovirus, adeno-associated virus, adenovirus and lentivirus, which permit stable integration into and expression from the host genome. This permits shRNA delivery to cell lines that are refractory to transfection. Fluorescent markers (such as a Green or Red Fluorescent Protein [GFP or RFP]) can also be included for tracking cells expressing shRNAs.

shRNA has been used previously for gene therapy, such as the FANG vaccine (Gradalis, Inc.) that acts against TGF β1 and β2 in treating cancer, CEQ508 (Marina Biotech) that acts against β-catenin in treating Familial Adenomatous Polyposis, and shRNA-STMN1 (Gradalis, Inc.) that acts against stathmin 1 in treating cancer.

The present invention includes a method of eliminating a risk of JC virus activation in a patient during immunosuppressive therapy including the steps of: administering, to a patient latently or actively infected with JCV, an effective amount of a gene editing composition directed toward at least one target sequence in the JCV genome, cleaving the target sequence in the JCV genome, disrupting the JCV genome, eliminating the JCV infection, eliminating the risk of JCV virus activation, and administering an immunosuppressive therapy to the patient at a time chosen from before, during, and after administration of the gene editing composition. It should be understood that immunosuppressive therapy can be administered at different time points. PML may not occur until the patient is on immunotherapy, at which time the gene editing composition can be used while the patient remains on or is temporarily taken off of the immunosuppressive therapy. The gene editing composition can be any of those described above.

In a preferred embodiment, the method includes the steps of administering an effective amount of a pharmaceutical composition including an isolated nucleic acid encoding a CRISPR-associated endonuclease, and at least one isolated nucleic acid encoding at least gRNA including a spacer sequence complementary to a target sequence in a JCV DNA, expressing the CRISPR-associated endonuclease and the at least one gRNA in the cells of the patient, cleaving the target sequence in the JCV genome, disrupting the JCV genome, eliminating the JCV infection, eliminating the risk of JCV virus activation, and administering an immunosuppressive therapy to the patient at a time chosen from before, during, and after administration of the CRISPR-associated endonuclease. The CRISPR-associated endonuclease can be any of those gene editors described above. The siRNA, miRNAs, shRNAs, or RNAi can also be included in the composition.

Wollebo, et al. have disclosed a CRISPR/Cas9 system that can inhibit JCV replication and T-Ag expression in host cells, and to damage the integrity of the JCV genome. These effects caused the excision of both free episomal virus, and virus integrated into host genomes. Harmful off-target effects on healthy genes were not produced (Wollebo, et al., 2015, which is incorporated in its entirety). The Cas9 and gRNA compositions disclosed by Wollebo, et al. (2015), are employed in one embodiment of the method of the present invention.

A hypothetical exemplary treatment method is disclosed herein, in prophetic Example 1. This example includes the immunosuppressive multiple sclerosis drug natulizumab (Tysabri®), which carries 1/1000 to 13/1000 risk of inducing PML in patients seropositive for PML (Tysabri® Prescribing Information, Biogen Idec Inc., Cambridge, Mass.). The exemplary method is readily modified modifications for use with any immunosuppressive drug regimen, including, but not limited to, the drugs listed in Table 1.

The gRNAs in Example 1 are those disclosed by Wollebo, et al. (2015), but it will be understood that the present invention is not limited to those gRNAs. The gRNAs include gRNA spacer sequences complementary to the TM1, TM2 or TM3 regions JCV T-antigen sequence. Target sequences can extend from approximately 20 to 40 or more nts in length. It will be understood that, in different strains of JCV, or in mutational variants, sequences homologous to TM1, TM2, and TM3 can be readily identified by well known sequencing and genomics techniques.

An exemplary target sequence in TM1 includes SEQ ID NO: 1, or its complement on the antiparallel strand, SEQ ID NO: 2. The PAM sequence in each strand (shown in lower case bold in FIG. 1, and below) can be included in the target sequence, so that the target sequences can include SEQ ID NO: 3 or its complement on the antiparallel strand, SEQ ID NO: 4. A gRNA complementary to TM1, designated gRNA m1, can therefore include a spacer sequence complementary to SEQ ID NO: 1, SEQ ID NO: 2, SEQ ID NO: 3; or SEQ ID NO: 4.

The nucleotide sequences are as follows:

(SEQ ID NO: 1)
AAATGCAAAGAACTCCACCCTGATGAAGGTG (SEQ ID NO: 2)
AAATGCAAAGAACTCCACCCTGATGAAGGTGggg (SEQ ID NO: 3)
CACCTTTATCAGGGTGGAGTTCTTTGCATTT (SEQ ID NO: 4)
cccCACCTTTATCAGGGTGGAGTTCTTTGCATTT An exemplary target sequence in TM2 includes SEQ ID NO: 5, or its complement on the antiparallel strand, SEQ ID NO: 6. The PAM sequence in each strand can also be included in the target sequence, so that the target sequences can include SEQ ID NO: 7 or its complement on the antiparallel strand, SEQ ID NO: 8. A gRNA complementary to TM2, designated gRNA m2, can therefore include a spacer sequence complementary to SEQ ID NO: 5, SEQ ID NO: 6, SEQ ID NO: 7; or SEQ ID NO: 8.

The nucleotide sequences are as follows:

(SEQ ID NO: 5)
GATGAATGGGAATCCTGGTGGAATACATTTAATGAGAAGT (SEQ ID NO: 6)
GATGAATGGGAATCCTGGTGGAATACATTTAATGAGAAGTggg (SEQ ID NO: 7)
ACTTCTCATTAAATGTATTCCACCAGGATTCCCATTCATC (SEQ ID NO: 8)
cccACTTCTCATTAAATGTATTCCACCAGGATTCCCATTCATC An exemplary target sequence in TM3 includes SEQ ID NO: 9, or its complement on the antiparallel strand, SEQ ID NO: 10. The PAM sequence in each strand can also be included, so that the target sequences can include SEQ ID NO: 11, or its complement, SEQ ID NO: 12. A gRNA complementary to TM3, designated m3, can therefore include a spacer sequence complementary to SEQ ID NO: 9, SEQ ID NO: 10. SEQ ID NO: 11, or SEQ ID NO: 12.

THE nucleotide sequences are as follows:

(SEQ ID NO: 9)
AAGGTACTGGCTATTCAAGGGGCCAATAGACAG (SEQ ID NO: 10)
AAGGTACTGGCTATTCAAGGGGCCAATAGACAGtgg (SEQ ID NO: 11)
CTGTCTATTGGCCCCTTGAATAGCCAGTACCTT (SEQ ID NO: 12)
ccaCTGTCTATTGGCCCCTTGAATAGCCAGTACCTT It will be understood that the gRNAs of the present invention can also include additional 5' and/or 3' sequences that may or may not be complementary to a target sequence. The spacers of each gRNA can have less than 100% complementarity to its target sequence, for example 95% complementarity. It will also be understood that gRNAs other than those complementary to JCV large T-Ag coding regions are also within the scope of the present invention. This includes gRNAs complementary to target sequences within the regions encoding VP1, VP2, and VP3 and agnoprotein. Also within the scope of the invention are any existing additional sequences adjacent to different PAMs.

The gRNAs can be configured as a single sequence or as a combination of one or more different sequences, e.g., a multiplex configuration. Multiplex configurations can include combinations of two, three, or more different gRNAs. When the compositions are administered in an expression vector, the guide RNAs can be encoded by a single vector. Alternatively, multiple vectors can be engineered to each include two or more different guide RNAs. Especially useful care combinations of gRNAs that cause the excision of viral sequences between cleavage sites, resulting in the ablation of the JCV genome or JCV protein expression. The excised region can vary in size from a single nucleotide to several hundred nucleotides.

The RNA molecules (e.g., crRNA, tracrRNA, gRNA) may be engineered to comprise one or more modified nucleobases. For example, known modifications of RNA molecules can be found, for example, in Genes VI, Chapter 9 ("Interpreting the Genetic Code"), Lewin, ed. (1997, Oxford University Press, New York), and Modification and Editing of RNA, Grosjean and Benne, eds. (1998, ASM Press, Washington D.C.). Modified RNA components include the following: 2'-O-methylcytidine; $N^4$-methylcytidine; $N^4$-2'-O-dimethylcytidine; $N^4$-acetylcytidine; 5-methylcytidine; 5,2'-O-dimethylcytidine; 5-hydroxymethylcytidine; 5-formylcytidine; 2'-O-methyl-5-formaylcytidine; 3-methylcytidine; 2-thiocytidine; lysidine; 2'-O-methyluridine; 2thiouridine; 2-thio-2'-O-methyluridine; 3,2'-O-dimethyluridine; 3-(3-amino-carboxypropyl)uridine; 4-thiouridine; ribosylthymine; 5,2'-O-dimethyluridine; 5-methyl-2thiouridine; 5-hydroxyuridine; 5-methoxyuridine; uridine 5-oxyacetic acid; uridine 5-oxyacetic acid methyl ester; 5-carboxymethyluridine; 5-methoxycarbonylmethyluridine; 5methoxycarbonylmethyl-2'-O-methyluridine; 5-methoxycarbonylmethyl-2'-thiouridine; 5-carbamoylmethyluridine; 5-carbamoylmethyl-2'-O-methyluridine; 5-(carboxyhydroxymethyl) uridine; 5-(carboxyhydroxymethyl) uridinemethyl ester; 5-aminomethyl-2-thiouridine; 5methylaminomethyluridine; 5-methylaminomethyl-2-thiouridine; 5-methylaminomethyl-2selenouridine; 5-carboxymethylaminomethyluridine; 5-carboxymethylaminomethyl-2'-Omethyl-uridine; 5-carboxymethylaminomethyl-2-thiouridine; dihydrouridine; dihydroribosylthymine; 2'-methyladenosine; 2-methyladenosine; $N^6$-methyladenosine; $N^6,N^6$-dimethyladenosine; $N^6,2'$-O-trimethyladenosine; 2-methylthio-$N^6$ N-isopentenyladenosine; $N^6$-(cis-hydroxyisopentenyl)-adenosine; 2-methylthio-$N^6$-(cis-hydroxyisopentenyl)-adenosine; $N^6$-glycinylcarbamoyl)adenosine; $N^6$-threonylcarbamoyl adenosine; $N^6$-methyl-$N^6$threonylcarbamoyl adenosine; 2-methylthio-$N^6$-methyl-$N^6$-threonylcarbamoyl adenosine; $N^6$hydroxynorvalylcarbamoyl adenosine; 2-methylthio-$N^6$-hydroxnorvalylcarbamoyl adenosine; 2-O-ribosyladenosine (phosphate); inosine; 2'O-methyl inosine; 1-methyl inosine; 1; 2'-O-dimethyl inosine; 2'-O-methyl guanosine; 1-methyl guanosine; $N^2$-methyl guanosine; N2,N2-dimethyl guanosine; N2,2'-O-dimethyl guanosine; $N^2,N^2,2'$-O-trimethyl guanosine; 2'-O-ribosyl guanosine (phosphate); 7-methyl guanosine; $N^2$; 7-dimethyl guanosine; $N^2$; $N^2$; 7-trimethyl guanosine; wyosine; methylwyosine; under-modified hydroxywybutosine; wybutosine; 30 hydroxywybutosine; peroxywybutosine; queuosine; epoxyqueuosine; galactosyl-queuosine; mannosyl-queuosine; 7-cyano-7-deazaguanosine; arachaeosine [also called 7-formamido-7-deazaguanosine]; and 7-aminomethyl-7-deazaguanosine. The methods of the present invention or others in the art can be used to identify additional modified RNA molecules.

The gRNAs of the present invention are not limited to those complementary to sequences found within the TM1, TM2 or TM3 region of JCV T-antigen. Other regions of JCV can be targeted by CRISPR systems with suitably designed gRNAs. For CRISPR systems employing S. pyogenes Cas9, the PAM sequence can be AGG, TGG, CGG or GGG. Candidate target sequences can be identified by proximity to a 5' PAM such as AGG, TGG, CGG or GGG. Other Cas9 orthologs may have different PAM specificities. For example, Cas9 from S. Thermophiles requires 5'-NNAGAA for CRISPR 1 and 5'-NGGNG for CRISPR3) and Neiseria menigiditis requires 5'-NNNNGATT). The specific sequence of the gRNA may vary, but useful gRNA sequences will be those that minimize off target effects while achieving high efficiency and complete elimination of JCV. Efficiency and off target effects of candidate gRNAs can be determined by the assays disclosed in by Wollebo, et al. (2015).

The CRISPR/gene editor compositions are preferably administered as pharmaceutical compositions, which can be prepared in a variety of ways known to one of ordinary skill in the art. Preferably, the CRISPR/gene editor compositions are encoded in expression vectors, which are formulated in compositions for administration to a patient, or in some cases, for treatment of cultured patient cells for adoptive transfer to the patient. These compositions can be prepared in a manner well known in the pharmaceutical art, and can be administered by a variety of routes. Since latent JCV can dwell in both glial cells of the brain and other CNS tissues, and in a variety of lymphoid and nonlymphoid peripheral tissues, delivery by multiple routes, both local and systemic, may be desirable.

Administration may be topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), ocular, oral or parenteral. Methods for ocular delivery can include topical administration (eye drops), subconjunctival, periocular or intravitreal injection or introduction by balloon catheter or ophthalmic inserts surgically placed in the conjunctival sac. Parenteral administration includes intravenous, intraarterial, subcutaneous, intraperitoneal or intramuscular injection or infusion or catheterization; or intracranial, e.g., intrathecal or intraventricular administration, for example by means of a cannula. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids, powders, and the like. Conventional pharmaceutical carriers, aqueous, powder or oily bases, thickeners and the like may be necessary or desirable. Glial and mesenchymal cells that have been transduced with gene editing components may be used to conduct these components to sites in the CNS (Lee, et al., 2013, San Sebastian, et al., 2013)

The present invention also includes pharmaceutical compositions which contain, as the active ingredient, nucleic acids, vectors, exosomes, and nanoclews described herein, in combination with one or more pharmaceutically acceptable carriers. We use the terms "pharmaceutically acceptable" (or "pharmacologically acceptable") to refer to molecular entities and compositions that do not produce an adverse, allergic or other untoward reaction when administered to an animal or a human, as appropriate. The term "pharmaceutically acceptable carrier," as used herein, includes any and all solvents, dispersion media, coatings, antibacterial, isotonic and absorption delaying agents, buffers, excipients, binders, lubricants, gels, surfactants and the like, that may be used as media for a pharmaceutically acceptable substance. In making the compositions of the invention, the active ingredient is typically mixed with an excipient, diluted by an excipient or enclosed within such a carrier in the form of, for example, a capsule, tablet, sachet, paper, or other container. When the excipient serves as a diluent, it can be a solid, semisolid, or liquid material (e.g., normal saline), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), lotions, creams, ointments, gels, soft and hard gelatin capsules, suppositories, sterile injectable solutions, and sterile packaged powders. As is known in the art, the type of diluent can vary depending upon the intended route of administration. The resulting compositions can include additional agents, such as preservatives. In some embodiments, the carrier can be, or can include, a lipid-based or polymer-based colloid. In some embodiments, the carrier material can be a colloid formulated as a liposome, a hydrogel, a microparticle, a nanoparticle, or a block copolymer micelle. As noted, the carrier material can form a capsule, and that material may be a polymer-based colloid. Further description of exemplary pharmaceutically acceptable carriers and diluents, as well as pharmaceutical formulations, can be found in *Remington's Pharmaceutical Sciences*, a standard text in this field, and in USP/NF. Other substances may be added to the compositions to stabilize and/or preserve the compositions.

The term "effective amount" of a pharmaceutical composition, as used herein, refers to any amount that induces a desired response while not inducing significant toxicity in the patient. For the present invention, the desired effect of a gene editing composition is the elimination of JCV from host tissues. The amount can be determined by assessing a patient's response after administration of a known amount of a particular composition. In addition, the level of toxicity, if any, can be determined by assessing a patient's clinical symptoms before and after administering a known amount of a particular composition. It is noted that the effective amount of a particular composition administered to a patient can be adjusted according to a desired outcome as well as the patient's response and level of toxicity. Significant toxicity can vary for each particular patient and depends on multiple factors including, without limitation, the patient's disease state, age, and tolerance to side effects.

The nucleic acid sequences of the invention can be delivered to an appropriate cell of a subject. This can be achieved by, for example, the use of a polymeric, biodegradable microparticle or microcapsule delivery vehicle, sized to optimize phagocytosis by phagocytic cells such as macrophages. For example, PLGA (poly-lacto-co-glycolide) microparticles approximately 1-10 μm in diameter can be used. The polynucleotide is encapsulated in these microparticles, which are taken up by macrophages and gradually biodegraded within the cell, thereby releasing the polynucleotide. Once released, the DNA is expressed within the cell. A second type of microparticle is intended not to be taken up directly by cells, but rather to serve primarily as a slow-release reservoir of nucleic acid that is taken up by cells only upon release from the micro-particle through biodegradation. These polymeric particles should therefore be large enough to preclude phagocytosis (i.e., larger than 5 μm and preferably larger than 20 μm). Another way to achieve uptake of the nucleic acid is using liposomes, prepared by standard methods. The nucleic acids can be incorporated alone into these delivery vehicles or co-incorporated with tissue-specific antibodies, for example antibodies that target cell types that are common latently infected reservoirs of HIV infection, for example, brain macrophages, microglia, astrocytes, and gut-associated lymphoid cells. Alternatively, one can prepare a molecular complex composed of a plasmid or other vector attached to poly-L-lysine by electrostatic or covalent forces. Poly-L-lysine binds to a ligand that can bind to a receptor on target cells. Delivery of "naked DNA" (i.e., without a delivery vehicle) to an intramuscular, intradermal, or subcutaneous site, is another means to achieve in vivo expression. In the relevant polynucleotides (e.g., expression vectors) the nucleic acid sequence encoding an isolated nucleic acid sequence comprising a sequence encoding a CRISPR-associated endonuclease and a guide RNA is operatively linked to a promoter or enhancer-promoter combination. Promoters and enhancers are described above.

In some embodiments, the compositions of the invention can be formulated as a nanoparticle, for example, nanoparticles comprised of a core of high molecular weight linear polyethylenimine (LPEI) complexed with DNA and surrounded by a shell of polyethyleneglycol-modified (PEGylated) low molecular weight LPEI.

The nucleic acids and vectors may also be applied to a surface of a device (e.g., a catheter) or contained within a pump, patch, or other drug delivery device. The nucleic acids and vectors of the invention can be administered alone, or in a mixture, in the presence of a pharmaceutically acceptable excipient or carrier (e.g., physiological saline). The excipient or carrier is selected on the basis of the mode and route of administration. Suitable pharmaceutical carriers, as well as pharmaceutical necessities for use in pharmaceutical formulations, are described in *Remington's Pharmaceutical Sciences* (E. W. Martin), a well-known reference text in this field, and in the USP/NF (United States Pharmacopeia and the National Formulary).

In some embodiments, the compositions can be formulated as a nanoparticle encapsulating a nucleic acid encoding Cas9 or a variant Cas9, or Cpf1, or a variant of Cpf1, C2c1, C2c3, TevCas9, Archaea Cas9, CasY.1-CasY.6, and CasX gRNAs, Argonaute endonuclease gDNAs, or any other effective g-RNA guided DNA endonuclease; and at least one gRNA sequence complementary to a target HIV; or it can include a vector encoding these components. Alternatively, the compositions can be formulated as a nanoparticle encapsulating the CRISPR-associated endonuclease the polypeptides encoded by one or more of the nucleic acid compositions of the present invention.

Preferably, gene editing treatments are administered only to patients determined to be in need of the treatments, that is, patients determined to harbor latent JCV infection. The determination can be made by any effective screening test known in the art. ELISA assays for anti-JCV antibodies, and quantitative PCR for JCV DNA, in blood, serum, CSF, or other body fluids are preferred. An inclusion body diagnostic assay can be alternatively employed. Thus, the method of the present invention can include, prior to the administering step, the step of prior to step of administering, the step of screening a patient for latent or active JCV infection.

It is also preferable that a patient who is identified as having a latent or active JCV infection be monitored to ensure that the infection is resolved prior to the commencement of immunosuppressive therapy. If immunosuppressive therapy is delivered over a long course, it is also desirable to monitor the patient for the recurrence of JCV infection, for example, by reactivation of small, untreated reservoirs of latent virus. Monitoring can be performed by any suitable method, such as the ELISA and PCR methods previously stated. Thus, the method of the present invention can also include, at any point after the step of disrupting the JCV genome, the step of determining that the JCV infection has been resolved.

Dosage, toxicity, and therapeutic efficacy the gene editing compositions can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. The Cas9/gRNA compositions that exhibit high therapeutic indices are preferred. While Cas9/gRNA compositions that exhibit off target effects or other toxic side effects may be used, care should be taken to design a delivery system that targets such compositions to the site of affected tissue in order to minimize potential damage to uninfected cells and, thereby, reduce side effects. Restriction of side effects can also be accomplished by including in expression vectors one or more tissue specific promoters. Additionally, in order to enhance the in vivo half-life of the administered compound, the compositions may be encapsulated, introduced into the lumen of liposomes, prepared as a colloid, or other conventional techniques may be employed which provide an extended serum half-life of the compositions. A variety of methods are available for preparing liposomes, as described in, e.g., Szoka, et al., U.S. Pat. Nos. 4,235,871, 4,501,728 and 4,837,028 each of which is incorporated herein by reference. Furthermore, one may administer the drug in a targeted drug delivery system, for example, in a liposome coated with a tissue specific antibody. The liposomes will be targeted to and taken up selectively by the tissue.

The data obtained from the cell culture assays and animal studies can be used in formulating a range of dosage for use in humans. The dosage of such compositions lies generally within a range of circulating concentrations that include the $ED_{50}$ with little or no toxicity. The dosage may vary within this range depending upon the dosage form employed and the route of administration utilized. For any composition used in the method of the invention, the therapeutically effective dose can be estimated initially from cell culture assays.

Vectors. The present invention includes a vector comprising one or more cassettes for expression of CRISPR components such as one or more gRNAs and a Cas endonuclease such as Cas9. The vector can be any vector that is known in the art and is suitable for expressing the desired expression cassette. A number of vectors are known to be capable of mediating transfer of gene products to mammalian cells, as is known in the art and described herein. A "vector" (sometimes referred to as gene delivery or gene transfer "vehicle") refers to a macromolecule or complex of molecules comprising a polynucleotide to be delivered to a host cell, either in vitro or in vivo. The polynucleotide to be delivered may comprise a coding sequence of interest in gene therapy.

A preferred vector is a lentiviral vector. Lentiviral vectors have the advantage of providing efficient transduction of both proliferating and resting cells, stable expression of delivered genes by integration into host chromatin, and the absence of interference from preexisting viral immunity. In experiments disclosed in Wollebo, et al., (2015), drug-inducible lentiviral expression vectors for Cas9/gRNA components were shown to be effective in ablating JCV T-Ag expression in infected cells. In an exemplary configuration, host cells were stably transduced with Cas9 or another suitable CRISPR endonuclease in doxycycline inducible lentiviral vector. When elimination of JCV was desired, the host cells were transduced with one or more gRNAs and treated with doxycycline, to activate expression of Cas9, to cause guided cleavage of the JCV genome and inactivation of virus. Alternatively, one or more gRNAs can be transduced stably, in a drug-inducible manner, or both a CRISPR associated endonuclease and gRNAs can be so transduced. In a clinical situation, this treatment could be used for patients at risk of JCV infection, with the CRISPR components being activated upon evidence of initial or recurrent infection.

Therefore, the present invention encompasses a vector composition for use in eliminating JCV from a host cell. The vector composition includes at least one isolated nucleic acid sequence encoding a CRISPR-associated endonuclease, and at least one gRNA having a spacer sequence complementary to a target sequence in a JCV DNA. The isolated nucleic acid sequences are included in at least one expression vector, which induces the expression of the CRISPR-associated endonuclease and the at least one gRNA in a host cell.

The present invention is by no means limited to the plasmid and lentiviral vectors described in Examples 1-2. Other preferred vectors include adenovirus vectors and adeno-associated virus vectors. These have the advantage of not integrating into host cell DNA. Adenoviruses have the additional advantage of having a large packaging capacity (Ding, et al., 2014). Many other recombinant viral vectors are also suitable, including, but not limited to, vesicular stomatitis virus (VSV) vectors, pox virus vectors, and retroviral vectors.

A "recombinant viral vector" refers to a viral vector comprising one or more heterologous gene products or sequences. Since many viral vectors exhibit size constraints associated with packaging, the heterologous gene products or sequences are typically introduced by replacing one or more portions of the viral genome. Such viruses may become replication defective, requiring the deleted function(s) to be provided in trans during viral replication and encapsidation (by using, e.g., a helper virus or a packaging cell line carrying gene products necessary for replication and/or encapsidation). Modified viral vectors in which a polynucleotide to be delivered is carried on the outside of the viral particle have also been described.

Retroviral vectors include Moloney murine leukemia viruses and HIV-based viruses. One preferred HIV-based viral vector comprises at least two vectors wherein the gag and pol genes are from an HIV genome and the env gene is from another virus. DNA viral vectors are preferred. These vectors include pox vectors such as orthopox or avipox vectors, herpesvirus vectors such as a herpes simplex I virus (HSV) vector.

Pox viral vectors introduce the gene into the cells cytoplasm. Avipox virus vectors result in only a short term expression of the nucleic acid. Adenovirus vectors, adeno-associated virus vectors and herpes simplex virus (HSV) vectors may be an indication for some invention embodiments. The adenovirus vector results in a shorter term expression (e.g., less than about a month) than adeno-associated virus, in some embodiments, may exhibit much longer expression. The particular vector chosen will depend upon the target cell and the condition being treated. The selection of appropriate promoters can readily be accomplished. In some embodiments, a high expression promoter can be used. An example of a suitable promoter is the 763-base-pair cytomegalovirus (CMV) promoter. The Rous sarcoma virus (RSV) and MMT promoters may also be used. Certain proteins can expressed using their native promoter. Other elements that can enhance expression can also be included such as an enhancer or a system that results in high levels of expression such as a tat gene and tar element. This cassette can then be inserted into a vector, e.g., a plasmid vector such as, pUC19, pUC118, pBR322, or other known plasmid vectors, that includes, for example, an E. coli origin of replication. The plasmid vector may also include a selectable marker such as the β-lactamase gene for ampicillin resistance, provided that the marker polypeptide does not adversely affect the metabolism of the organism being treated. The cassette can also be bound to a nucleic acid binding moiety in a synthetic delivery system, such as the system disclosed in WO 95/22618.

Another delivery method is to use single stranded DNA producing vectors which can produce the expressed products intracellularly. See for example, Chen et al, *Bio Techniques*, 34: 167-171 (2003), which is incorporated herein, by reference, in its entirety.

Expression may be controlled by any promoter/enhancer element known in the art that is functional in the host selected for expression. Besides the promoters described in the examples section, other promoters which may be used for gene expression include, but are not limited to, cytomegalovirus (CMV) promoter, the SV40 early promoter region, the promoter contained in the 3' long terminal repeat of Rous sarcoma virus, the herpes thymidine kinase promoter, the regulatory sequences of the metallothionein gene; prokaryotic expression vectors such as the beta-lactamase, or the tac promoter; promoter elements from yeast or other fungi such as the Gal 4 promoter, the ADC (alcohol dehydrogenase) promoter, PGK (phosphoglycerol kinase) promoter, alkaline phosphatase promoter; and the animal transcriptional control regions, which exhibit tissue specificity and have been utilized in transgenic animals: elastase I gene control region which is active in pancreatic acinar cells; insulin gene control region which is active in pancreatic beta cells, immunoglobulin gene control region which is active in lymphoid cells, mouse mammary tumor virus control region which is active in testicular, breast, lymphoid and mast cells, albumin gene control region which is active in liver, alpha-fetoprotein gene control region which is active in liver, alpha 1-antitrypsin gene control region which is active in the liver, beta-globin gene control region which is active in myeloid cells, myelin basic protein gene control region which is active in oligodendrocyte cells in the brain, myosin light chain-2 gene control region which is active in skeletal muscle, and gonadotropic releasing hormone gene control region which is active in the hypothalamus.

A wide variety of host/expression vector combinations may be employed in expressing the nucleic acid sequences of this invention. Useful expression vectors, for example, may consist of segments of chromosomal, non-chromosomal and synthetic DNA sequences. Suitable vectors include derivatives of SV40 and known bacterial plasmids, e.g., E. coli plasmids col E1, pCR1, pBR322, pMal-C2, pET, pGEX, pMB9 and their derivatives, plasmids such as RP4; phage DNAs, e.g., the numerous derivatives of phage 1, e.g., NM989, and other phage DNA, e.g., M13 and filamentous single stranded phage DNA; yeast plasmids such as the 2p plasmid or derivatives thereof, vectors useful in eukaryotic cells, such as vectors useful in insect or mammalian cells;

vectors derived from combinations of plasmids and phage DNAs, such as plasmids that have been modified to employ phage DNA or other expression control sequences; and the like.

If desired, the polynucleotides of the invention may also be used with a microdelivery vehicle such as cationic liposomes and other lipid-containing complexes, and other macromolecular complexes capable of mediating delivery of a polynucleotide to a host cell.

Vectors can also comprise other components or functionalities that further modulate gene delivery and/or gene expression, or that otherwise provide beneficial properties to the targeted cells. Such other components include, for example, components that influence binding or targeting to cells (including components that mediate cell-type or tissue-specific binding); components that influence uptake of the vector nucleic acid by the cell; components that influence localization of the polynucleotide within the cell after uptake (such as agents mediating nuclear localization); and components that influence expression of the polynucleotide. Such components can also include markers, such as detectable and/or selectable markers that can be used to detect or select for cells that have taken up and are expressing the nucleic acid delivered by the vector. Such components can be provided as a natural feature of the vector (such as the use of certain viral vectors which have components or functionalities mediating binding and uptake), or vectors can be modified to provide such functionalities. Other vectors include those described by Chen et al.; BioTechniques, 534: 167-171 (2003). A large variety of such vectors are known in the art and are generally available.

Delivery of vectors can also be mediated by exosomes. Exosomes are lipid nanovesicles released by many cell types. They mediate intercellular communication by transporting nucleic acids and proteins between cells. Exosomes contain RNAs, miRNAs, and proteins derived from the endocytic pathway. They may be taken up by target cells by endocytosis, fusion, or both. Typically, the receipt of endosomal contents alters the functions of the receiving cells (Lee, et al., 2012).

Exosomes can be harnessed to deliver nucleic acids to target cells. In a preferred method, exosomes are produced in vitro by producer cells, purified, and loaded with a nucleic acid cargo by electroporation, or by lipid transfection agents (Marcus and Leonard, 2013, Shtam, et al., 2013). The cargo can include expression constructs for a Cas endonuclease and one or more gRNAs. Suitable techniques can be found in Kooijmans, et al. (2012), Lee, et al. (2012), Marcus and Leonard (2013), Shtam, et al. (2013), or references therein. An exemplary kit for producing and loading exosomes is the ExoFect™ kit (System Biosciences, Inc., Mountain View, Calif.).

Exosomes can also be targeted for preferential uptake by particular cell types. A targeting strategy especially useful for the present invention is disclosed by Alvarez-Ervitti, et al. (2011). Using techniques disclosed therein, exosomes can be decorated with rabies viral glycoprotein (RVG) peptide. Exosomes bearing RVG home specifically to the brain, especially to neurons, oligodendrocytes, and microglia, with little nonspecific accumulation in other tissues.

The expression constructs of the present invention can also be delivered by means of nanoclews. Nanoclews are a cocoon-like DNA nanocomposites (Sun, et al., 2014). They can be loaded with nucleic acids for uptake by target cells and release in target cell cytoplasm. Methods for constructing nanoclews, loading them, and designing release molecules can be found in Sun, et al. (2014) and Sun, et al. (2015).

The gene editing constructs of the present invention can also be delivered not by induced expression by host cells, but by direct delivery, that is, delivery of a Cas nuclease protein, such as Cas9 protein, plus one of more gRNAs. Exosomes are a preferred vehicle for direct delivery, as they can be loaded with both proteins and RNAs (Alvarez-Ervitti, et al., 2011; Marcus and Leonard, 2013). An exemplary method of protein loading into exosomes is by the expression of a protein as a fusion with endosomal proteins such as lactadherin, in exosome producing cells. Another favorable feature of exosomes is their targetability to specific sites, such as the brain, as previously described. gRNAs can be loaded into the same exosomes as Cas nuclease protein, preferably, in the form of Cas/gRNA complexes. Cas endonucleases and gRNAs can alternatively be loaded into separate exosomes, for simultaneous or staged delivery.

Direct delivery of gene editing complexes can also be accomplished by menas of nanoclews. Sun, et al. (2015) disclose techniques for loading Cas9/gRNA complexes into nanoclews for uptake and release into receiving cells.

Direct delivery vehicles can be administered by any appropriate route, including, but not limited to, i.v., i.p, rectal, intrathecal, intracranial, inhalation, and per os, including in pill form.

The present invention is not limited to CRISPR systems that include Cas9 endonucleases or other Cas endonucleases. It also encompasses compositions and methods entailing the use of any CRISPR associated endonuclease that is capable of cleaving a viral genome after guidance to a PAM site by a gRNA. Examples include endonucleases of the family Cpf1 (CRISPR from Prevotella and Francisella 1) (Zetsche, et al., 2015). Two Cpf1 endonucleases have so far been shown to be effective at editing genes in a cultured human kidney cell system: *Acidaminococcus* sp. BV3L6 Cpf1, and *Lachnospiraceae bacterium* ND2006 Cpf1.

Cpf1 endonucleases expand the range of possible targets in JCV and other polyoma viruses, because they recognize a PAM different from the cytosine rich PAM recognized by Cas9. Cpf1 recognizes a thymine rich PAM, with a consensus sequence TTN, and that PAM is located at the 5' end of the target sequence. Cpf1 is guided by a smaller, simpler gRNA than that of Cas9 systems. Instead of a two-unit gRNA including crRNA and tracrRNA, or an engineered chimeric hybrid of crRNA and tracrRNA, Cpf1 is guided by single guide RNA, termed gRNA. The Cpf1 molecule is also smaller than the Cas9 molecule. This greater simplicity and smaller size facilitates both the design and use of CRISPR/Cpf1 systems, and the delivery of the endonuclease component to the nucleus of a host cell.

Hypothetical target sequences for Cpf1, based on 3' adjacency to 5'TTN sequences in the JCV T-Ag genome, are disclosed as a prophetic example, Example 2. A hypothetical method of eliminating the risk of JCV activation during an immunosuppressive therapy regime is also disclosed in Example 2. Therefore, the present invention encompasses a method for eliminating a risk of JCV activation in a subject during immunosuppressive therapy including the steps of: administering, to a subject infected with JCV, an effective amount of a gene editing composition including at least one isolated nucleic acid sequence encoding Cpf1 and at least one gRNA having a spacer sequence complementary to a target sequence in a JCV DNA; cleaving the target sequence in the JCV genome; disrupting the JCV genome; eliminating the JCV infection; eliminating the risk of JCV virus activation; and administering an immunosuppressive therapy to the subject.

The gRNAs of the present invention are synthesized generally as described by Zetsche, et al. Cloning of the gRNAs into vectors for expression in host cells is as described in Hu, et al., 2014, and in WO2015/031775 to Khalili, et al., both of which are incorporated in their entirety. Screening of Cpf1/gRNA combinations for gene editing activity is performed by genomic analyses, Surveyor assays, and assays of viral infection, activation, and expression, as disclosed in Hu, et al., 2014, and in WO2015/031775 to Khalili, et al. Detailed techniques for the use of Cpf1/gRNA combinations, included suggested vectors, are as described previously for Cas9/gRNA combinations.

The present invention is not limited to CRISPR systems including Cas9 or Cpf1 nucleases, C2c1, C2c3, TevCas9, Archaea Cas9, CasY.1-CasY.6, and CasX gRNAs, Argonaute endonuclease gDNAs, or the gRNAs previously disclosed. The present invention encompasses all methods for JCV elimination by any gRNA guided nuclease, both extant and to be discovered in the future, that can eradicate or disrupt the JCV replication cycle and subsequent destruction of nerve cells by PML.

ZFN and TALEN Compositions and Methods for Eliminating Risk of JCV Activation During Immunosuppressive Therapy.

The present invention includes compositions of engineered restriction enzymes of the ZFN (zinc finger nuclease) and TALEN (transcription activator-like effector nuclease) families. Unlike the CRISPR systems, these nucleases are not guided to target sites by gRNAs, but are engineered to recognize specific target sequences, to which they bind and then cleave. When cleavage is followed by nonhomologous end joining, random insertions or deletions occur at the cleavage site, usually causing a functional knock-out of the affected gene.

ZFNs are hybrid proteins, which combine a zinc finger DNA binding domain, with a DNA cleaving domain, derived from the nuclease domain of the restriction endonuclease FokI. To produce double stranded breaks, a pair of ZFNs are administered, each recognizing a different 12-18 base target sequence, with the target sequences being separated by 4-7 base pairs, to allow formation of an active FokI dimer. ZFNs are typically encoded into plasmids, viruses, or other vectors for expression in target cells (Urnov, et al., 2010). ZFNs specific for target sequences in the JCV genome can be designed by using publically available programs, such as ZiFiT (Sander, et al., 2010).

TALENs are proteins which contain DNA-binding domains composed of a series of 33-35-amino-acid repeat domains that each recognize a single base pair. Modular TALEN repeats can be linked together to recognize contiguous DNA sequences. TALEN repeats can be combined to recognize and cleave virtually any desired DNA sequence. (Miller, et al., 2011). TALENS specific for target sequences in the JCV genome can be designed by using publically available design programs, such as the TALE-NT 2.0 web interface, freely available online (Doyle, et al., 2012).

The present invention includes all ZFN and TALEN molecules, and their variants, extant or developed in the future, which are useful to cleave the JCV genome to disrupt the viral replication cycle and eradicate the virus.

Example 1: CRISPR/Cas9 Compositions and Methods for the Elimination of JCV, as a Co-Therapeutic Treatment with Natalizumab Natalizumab (Tysabri®) is a humanized monoclonal antibody against the cell adhesion molecule α4-integrin. In a co-therapeutic treatment regime, a subject found to harbor a latent JCV infection is treated with a CRISPR/Cas9 pharmaceutical composition until the infection is eliminated. The patient is then treated with natalizumab, as a remedy for multiple sclerosis or another autoimmune disease.

A subject can be screened for the presence of JCV infection by ELISA for anti-JCV antibodies in blood or serum. An exemplary ELISA is STRATIFY-JCV®, available from Biogen, Cambridge, Mass. Screening can alternatively be by quantitative PCR analysis for JCV DNA in a body fluid such as cerebrospinal fluid, blood, or urine. A suitable PCR test is available from Viracor-IBT Laboratories (Lee's Summit, Mo.).

If the subject is found to be infected with JCV, a course of co-therapeutic treatment is begun, with the administration of a pharmaceutical composition including at least one isolated nucleic acid sequence encoding a Clustered Regularly Interspaced Short Palindromic Repeat (CRISPR)-associated endonuclease, and at least one gRNA having a spacer sequence complementary to a target sequence in a JCV DNA. The preferred target sequences include any combination of m1, m2, and m3, as previously described.

The treatment continues until all evidence of JCV infection is eliminated, as determined by, for example, ELISA or quantitative PCR. At that point, natalizumab therapy is begun. A typical course of natalizumab includes a 300 mg intravenous infusion of a 2.6 mg/mL solution over one hour every four weeks (Tysabri® Prescribing Information). It is preferred that screening for JCV be repeated at suitable intervals over the course of natalizumab treatment, so that any reactivation of new or hidden virus reservoirs can be reacted to before symptoms of PML occur.

It is possible that a subject with active JCV infection and symptomatic PML could be considered for treatment with natalizumab. In this case, the screening test establishes a baseline of JCV presence. The method is otherwise performed as previously described, with natalizumab treatment commencing upon both resolution of the symptoms and elimination of residual JCV.

Example 2: CRISPR/Cpf1 Compositions and Methods for the Elimination of JCV, as a Co-Therapeutic Treatment with Natalizumab Hypothetical target sequences for Cpf1, based on 3' adjacency to 5'TTN sequences in the JCV T-Ag genome, are disclosed in TABLE 2, as target sequences cm1-cm236. Gene editing compositions of the present invention include at least one gRNA complementary to one of the listed target sequences. A gRNA of the present invention may or may not include a sequence complementary to the PAM sequence of a target sequence, which is listed in parentheses at the 5' end of each target sequence in TABLE 2. A gRNA may be complementary to a truncated variation of a listed sequence, for example one that is truncated by 1, 2, 3, or more nucleotides on the 3' end. A gRNA may be less than 100% complementary a target sequences listed in TABLE 2. For example, a gRNA can be 95% complimentary to a listed target sequence. The gRNA sequence can include additional 5' and/or 3' sequences that may not be complementary to a target sequence. The present invention includes gRNAs that are complementary to the antisense strand of each of the listed target sequences (not shown), or 95% complementary, or complementary to an antisense sequence that is truncated by 1, 2, 3, or more nucleotides. The gRNA sequences can be employed in a multiplex configuration, including combinations of two, three, four, five, six, seven, eight, nine, ten, or more different gRNAs.

It will be understood that Table 2 includes only a representative sample of target sequences in the JCV T-Ag genome. Additional sequences in other regions of the JCV genome are also within the scope of this invention, such as the regions encoding VP1, VP2, and VP3 and agnoprotein. Also within the scope of the invention are any existing additional sequences adjacent to different PAMs.

Prior to the start of natalizumab therapy, an effective dose of a composition including one or any combination of gRNAs complimentary to the sequences listed in TABLE 2, and Cpf1, are administered to a subject in need of elimination of latent JCV. Preferably, the gRNAs and Cpf1 are encoded in one or more expression vectors, in a suitable pharmaceutical composition, as described in prophetic Example 1. The protocol for natalizumab treatment is also as described in Example 1.

TABLE 2

Cpf1/gRNA TARGET SEQUENCES IN THE JCV GENOME.

| cm1: | (TTA) CTTAACAGTTGCAGTTATTTTGGG (SEQ ID NO: 14) |
|---|---|
| cm2: | (TTA) TTTTGGGGGAGGGGTCTTTGGTTT (SEQ ID NO: 15) |
| cm3: | (TTA) GCTTTCATAGTAGAAAATGTATAC (SEQ ID NO: 16) |
| cm4: | (TTA) TTTCTAAATCCAGCCTTTCTTTCC (SEQ ID NO: 17) |
| cm5: | (TTA) GTGATTTTCTCAGGTAGGCCTTTG (SEQ ID NO: 18) |
| cm6: | (TTA) CAATTCCAGGTGGAAACACCTGTG (SEQ ID NO: 19) |
| cm7: | (TTA) ACTTTTACACTTCCATCTAAGTAA (SEQ ID NO: 20) |
| cm8: | (TTA) CACTTCCATCTAAGTAATCTCTTA (SEQ ID NO: 21) |
| cm9: | (TTA) AGCAATCAAGGTTGCTTATGCCAT (SEQ ID NO: 22) |
| cm10: | (TTA) TGCCATGCCCTGAAGGTAAATCCC (SEQ ID NO: 23) |
| cm11: | (TTA) CATCCTCAAATACAACCATAAACT (SEQ ID NO: 24) |
| cm12: | (TTA) ATCTTTCTAATGGCATATTAACAT (SEQ ID NO: 25) |
| cm13: | (TTA) ACATTTAATGACTTTCCCCCACAG (SEQ ID NO: 26) |
| cm14: | (TTA) ATGACTTTCCCCCACAGAGATCAA (SEQ ID NO: 27) |
| cm15: | (TTA) ATACAATGCATTTTAGAAAGTCAT (SEQ ID NO: 28) |
| cm16: | (TTA) AGTCCATTTTATCAAGCAAGAAAT (SEQ ID NO: 29) |
| cm17: | (TTA) TCAAGCAAGAAATTAAACCTTTCA (SEQ ID NO: 30) |
| cm18: | (TTA) AAGTGATTTGGCTGATCCTTTTTT (SEQ ID NO: 31) |

TABLE 2-continued

Cpf1/gRNA TARGET SEQUENCES IN THE JCV GENOME.

| cm19: | (TTA) AAGTCATGCTCCTTAAGGCCCCCC (SEQ ID NO: 32) |
|---|---|
| cm20: | (TTA) TTCACACCTTTACAAATTAAAAAA (SEQ ID NO: 33) |
| cm21: | (TTA) CAAATTAAAAAACTAAAGGTACAT (SEQ ID NO: 34) |
| cm22: | (TTA) AAAAACTAAAGGTACATAGTTTTT (SEQ ID NO: 35) |
| cm23: | (TTA) TTAATTGCTGACACTCTATGTCTA (SEQ ID NO: 36) |
| cm24: | (TTA) ATTGCTGACACTCTATGTCTATGT (SEQ ID NO: 37) |
| cm25: | (TTA) AGAAAAACAAAATATTATGACCCC (SEQ ID NO: 38) |
| cm26: | (TTA) TAAAAGTTACAGAATATTTTCCA (SEQ ID NO: 39) |
| cm27: | (TTA) CAGAATATTTTTCCATAAGTTTCT (SEQ ID NO: 40) |
| cm28: | (TTA) GTGGTATACACAGCAAAAGAAGCA (SEQ ID NO: 41) |
| cm29: | (TTA) GGTGGGGTAGAGTGTTGGGATCCT (SEQ ID NO: 42) |
| cm30: | (TTA) AATGTATTCCACCAGGATTCCCAT (SEQ ID NO: 43) |
| cm31: | (TTA) AGTTTATTGTAAAAAACAAAATGC (SEQ ID NO: 44) |
| cm32: | (TTA) TTGTAAAAAACAAAATGCCCTGCA (SEQ ID NO: 45) |
| cm33: | (TTA) AAGCTTTAGATCCCTGTAGGGGGT (SEQ ID NO: 46) |
| cm34: | (TTA) AGTCACACCCAAACCATTGTCTGA (SEQ ID NO: 47) |
| cm35: | (TTA) AAAATTTTCTGTTTCTATGCCTTA (SEQ ID NO: 48) |
| cm36: | (TTA) GCATGCACATTAAACAGGGGCAAT (SEQ ID NO: 49) |
| cm37: | (TTA) AACAGGGGCAATGCACTGAAGGAT (SEQ ID NO: 50) |
| cm38: | (TTA) GTGGCACAGTTAGGCCATTCCTTG (SEQ ID NO: 51) |
| cm39: | (TTA) GGCCATTCCTTGCAATAAGGGTA (SEQ ID NO: 52) |
| cm40: | (TTA) GGAGGAAAATCACAACCAACCTCT (SEQ ID NO: 53) |
| cm41: | (TTA) CACCTTGTTCCATTTTTTTATATA (SEQ ID NO: 54) |
| cm42: | (TTA) TATAAAAAATTCATTCTCTTCATC (SEQ ID NO: 55) |
| cm43: | (TTA) GCTTTTTGCAGCAAAAAATTACTG (SEQ ID NO: 56) |
| cm44: | (TTA) CTGCAAAAAAGGGAAAAACAAGGG (SEQ ID NO: 57) |

TABLE 2-continued

Cpf1/gRNA TARGET SEQUENCES IN THE JCV GENOME.

| | | |
|---|---|---|
| cm45: | (TTA)CTACTTCTGAGTAAGCTTGGAGGC | (SEQ ID NO: 58) |
| cm46: | (TTT)ACTTAACAGTTGCAGTTATTTTGG | (SEQ ID NO: 59) |
| cm47: | (TTT)TGGGGGAGGGGTCTTTGGTTTTTT | (SEQ ID NO: 60) |
| cm48: | (TTT)GGTTTTTTGAAACATTGAAAGCCT | (SEQ ID NO: 61) |
| cm49: | (TTT)TTTGAAACATTGAAAGCCTTTACA | (SEQ ID NO: 62) |
| cm50: | (TTT)CCTGTGTGTCTGCACCAGAGGCTT | (SEQ ID NO: 63) |
| cm51: | (TTT)CATAGTAGAAAATGTATACATGCT | (SEQ ID NO: 64) |
| cm52: | (TTT)CTAAATCCAGCCTTTCTTTCCACT | (SEQ ID NO: 65) |
| cm53: | (TTT)CTTTCCACTGCACAATCCTCTCAT | (SEQ ID NO: 66) |
| cm54: | (TTT)CCACTGCACAATCCTCTCATGAAT | (SEQ ID NO: 67) |
| cm55: | (TTT)GCAAAATCCTTTTTTCTAGCAAAT | (SEQ ID NO: 68) |
| cm56: | (TTT)TTTCTAGCAAATACTCAGAGCAGC | (SEQ ID NO: 69) |
| cm57: | (TTT)CTAGCAAATACTCAGAGCAGCTTA | (SEQ ID NO: 70) |
| cm58: | (TTT)TCTCAGGTAGGCCTTTGGTCTAAA | (SEQ ID NO: 71) |
| cm59: | (TTT)GGTCTAAAATCTATCTGCCTTACA | (SEQ ID NO: 72) |
| cm60: | (TTT)TGTTTTGGTGTTTTCTCTCTAAAT | (SEQ ID NO: 73) |
| cm61: | (TTT)TCTCTCTAAATTAACTTTTACACT | (SEQ ID NO: 74) |
| cm62: | (TTT)TACATCCTCAAATACAACCATAAA | (SEQ ID NO: 75) |
| cm63: | (TTT)AATCTTTCTAATGGCATATTAACA | (SEQ ID NO: 76) |
| cm64: | (TTT)CTAATGGCATATTAACATTTAATG | (SEQ ID NO: 77) |
| cm65: | (TTT)AATGACTTTCCCCCACAGAGATCA | (SEQ ID NO: 78) |
| cm66: | (TTT)GCCACTGTCTATTGGCCCCTTGAA | (SEQ ID NO: 79) |
| cm67: | (TTT)TTTGGAATGTTTAATACAATGCAT | (SEQ ID NO: 80) |
| cm68: | (TTT)TTGGAATGTTTAATACAATGCATT | (SEQ ID NO: 81) |
| cm69: | (TTT)TGGAATGTTTAATACAATGCATTT | (SEQ ID NO: 82) |
| cm70: | (TTT)AATACAATGCATTTTAGAAAGTCA | (SEQ ID NO: 83) |
| cm71: | (TTT)TAGAAAGTCATAAATAACAGTGTC | (SEQ ID NO: 84) |
| cm72: | (TTT)GAGGCAGCAAGCAATGAATCCAGG | (SEQ ID NO: 85) |
| cm73: | (TTT)TATCAAGCAAGAAATTAAACCTTT | (SEQ ID NO: 86) |
| cm74: | (TTT)ATCAAGCAAGAAATTAAACCTTTC | (SEQ ID NO: 87) |
| cm75: | (TTT)CAACTAACATTTCTTCTCTGGTCA | (SEQ ID NO: 88) |
| cm76: | (TTT)GTTTGGCTGCTACAGTATCAACAG | (SEQ ID NO: 89) |
| cm77: | (TTT)GGCTGCTACAGTATCAACAGCCTG | (SEQ ID NO: 90) |
| cm78: | (TTT)TTTGATTTTTGCTATCTGCAAAAA | (SEQ ID NO: 91) |
| cm79: | (TTT)TTGATTTTTGCTATCTGCAAAAAT | (SEQ ID NO: 92) |
| cm80: | (TTT)TGATTTTTGCTATCTGCAAAAATT | (SEQ ID NO: 93) |
| cm81: | (TTT)GATTTTTGCTATCTGCAAAAATTT | (SEQ ID NO: 94) |
| cm82: | (TTT)TTGCTATCTGCAAAAATTTGGGCA | (SEQ ID NO: 95) |
| cm83: | (TTT)GCTATCTGCAAAAATTTGGGCATT | (SEQ ID NO: 96) |
| cm84: | (TTT)GGGCATTATAATAGTGTTTTTCAT | (SEQ ID NO: 97) |
| cm85: | (TTT)TCATGATGGTTAAAGTGATTTGGC | (SEQ ID NO: 98) |
| cm86: | (TTT)GGCTGATCCTTTTTTTCACATTTT | (SEQ ID NO: 99) |
| cm87: | (TTT)TTTTCACATTTTTTGCATTGCTGT | (SEQ ID NO: 100) |
| cm88: | (TTT)TTTCACATTTTTTGCATTGCTGTG | (SEQ ID NO: 101) |
| cm89: | (TTT)TTCACATTTTTTGCATTGCTGTGG | (SEQ ID NO: 102) |
| cm90: | (TTT)TTCACATTTTTTGCATTGCTGTGG | (SEQ ID NO: 103) |
| cm91: | (TTT)TCACATTTTTTGCATTGCTGTGGG | (SEQ ID NO: 104) |
| cm92: | (TTT)CACATTTTTTGCATTGCTGTGGGT | (SEQ ID NO: 105) |
| cm93: | (TTT)TTTGCATTGCTGTGGGTTTTCCTG | (SEQ ID NO: 106) |
| cm95: | (TTT)TGCATTGCTGTGGGTTTTCCTGAA | (SEQ ID NO: 108) |
| cm96: | (TTT)GCATTGCTGTGGGTTTTCCTGAAA | (SEQ ID NO: 109) |
| cm97: | (TTT)CCATGAAACCTGCTTAGTTTCTTC | (SEQ ID NO: 110) |

TABLE 2-continued

Cpf1/gRNA TARGET SEQUENCES IN THE JCV GENOME.

| | | |
|---|---|---|
| cm98: | (TTT) CTTCTGGTTCTTCTGGGTTAAAGT | (SEQ ID NO: 111) |
| cm99: | (TTT) CTTCCACTACTGCATATGGCTGTC | (SEQ ID NO: 112) |
| cm100: | (TTT) ACAAATTAAAAAACTAAAGGTACA | (SEQ ID NO: 113) |
| cm101: | (TTT) TTGACAGTAGTTATTAATTGCTGA | (SEQ ID NO: 114) |
| cm102: | (TTT) TGACAGTAGTTATTAATTGCTGAC | (SEQ ID NO: 115) |
| cm103: | (TTT) GACAGTAGTTATTAATTGCTGACA | (SEQ ID NO: 116) |
| cm104: | (TTT) TTCCATAAGTTTCTTATATAAAAT | (SEQ ID NO: 117) |
| cm105: | (TTT) TCCATAAGTTTCTTATATAAAATT | (SEQ ID NO: 118) |
| cm106: | (TTT) CCATAAGTTTCTTATATAAAATTT | (SEQ ID NO: 119) |
| cm107: | (TTT) CTTATATAAAATTTGAGCTTTTTC | (SEQ ID NO: 120) |
| cm108: | (TTT) TTCTTTAGTGGTATACACAGCAAA | (SEQ ID NO: 121) |
| cm109: | (TTT) TCTTTAGTGGTATACACAGCAAAA | (SEQ ID NO: 122) |
| cm110: | (TTT) CTTTAGTGGTATACACAGCAAAAG | (SEQ ID NO: 123) |
| cm111: | (TTT) AGTGGTATACACAGCAAAAGAAGC | (SEQ ID NO: 124) |
| cm112: | (TTT) AGGGTCTTCTACCTTTTTTTCTT | (SEQ ID NO: 125) |
| cm113: | (TTT) TTTTTCTTTTAGGTGGGGTAGAG | (SEQ ID NO: 126) |
| cm114: | (TTT) TTTTCTTTTAGGTGGGGTAGAGT | (SEQ ID NO: 127) |
| cm115: | (TTT) TTTCTTTTAGGTGGGGTAGAGTG | (SEQ ID NO: 128) |
| cm116: | (TTT) TTCTTTTAGGTGGGGTAGAGTGT | (SEQ ID NO: 129) |
| cm117: | (TTT) TCTTTTAGGTGGGGTAGAGTGTT | (SEQ ID NO: 130) |
| cm118: | (TTT) CTTTTAGGTGGGGTAGAGTGTTG | (SEQ ID NO: 131) |
| cm119: | (TTT) TCATCATCACTGGCAAACATTTCT | (SEQ ID NO: 132) |
| cm120: | (TTT) CATCATCACTGGCAAACATTTCTT | (SEQ ID NO: 133) |
| cm121: | (TTT) ATTGTAAAAAACAAAATGCCCTGC | (SEQ ID NO: 134) |
| cm122: | (TTT) AGATCCCTGTAGGGGGTGTCTCCA | (SEQ ID NO: 135) |
| cm123: | (TTT) CTCCCAGCAATGAAGAGCTTCTTG | (SEQ ID NO: 136) |
| cm124: | (TTT) TCTGTTTCTATGCCTTAATTTTAG | (SEQ ID NO: 137) |
| cm125: | (TTT) TAGCATGCACATTAAACAGGGGCA | (SEQ ID NO: 138) |
| cm126: | (TTT) TACACCTTGTTCCATTTTTTTATA | (SEQ ID NO: 139) |
| cm127: | (TTT) ACACCTTGTTCCATTTTTTTATAT | (SEQ ID NO: 140) |
| cm128: | (TTT) TTTATATAAAAAATTCATTCTCTT | (SEQ ID NO: 141) |
| cm129: | (TTT) GCATTTTTTCAGATAAGCTTTTCT | (SEQ ID NO: 142) |
| cm130: | (TTT) TTTCAGATAAGCTTTTCTCATGAC | (SEQ ID NO: 143) |
| cm131: | (TTT) TTCAGATAAGCTTTTCTCATGACA | (SEQ ID NO: 144) |
| cm132: | (TTT) TCAGATAAGCTTTTCTCATGACAG | (SEQ ID NO: 145) |
| cm133: | (TTT) CAGATAAGCTTTTCTCATGACAGG | (SEQ ID NO: 146) |
| cm134: | (TTT) TCTCATGACAGGAATGTTCCCCCA | (SEQ ID NO: 147) |
| cm135: | (TTT) GTCCATTTTAGCTTTTTGCAGCAA | (SEQ ID NO: 148) |
| cm136: | (TTT) TAGCTTTTTGCAGCAAAAAATTAC | (SEQ ID NO: 149) |
| cm137: | (TTT) AGCTTTTTGCAGCAAAAAATTACT | (SEQ ID NO: 150) |
| cm138: | (TTT) TGCAGCAAAAAATTACTGCAAAAA | (SEQ ID NO: 151) |
| cm139: | (TTT) GCAGCAAAAAATTACTGCAAAAAA | (SEQ ID NO: 152) |
| cm140: | (TTT) CCCTGGCCTCCTAAAAAGCCTCCA | (SEQ ID NO: 153) |
| cm141: | (TTC) CTGTGTGTCTGCACCAGAGGCTTC | (SEQ ID NO: 154) |
| cm142: | (TTC) TGAGACCTGGGAAAAGCATTGTGA | (SEQ ID NO: 155) |
| cm143: | (TTC) TGCTTCAGAATCTTCCTCTCTAGG | (SEQ ID NO: 156) |
| cm144: | (TTC) AGAATCTTCCTCTCTAGGAAAGTC | (SEQ ID NO: 157) |
| cm145: | (TTC) CTCTCTAGGAAAGTCAAGAATGGG | (SEQ ID NO: 158) |
| cm146: | (TTC) TTTCCACTGCACAATCCTCTCATG | (SEQ ID NO: 159) |
| cm147: | (TTC) TAGCAAATACTCAGAGCAGCTTAG | (SEQ ID NO: 160) |
| cm148: | (TTC) TCAGGTAGGCCTTTGGTCTAAAAT | (SEQ ID NO: 161) |
| cm149: | (TTC) TAGGCACTGAATATTCATTCATGG | (SEQ ID NO: 162) |

TABLE 2-continued

Cpf1/gRNA TARGET SEQUENCES IN THE JCV GENOME.

| | | |
|---|---|---|
| cm150: | (TTC) ATTCATGGTTACAATTCCAGGTGG | (SEQ ID NO: 163) |
| cm151: | (TTC) ATGGTTACAATTCCAGGTGGAAAC | (SEQ ID NO: 164) |
| cm152: | (TTC) CAGGTGGAAACACCTGTGTTCTTT | (SEQ ID NO: 165) |
| cm153: | (TTC) TTTTGTTTTGGTGTTTTCTCTCTA | (SEQ ID NO: 166) |
| cm154: | (TTC) TCTCTAAATTAACTTTTACACTTC | (SEQ ID NO: 167) |
| cm155: | (TTC) CATCTAAGTAATCTCTTAAGCAAT | (SEQ ID NO: 168) |
| cm156: | (TTC) AAAGTTTAATCTTTCTAATGGCAT | (SEQ ID NO: 169) |
| cm157: | (TTC) AAAGTTTAATCTTTCTAATGGCAT | (SEQ ID NO: 170) |
| cm158: | (TTC) TAATGGCATATTAACATTTAATGA | (SEQ ID NO: 171) |
| cm159: | (TTC) CCCCACAGAGATCAAGTAAAGCTG | (SEQ ID NO: 172) |
| cm160: | (TTC) AACTAACATTTCTTCTCTGGTCAT | (SEQ ID NO: 173) |
| cm161: | (TTC) TCTGGTCATGTGGATGCTGTCAAC | (SEQ ID NO: 174) |
| cm162: | (TTC) ATGATGGTTAAAGTGATTTGGCTG | (SEQ ID NO: 175) |
| cm163: | (TTC) CTGAAAGTCTAAGTACATGCCCAT | (SEQ ID NO: 176) |
| cm164: | (TTC) CATGAAACCTGCTTAGTTTCTTCT | (SEQ ID NO: 177) |
| cm165: | (TTC) TTCTGGTTCTTCTGGGTTAAAGTC | (SEQ ID NO: 178) |
| cm166: | (TTC) TGGTTCTTCTGGGTTAAAGTCATG | (SEQ ID NO: 179) |
| cm167: | (TTC) TTCTGGGTTAAAGTCATGCTCCTT | (SEQ ID NO: 180) |
| cm168: | (TTC) TGGGTTAAAGTCATGCTCCTTAA | (SEQ ID NO: 181) |
| cm169: | (TTC) CACTACTGCATATGGCTGTCTACA | (SEQ ID NO: 182) |
| cm170: | (TTC) ACACCTTTACAAATTAAAAAACTA | (SEQ ID NO: 183) |
| cm171: | (TTC) CATAAGTTTCTTATATAAAATTTG | (SEQ ID NO: 184) |
| cm172: | (TTC) TTATATAAAATTTGAGCTTTTTCT | (SEQ ID NO: 185) |
| cm173: | (TTC) TATTACTAAACACAGCTTGACTGA | (SEQ ID NO: 186) |
| cm174: | (TTC) TACCTTTTTTTCTTTTTAGGTGG | (SEQ ID NO: 187) |
| cm175: | (TTC) TTTTTAGGTGGGGTAGAGTGTTGG | (SEQ ID NO: 188) |
| cm176: | (TTC) TTTTTAGGTGGGGTAGAGTGTTGG | (SEQ ID NO: 189) |
| cm177: | (TTC) ATCATCACTGGCAAACATTTCTTC | (SEQ ID NO: 190) |
| cm178: | (TTC) ATCCCACTTCTCATTAAATGTATT | (SEQ ID NO: 191) |
| cm179: | (TTC) CACCAGGATTCCCATTCATCTGTT | (SEQ ID NO: 192) |
| cm180: | (TTC) CATTCATCTGTTCCATAGGTTGG | (SEQ ID NO: 193) |
| cm181: | (TTC) ATCTGTTCCATAGGTTGGCACCTA | (SEQ ID NO: 194) |
| cm182: | (TTC) CATAGGTTGGCACCTAAAAAAAAA | (SEQ ID NO: 195) |
| cm183: | (TTC) TCCCAGCAATGAAGAGCTTCTTGG | (SEQ ID NO: 196) |
| cm184: | (TTC) TTGGGTTAAGTCACACCCAAACCA | (SEQ ID NO: 197) |
| cm185: | (TTC) TTAAAAATTTTCTGTTTCTATGCC | (SEQ ID NO: 198) |
| cm186: | (TTC) TGTTTCTATGCCTTAATTTTAGCA | (SEQ ID NO: 199) |
| cm187: | (TTC) CTTGCAATAAAGGGTATCAGAATT | (SEQ ID NO: 200) |
| cm188: | (TTC) CATGTACCAAAATCAGGCTGATGA | (SEQ ID NO: 201) |
| cm189: | (TTC) CATTTTTTTATATAAAAAATTCAT | (SEQ ID NO: 202) |
| cm190: | (TTC) ATTCTCTTCATCTTGTCTTCGTCC | (SEQ ID NO: 203) |
| cm191: | (TTC) TCTTCATCTTGTCTTCGTCCCCAC | (SEQ ID NO: 204) |
| cm192: | (TTC) ATCTTGTCTTCGTCCCCACCTTTA | (SEQ ID NO: 205) |
| cm193: | (TTC) GTCCCCACCTTTATCAGGGTGGAG | (SEQ ID NO: 206) |
| cm194: | (TTC) TTTGCATTTTTTCAGATAAGCTTT | (SEQ ID NO: 207) |
| cm195: | (TTC) AGATAAGCTTTTCTCATGACAGGA | (SEQ ID NO: 208) |
| cm196: | (TTC) TCATGACAGGAATGTTCCCCCATG | (SEQ ID NO: 209) |
| cm197: | (TTC) CCCCATGCAGACCTATCAAGGCCT | (SEQ ID NO: 210) |
| cm198: | (TTC) CTCCCTATTCAGCACTTTGTCCAT | (SEQ ID NO: 211) |
| cm199: | (TTC) AGCACTTTGTCCATTTTAGCTTTT | (SEQ ID NO: 212) |
| cm200: | (TTC) CCTGGCCTCCTAAAAAGCCTCCAC | (SEQ ID NO: 213) |
| cm201: | (TTC) TGAGTAAGCTTGGAGGCGGAGGCG | (SEQ ID NO: 214) |

TABLE 2-continued

Cpf1/gRNA TARGET SEQUENCES IN THE JCV GENOME.

| | | |
|---|---|---|
| cm202: | (TTG) CAGTTATTTTGGGGGAGGGGTCTT | (SEQ ID NO: 215) |
| cm203: | (TTG) GGGGAGGGGTCTTTGGTTTTTGA | (SEQ ID NO: 216) |
| cm204: | (TTG) GTTTTTTGAAACATTGAAAGCCTT | (SEQ ID NO: 217) |
| cm205: | (TTG) AAACATTGAAAGCCTTTACAGATG | (SEQ ID NO: 218) |
| cm206: | (TTG) AAAGCCTTTACAGATGTGAAAAGT | (SEQ ID NO: 219) |
| cm207: | (TTG) TGATTGTGATTCAGTGCTTGATCC | (SEQ ID NO: 220) |
| cm208: | (TTG) TGATTCAGTGCTTGATCCATGTCC | (SEQ ID NO: 221) |
| cm209: | (TTG) ATCCATGTCCAGAGTCTTCTGCTT | (SEQ ID NO: 222) |
| cm210: | (TTG) CAAAATCCTTTTTTCTAGCAAATA | (SEQ ID NO: 223) |
| cm211: | (TTG) GTGTTTTCTCTCTAAATTAACTTT | (SEQ ID NO: 224) |
| cm212: | (TTG) CCACTGTCTATTGGCCCCTTGAAT | (SEQ ID NO: 225) |
| cm213: | (TTG) GCCCCTTGAATAGCCAGTACCTTT | (SEQ ID NO: 226) |
| cm214: | (TTG) AATAGCCAGTACCTTTTTTTGGA | (SEQ ID NO: 227) |
| cm215: | (TTG) GAATGTTTAATACAATGCATTTTA | (SEQ ID NO: 228) |
| cm216: | (TTG) AGGCAGCAAGCAATGAATCCAGGC | (SEQ ID NO: 229) |
| cm217: | (TTG) CCATGTGCCCCAAAAATTAAGTCC | (SEQ ID NO: 230) |
| cm218: | (TTG) TTTGGCTGCTACAGTATCAACAGC | (SEQ ID NO: 231) |
| cm219: | (TTG) GCTGCTACAGTATCAACAGCCTGC | (SEQ ID NO: 232) |
| cm220: | (TTG) ATTTTGCTATCTGCAAAAATTTG | (SEQ ID NO: 233) |
| cm221: | (TTG) CTATCTGCAAAAATTTGGGCATTA | (SEQ ID NO: 234) |
| cm222: | (TTG) GGCATTATAATAGTGTTTTTCATG | (SEQ ID NO: 235) |
| cm223: | (TTG) GCTGATCCTTTTTTTCACATTTTT | (SEQ ID NO: 236) |
| cm224: | (TTG) CTGTGGGTTTTCCTGAAAGTCTAA | (SEQ ID NO: 237) |
| cm225: | (TTG) GTTTCCAAGGCATACTGTGTAACT | (SEQ ID NO: 238) |
| cm226: | (TTG) ACAGTAGTTATTAATTGCTGACAC | (SEQ ID NO: 239) |
| cm227: | (TTG) CTGACACTCTATGTCTATGTGGTG | (SEQ ID NO: 240) |
| cm228: | (TTG) ACTGAGGAATGCATGCAGATCTAC | (SEQ ID NO: 241) |
| cm229: | (TTG) GGATCCTGTGTTTTCATCATCACT | (SEQ ID NO: 242) |
| cm230: | (TTG) GGTTAAGTCACACCCAAACCATTG | (SEQ ID NO: 243) |
| cm231: | (TTG) TCTGAAGCAATCAAAGCAATAGCA | (SEQ ID NO: 244) |
| cm232: | (TTG) CAATAAAGGGTATCAGAATTAGGA | (SEQ ID NO: 245) |
| cm233: | (TTG) TTCCATTTTTTATATAAAAAATT | (SEQ ID NO: 246) |
| cm234: | (TTG) TCTTCGTCCCCACCTTTATCAGGG | (SEQ ID NO: 247) |
| cm235: | (TTG) CATTTTTTCAGATAAGCTTTTCTC | (SEQ ID NO: 248) |
| cm236: | (TTG) CAGCAAAAAATTACTGCAAAAAAG | (SEQ ID NO: 249) |

The invention has been described in an illustrative manner, and it is to be understood that the terminology that has been used is intended to be in the nature of words of description rather than of limitation. Obviously, many modifications and variations of the present invention are possible in light of the above teachings. It is, therefore, to be understood that within the scope of the appended claims, the invention can be practiced otherwise than as specifically described.

REFERENCES

Alvarez-Erviti L, Seow Y, Yin H, Betts C, Lakhal S, M J A Wood. Delivery of siRNA to the mouse brain by systemic injection of targeted exosomes. Nature Biotechnol. 2011, 29: 341-345.

Andrei G, Snoeck R, Vandeputte M, De Clercq E. Activities of various compounds against murine and primate polyomaviruses. Antimicrob Agents Chemother. 1997; 41: 587-593.

Bag A K, Cure J K, Chapman P R, Roberson G H, Shah R. JC virus infection of the brain. ANJR 2010, 31: 1564-1576.

Bayliss J, Karasoulos T CAMcLean. Immunosuppression Increases JC polyomavirus large T antigen DNA load in the brains of patients without progressive multifocal leukoencephalopathy. J. Infections Diseases, 2012, DOI: 10.1093/infdis/jis668.

Berger J R. The clinical features of PML. Cleve Clin J Med. 2011; 78 Suppl2: S8-12.

Bhaya D, Davison M, Barrangou R. CRISPR-Cas systems in bacteria and archaea: versatile small RNAs for adaptive defense and regulation. Annu Rev Genet. 2011; 45: 273-297.

Chalkley J J, Berger J R. Progressive multifocal leukoencephalopathy in multiple sclerosis. Curr Neurol Neurosci Rep. 2013; 13: 408.

Chapagain M L, Sumibcay L, Gurjav U, Kaufusi P H, Kast R E, Nerurkar V R. Serotonin receptor 2A blocker (risperidone) has no effect on human polyomavirus JC infection of primary human fetal glial cells. J Neurovirol. 2008; 14: 448-454.

Clifford D B, Ances B, Costello C, Rosen-Schmidt S, Andersson M, Parks D, et al. Rituximab-associated progressive multifocal leukoencephalopathy in rheumatoid arthritis. Arch Neurol. 2011; 68: 1156-1164.

DeCaprio J A, Imperiale M J, Major E O. Polyomaviruses. In: Fields Virology, 6th edition. Knipe D M and Howley P M (Eds). Philadelphia: Lippincott, Williams & Wilkins; 2013. pp. 1633-1661.

Ding Q, Strong A, Patel K A, Ng S L, Gosis B S, Regan S N, Cowan C A, Rader D J, Musunuru K. Permanent alteration of PCSK9 with in vivo CRISPR-Cas9 genome editing. Circ. Res. 2014, 115:488-492.

Doyle E L, Booher N., Standage D S, Voytas D F, Brendel V P, VanDyk, JK, Bogdanove A J. (2012) TAL Effector-Nucleotide Targeter (TALE-NT) 2.0: tools for TAL effector design and target prediction. Nucleic Acids Res. doi: 10.1093/nar/gks608.

Elphick G F, Querbes W, Jordan J A, Gee G V, Eash S, Manley K, et al. The human polyomavirus, JCV, uses serotonin receptors to infect cells. Science 2004; 306: 1380-1383.

Frisque R J, Bream G L, Cannella M T. Human polyomavirus JC virus genome. J Virol. 1984; 51: 458-469.

Gaj T, Gersbach C A, Barbas C F 3rd. ZFN, TALEN, and CRISPR/Cas-based methods for genome engineering. Trends Biotechnol. 2013; 31: 397-405.

Hou J, Major E O. The efficacy of nucleoside analogs against JC virus multiplication in a persistently infected human fetal brain cell line. J. Neurovirol. 1998; 4: 451-456.

Hsu P D, Lander E S, Zhang F. Development and applications of CRISPR-Cas9 for genome engineering. Cell 2014, 157: 1262-1278.

Hu W, Kaminski R, Yang F, Zhang Y, Cosentino L, Li F, et al. RNA-directed gene editing specifically eradicates latent and prevents new HIV-1 infection. Proc Natl Acad Sci USA 2014; 111: 11461-11466.

Khalili K, White M K, Sawa H, Nagashima K, Safak M. The agnoprotein of polyomaviruses: a multifunctional auxiliary protein. J Cell Physiol. 2005; 204: 1-7.

Kooijmans S A A, Vader P, Dommelen S M, van Solinge W W, Raymond M Schiffelers R M. Exosome mimetics: a novel class of drug delivery systems. Int. J. Nanomed. 2012, 7: 1525-1541.

Lander E S, Zhang F. Development and applications of CRISPR-Cas9 for genome engineering. Cell 2014, 157: 1262-1278.

Lee H K, Finniss S, Cazacu S, Bucris E, Ziv-Av A, Xiang C, Bobbitt K, Rempel S A, Hasselbach L, Mikkelsen T, Slavin S, Brodie C. Mesenchymal stem cells deliver synthetic microRNA mimics to glioma cells and glioma stem cells and inhibit their cell migration and self-renewal. Oncotarget. 2013, 4:346-61.

Lee Y, Andaloussi S E, Wood M J A. Exosomes and microvesicles: extracellular vesicles for genetic information transfer and gene therapy. Human Molecular Genetics 212, doi:10,1093/hmg/dds317.

Mali P, Esvelt K M, Church G M. Cas9 as a versatile tool for engineering biology. Nat Methods 2013; 10:957-963.

Marcus M E, and Leonard J N. FedExosomes: Engineering therapeutic biological nanoparticles that truly deliver. Pharmaceuticals 2103, 6: 659-680.

Miller J C, Tan S, Qiao G, Barlow K, Wang J, Xia D F, Meng X, Paschon D E, Leung E, Hinkley S J, Dulay G P, Hua K L, Ankoudinova I, Cost G J, Urnov F D, Zhang H S, Holmes M C, Zhang L, Gregory P D, Rebar E J. A TALE nuclease architecture for efficient genome editing. Nature Biotechnology 2011:29: 143-150.

Nagayama S, Gondo Y, Araya S, Minato N, Fujita-Nakata M, Kaito M, et al. Progressive multifocal leukoencephalopathy developed 26 years after renal transplantation. Clin Neurol Neurosurg. 2013; 115: 1482-1484.

San Sebastian W, Samaranch L, Kells A P, Forsayeth, Bankiewicz K S. Gene therapy for misfolding protein diseases of the central nervous system. Neurotherapeutics (2013) 10:498-510.

Sander J D, Maeder M., Reyon D, Voytas D F, Joung J K, Dobbs D. (2010) ZiFiT (Zinc Finger Targeter): an updated zinc finger engineering tool. Nucleic Acids Research, 38:W462-468.

Saribas A S, Ozdemir A, Lam C, Safak M. JC virus-induced progressive multifocal leukoencephalopathy. Future Virol 2010, 7: 313-323.

Schwab N, Ulzheimer J C, Fox R J, Schneider-Hohendorf T, Kieseier B C, Monoranu C M, et al. Fatal progressive multifocal leukoencephalopathy associated with efalizumab therapy: insights into the role of leukointegrin aLb2 in JC virus control. Neurology 2012; 78: 458-467.

Shtam T A, Kovalev R A, Varfolomeeva E Y, Makarov E M, Kil Y V, Filatov M V. Exosomes are natural carriers of exogenous siRNA to human cells in vitro. Cell Communication and Signaling 2013, 11:88 (www.biosignaling.com/content/11/1/88).

Slaymaker I M, Gao L, Zetsche B, Scott D A, Yan W X, Feng Zhang F. Rationally engineered Cas9 nucleases with improved specificity. Published online 1 Dec. 2015 [DOI: 10.1126/science.aad5227]

Sun W, Jiang T, Yue Lu Y, Reiff M, Mo R, Zhen Gu Z. Cocoon-like self-degradable DNA nanoclew for anticancer drug delivery. J. Am. Chem. Soc. 2014, 136:14722-14725.

Sun W, Ji W, Hall J M, Hu Q, Wang C, Beisel C L, Gu Z. Self-assembled DNA nanoclews for the efficient delivery of CRISPR-Cas9 for genome editing. Angew. Chem. Int. Ed. 2015: 12029-12033.

Tavazzi E, White M K, Khalili K. Progressive multifocal leukoencephalopathy: clinical and molecular aspects. Rev Med Virol. 2012; 22:2.

Urnov F D, Rebar E J, Holmes M C, Zhang H S, Gregory P D: Genome editing with engineered zinc finger nucleases. Nat Rev Genet 2010, 11(9):636-646.

Waggoner J, Martinu T, M D, Palmer, S M. Progressive multifocal leukoencephalopathy following heightened immunosuppression after lung transplant: A case report. J. Heart Lung Transplant 2009, 28: 395-398.

White M K, Khalili K. Polyomaviruses and human cancer: molecular mechanisms underlying patterns of tumorigenesis. Virology 2004; 324: 1-16.

White M K, Khalili K. Pathogenesis of progressive multifocal leukoencephalopathy—revisited. J Infect Dis. 2011; 203: 578-586.

Wollebo H S, Bellizzi A, Kaminski R, Hu W, White M K, Khalili K. CRISPR/Cas9 system as an agent for eliminating polyomavirus JC infection. PLoS ONE 2015, 10(9): e0136046. doi:10.1371/journal.pone.0136046.

Zetsche B, Gootenberg J S., Abudayyeh O O, Slaymaker I M, Makarova K S, Essletzbichler P, Volz S E, Joung J, van der Oost J, Regev A, Koonin E V, Zhang F, Cpf1 Is a Single RNA-Guided Endonuclease of a Class 2 CRISPR-Cas System. Cell 163, 1-13 Oct. 22, 2015.

What is claimed is:

1. A method of eliminating a risk of John Cunningham virus (JCV) activation in a subject undergoing immunosuppressive therapy, including the steps of:
administering, to a subject latently infected with JCV, an effective amount of a gene editing composition of a Clustered Regularly Interspaced Short Palindromic Repeat (CRISPR) Cas9 endonuclease directed toward at least one target PAM sequence in the T-antigen of the JCV genome chosen from the group consisting of TTA, TTC, TTG, and TTT;
cleaving the target sequence in the JCV genome;
disrupting the JCV genome;
eliminating the JCV infection;
eliminating the risk of JCV activation; and
treating the subject with an immunosuppressive therapy at a time chosen from the group consisting of before, during, or after administering the gene editing composition.

2. The method according to claim 1, additionally including, prior to said administering step, the steps of screening the subject for latent JCV infection, and verifying the presence of a latent JCV infection.

3. The method according to claim 1, wherein the gene editing composition is defined as an effective amount of a pharmaceutical composition including at least one isolated nucleic acid sequence encoding the CRISPR Cas9 endonuclease, and at least one guide RNA (gRNA) having a spacer sequence complementary to a target PAM sequence in the T-antigen of a JCV DNA chosen from the group consisting of TTA, TTC, TTG, and TTT.

4. The method according to claim 3, wherein the CRISPR Cas9 endonuclease is selected from a wild-type Cas9, a human-optimized Cas9, a nickase mutant Cas9, SpCas9 (K855a), SpCas9(K810A/K1003A/r1060A), or SpCas9 (K848A/K1003A/R1060A).

5. The method according to claim 4, wherein the at least one gRNA having a spacer sequence complementary to a target sequence in a JCV DNA is further defined as at least one gRNA having a spacer sequence complimentary to a target sequence in the large T-antigen (T-Ag) encoding region of the JCV DNA.

6. The method according to claim 5, wherein the at least one gRNA having a spacer sequence complimentary to a target sequence in the T-Ag encoding region of the JCV DNA includes a gRNA having a spacer sequence complementary to a target sequence in the TM1 region of the T-Ag encoding region chosen from the group consisting of SEQ ID NO: 1, SEQ ID NO: 2, SEQ ID NO: 3, and SEQ ID NO: 4, a gRNA having a spacer sequence complimentary to a target sequence in the TM2 region of the T-Ag encoding region chosen from the group consisting of SEQ ID NO: 5, SEQ ID NO: 6, SEQ ID NO: 7, and SEQ ID NO: 8, a gRNA having a spacer sequence complimentary to a target sequence in the TM3 region of the T-Ag encoding region chosen from the group consisting of SEQ ID NO: 9, SEQ ID NO: 10, SEQ ID NO: 11, and SEQ ID NO: 12, or any combination of said gRNAs.

7. The method according to claim 6, wherein the gRNA having a spacer sequence complementary to a target sequence in the TM1 region is gRNA m1, the gRNA having a spacer sequence complimentary to a target sequence in the TM2 region is gRNA m2, and the gRNA having a spacer sequence complimentary to a target sequence in the TM3 region is gRNA m3.

8. The method according to claim 1, wherein the gene editing composition is encoded by at least one isolated nucleotide sequence included in at least one expression vector.

9. The method of claim 8, wherein the at least one expression vector is chosen from the group consisting of lentiviral vectors, adenovirus vectors, adeno-associated virus vectors, vesicular stomatitis virus (VSV) vectors, pox virus vectors, and retroviral vectors.

10. The method according to claim 1, wherein the immunosuppressive therapy is further defined as treatment with a composition selected from Brentuximab vedotin, Rituximab, Natalizumab, Fingolimod, Efalizumab, Vedolizumab, dimethyl fumarate, Belatacept, Tacrolimus, Sirolimus, a glucocorticoid, methotrexate, Azathioprine, Cyclosporine, Cyclophosphamide, Chlorambucil, Mycophenolate mofetil, Daclizumab, and Infliximab.

11. The method according to claim 1, wherein the gene editing composition further includes a composition chosen from the group consisting of siRNA, miRNAs, shRNAs, and RNAi.

* * * * *